(12) United States Patent
Li et al.

(10) Patent No.: US 12,344,652 B2
(45) Date of Patent: *Jul. 1, 2025

(54) HIGH-AFFINITY TCR FOR NY-ESO

(71) Applicant: XLIFESC, LTD., Guangdong (CN)

(72) Inventors: Yi Li, Guangdong (CN); Jinhua Huang, Guangdong (CN)

(73) Assignee: XLIFESC, LTD., Guangdong (CN)

( * ) Notice: Subject to any disclaimer, the term of this patent is extended or adjusted under 35 U.S.C. 154(b) by 777 days.

This patent is subject to a terminal disclaimer.

(21) Appl. No.: 16/464,780

(22) PCT Filed: Nov. 29, 2017

(86) PCT No.: PCT/CN2017/113631
§ 371 (c)(1),
(2) Date: May 29, 2019

(87) PCT Pub. No.: WO2018/099402
PCT Pub. Date: Jun. 7, 2018

(65) Prior Publication Data
US 2020/0115433 A1    Apr. 16, 2020

(30) Foreign Application Priority Data
Nov. 29, 2016 (CN) .......................... 201611078596.2

(51) Int. Cl.
*C07K 14/725* (2006.01)
*C07K 16/28* (2006.01)
*A61K 38/00* (2006.01)

(52) U.S. Cl.
CPC ...... *C07K 14/7051* (2013.01); *C07K 16/2809* (2013.01); *A61K 38/00* (2013.01); *C07K 2317/622* (2013.01); *C07K 2319/30* (2013.01)

(58) Field of Classification Search
None
See application file for complete search history.

(56) References Cited

U.S. PATENT DOCUMENTS

2015/0231202 A1    8/2015    Boulter et al.

FOREIGN PATENT DOCUMENTS

| CN | 103249430 A | 8/2013 |
|----|-------------|--------|
| CN | 105985427 A | 10/2016 |
| WO | 2005/113595 | 12/2005 |
| WO | 2016/124142 | 8/2016 |
| WO | 2016/177339 | 11/2016 |
| WO | 2017/076308 | 5/2017 |

OTHER PUBLICATIONS

Janeway et al., Immunobiology, 5th Ed., Garland Science, pp. 106-108 and 260-263, (2001).*
Garcia et al., Cell, vol. 122, 333-336, Aug. 12, 2005.*
Goyarts et al. (Mol Immunol. Jul. 1998;35(10):593-607).*
International Search Report (English and Chinese) and Written Opinion issued in PCT/CN2017/113631, dated Mar. 7, 2018, 13 pages provided.
Chen et al., "A testicular antigen aberrantly expressed in human cancers detected by autologous antibody screening", US National Library of Medicine, National Institutes of Health, vol. 94, Mar. 4, 1997, 5 pages provided.
D'Angelo et al., "Optimizing engineered TCR T cell therapy for synovial sarcoma", Journal for ImmunoTherapy of Cancer, first published Nov. 4, 2015, p. 159, Cited in the Search Report issued in the corresponding Singapore Patent Application.
Written Opinion issued in the corresponding Singapore Patent Application No. 11201904821W, dated Jul. 14, 2020, 7 pages.
Search Report issued in the corresponding Singapore Patent Application No. 11201904821W, dated Jul. 14, 2020, 3 pages.
Japanese Office Action issued in the corresponding Japanese Patent Application No. 2019-548515, dated Jul. 30, 2020, 6 pages, English google translation provided.
Korean Office Action issued in the corresponding Korean Patent Application No. 10-2019-7018348, dated Nov. 13, 2020, 11 pages, English google translation provided.
Robbins et al., "Single and Dual Amino Acid Substitutions in TCR CDRs Can Enhance Antigen-Specific T Cell Functions", The Journal of Immunology, first published in 2008, pp. 6116-6131, cited in corresponding Canadian Office Action.
Li et al., "Directed evolution of human T-cell receptors with picomolar affinities by phage display", Nature Biotechnology, vol. 23 No. 3, Mar. 2005, pp. 349-354, cited in corresponding Canadian Office Action.
Canadian Office Action issued in the corresponding Canadian Patent Application No. 3,043,951, 10 pages.
Chen et al., "Structural and kinetic basis for heightened immunogenicity of T cell vaccines", The Journal of Experimental Medicine, first published Apr. 18, 2005, pp. 1243-1255, cited in the Examination Report issued in the corresponding Australian Patent Application.
Australian Office Action issued in the corresponding Australian Patent Application No. 2017370264, dated May 11, 2020, 9 pages.
Dunn et al., "Directed evolution of human T cell receptor CDR2 residues by phage display dramatically enhances affinity for cognate peptide-MHC without increasing apparent cross-reactivity ", Protein Science, First published in 2006, pp. 710-721, cited in the European Extended Search Report issued in the corresponding European Patent Application.
Anonymous, "Uncharacterized protein from 1-18 Metalysinibacillus saudimassiliensis", Oct. 29, 2014, URL:https://www.uniprot.org/uniprot/A0A078 MFG3.txt, abstract provided, cited in the European Extended Search Report issued in the corresponding European Patent Application.

(Continued)

Primary Examiner — Brad Duffy
(74) Attorney, Agent, or Firm — HAMRE, SCHUMANN, MUELLER & LARSON, P.C.

(57) ABSTRACT

Provided is a T cell receptor (TCR) having a property of binding to a SLLMWITQC (SEQ ID NO: 105)-HLA A2 complex; and the binding affinity of the TCR to the SLL-MWITQC (SEQ ID NO: 105)-HLA A2 complex is at least twice that of a wild-type TCR to the SLLMWITQC (SEQ ID NO: 105)-HLA A2 complex. Also provided is a fusion molecule of such a TCR with a therapeutic agent. Such a TCR can be used alone or in combination with a therapeutic agent so as to target tumour cells presenting the SLL-MWITQC (SEQ ID NO: 105)-HLA A2 complex.

15 Claims, 13 Drawing Sheets

Specification includes a Sequence Listing.

(56) References Cited

OTHER PUBLICATIONS

Extended European Search Report issued in the corresponding European Patent Application No. 17875487.5., dated Aug. 10, 2020, 13 pages.

* cited by examiner

SQQGEEDPQALSIQEGENATMNCSYKTSINNLQWYRQNSGRGLVHLILIRSNEREKHSGR
LRVTLDTSKKSSSLLITASRAADTASYFCATDANGKIIFGKGTRLHILP
(SEQ ID NO:1)

Fig. 1a

DAGVIQSPRHEVTEMGQEVTLRCKPISGHDYLFWYRQTMMRGLELLIYFNNNVPIDDSGM
PEDRFSAKMPNASFSTLKIQPSEPRDSAVYFCASSLGSNEQYFGPGTRLTVT
(SEQ ID NO:2)

Fig. 1b

SQQGEEDPQALSIQEGENVTINCSYKTSINNLQWYRQNSGRGLVHLILIRSNEREKHSGRLRVTLDTSKKSSSLEITAV
RPADTASYFCATDANGKIIFGKGTRLHILP (SEQ ID NO:3)

Fig. 2a

DAGVTQSPRHESVEMGQEVTLRCKPISGHDYLFWYRQTPKRGLELLIYFNNNVPIDDSGMPEDRFSAKMPNASFSTLKI
QPVEPRDSAVYFCASSLGSNEQYFGPGTRLTVT (SEQ ID NO:4)

Fig. 2b

TCTCAACAAGGtGAAGAAGATCCGCAGGCCCTGAGTATTCAAGAAGGTGAAAATGTGACCATCAACTGCTCTTACAAAA
CGAGTATCAACAATCTGCAGTGGTACCGTCAAAATTCTGGCCGCGGTCTGGTTCATCTGATTCTGATCCGTTCCAACGA
ACGCGAAAAACACTCAGGCCGTCTGCGCGTTACCCTGGATACCAGCAAAAAATCTTCTAGTCTGGAAATCACCGCAGTC
CGTCCGGCAGATACGGCAAGCTATTTTTGTGCAACCGACGCTAATGGTAAAATTATCTTCGGCAAAGGTACCCGCCTGC
ATATTCTGCCG (SEQ ID NO:5)

Fig. 3a

GATGCGGGTGTCACGCAGTCTCCGCGTCATGAAAGTGTGGAAATGGGCCAAGAAGTTACGCTGCGCTGCAAACCGATCA
GCGGTCACGACTACCTGTTTTGGTACCGTCAGACCCCGAAACGCGGCCTGGAACTGCTGATCTACTTCAACAATAACGT
TCCGATTGATGACTCGGGTATGCCGGAAGATCGTTTTAGCGCGAAAATGCCGAATGCCTCGTTCAGCACGCTGAAAATT
CAGCCGGTCGAACCGCGTGACTCCGCAGTGTATTTTTGTGCTTCCTCACTGGGCAGTAACGAACAGTACTTCGGCCCGG
GTACCCGTCTGACCGTGACG (SEQ ID NO:6)

Fig. 3b

GGGSEGGGSEGGGSEGGGSEGGTG (SEQ ID NO:7)

Fig. 4a

GGCGGTGGCTCCGAAGGTGGCGGTTCAGAAGGCGGTGGCTCGGAAGGTGGCGGTAGCGAAGGCGGTACCGGT (SEQ ID
NO:8)

Fig. 4b

SQQGEEDPQALSIQEGENVTINCSYKTSINNLQWYRQNSGRGLVHLILIRSNEREKHSGRLRVTLDTSKKSSSLEITAV
RPADTASYFCATDAFAWWIFGKGTRLHILP
(SEQ ID NO:9)

Fig. 5 (1)

SQQGEEDPQALSIQEGENVTINCSYKGWAQNLQWYRQNSGRGLVHLILIRTGEQEKHSGRLRVTLDTSKKSSSLEITAV
RPADTASYFCATDANARWNFGKGTRLHILP
(SEQ ID NO:10)

Fig. 5 (2)

SQQGEEDPQALSIQEGENVTINCSYK<u>GS</u>IQNLQWYRQNSGRGLVHLILI<u>RTGEQ</u>EKHSGRLRVTLDTSKKSSSLEITAV
RPADTASYFCATDAN<u>ARWE</u>FGKGTRLHILP
(SEQ ID NO:11)

Fig. 5 (3)

SQQGEEDPQALSIQEGENVTINCSYK<u>GS</u>IQNLQWYRQNSGRGLVHLILI<u>RTGEQ</u>EKHSGRLRVTLDTSKKSSSLEITAV
RPADTASYFCATDAN<u>ARWD</u>FGKGTRLHILP
(SEQ ID NO:12)

Fig. 5 (4)

SQQGEEDPQALSIQEGENVTINCSYK<u>GWAQ</u>NLQWYRQNSGRGLVHLILIRSNEREKHSGRLRVTLDTSKKSSSLEITAV
RPADTASYFCATDAN<u>ARWN</u>FGKGTRLHILP
(SEQ ID NO:13)

Fig. 5 (5)

SQQGEEDPQALSIQEGENVTINCSYK<u>GWVQ</u>NLQWYRQNSGRGLVHLILI<u>RTGEQ</u>EKHSGRLRVTLDTSKKSSSLEITAV
RPADTASYFCATDAN<u>ARWD</u>FGKGTRLHILP
(SEQ ID NO:14)

Fig. 5 (6)

SQQGEEDPQALSIQEGENVTINCSYK<u>GS</u>IQNLQWYRQNSGRGLVHLILIRSNEREKHSGRLRVTLDTSKKSSSLEITAV
RPADTASYFCATDAN<u>ARWD</u>FGKGTRLHILP
(SEQ ID NO:15)

Fig. 5 (7)

SQQGEEDPQALSIQEGENVTINCSYK<u>GWAQ</u>NRQNSGRGLVHLILIRSNEREKHSGRLRVTLDTSKKSSSLEITAVRPAD
TASYFCATDAN<u>ARWD</u>FGKGTRLHILP
(SEQ ID NO:16)

Fig. 5 (8)

SQQGEEDPQALSIQEGENVTINCSYK<u>GS</u>IQNLQWYRQNSGRGLVHLILIRSNEREKHSGRLRVTLDTSKKSSSLEITAV
RPADTASYFCATDAN<u>ARWE</u>FGKGTRLHILP
(SEQ ID NO:17)

Fig. 5 (9)

SQQGEEDPQALSIQEGENVTINCSYKTSINNLQWYRQNSGRGLVHLILIRSNEREKHSGRLRVTLDTSKKSSSLEITAV
RPADTASYFC<u>MYDE</u>NGKIIFGKGTRLHILP
(SEQ ID NO:18)

Fig. 5 (10)

SQQGEEDPQALSIQEGENVTINCSYKTSINNLQWYRQNSGRGLVHLILIRSNEREKHSGRLRVTLDTSKKSSSLEITAV
RPADTASYFC<u>MYDQ</u>NGKIIFGKGTRLHILP
(SEQ ID NO:19)

Fig. 5 (11)

SQQGEEDPQALSIQEGENVTINCSYKTSINNLQWYRQNSGRGLVHLILIRSNEREKHSGRLRVTLDTSKKSSSLEITAV
RPADTASYFCATDA<u>YGTVQ</u>FGKGTRLHILP
(SEQ ID NO:20)

Fig. 5 (12)

SQQGEEDPQALSIQEGENVTINCSYKTSINNLQWYRQNSGRGLVHLILIRSNEREKHSGRLRVTLDTSKKSSSLEITAV
RPADTASYFCATDANG<u>TVQ</u>FGKGTRLHILP
(SEQ ID NO:21)

Fig. 5 (13)

SQQGEEDPQALSIQEGENVTINCSYKTSINNLQWYRQNSGRGLVHLILIRSNEREKHSGRLRVTLDTSKKSSSLEITAV
RPADTASYFCATDANGSVQFGKGTRLHILP
(SEQ ID NO:22)

Fig. 5 (14)

SQQGEEDPQALSIQEGENVTINCSYKTSINNLQWYRQNSGRGLVHLILIRSNEREKHSGRLRVTLDTSKKSSSLEITAV
RPADTASYFCATDAYGRYIFGKGTRLHILP
(SEQ ID NO:23)

Fig. 5 (15)

SQQGEEDPQALSIQEGENVTINCSYKTSINNLQWYRQNSGRGLVHLILIRSNEREKHSGRLRVTLDTSKKSSSLEITAV
RPADTASYFCATDANQMWKFGKGTRLHILP
(SEQ ID NO:24)

Fig. 5 (16)

SQQGEEDPQALSIQEGENVTINCSYKTSINNLQWYRQNSGRGLVHLILIRSNEREKHSGRLRVTLDTSKKSSSLEITAV
RPADTASYFCATDAYGLPIFGKGTRLHILP
(SEQ ID NO:25)

Fig. 5 (17)

SQQGEEDPQALSIQEGENVTINCSYKTSINNLQWYRQNSGRGLVHLILIRSNEREKHSGRLRVTLDTSKKSSSLEITAV
RPADTASYFCATDANGLPVFGKGTRLHILP
(SEQ ID NO:26)

Fig. 5 (18)

SQQGEEDPQALSIQEGENVTINCSYKTSINNLQWYRQNSGRGLVHLILIRSNEREKHSGRLRVTLDTSKKSSSLEITAV
RPADTASYFCATDANGRWEFGKGTRLHILP
(SEQ ID NO:27)

Fig. 5 (19)

SQQGEEDPQALSIQEGENVTINCSYKTSINNLQWYRQNSGRGLVHLILIRSNEREKHSGRLRVTLDTSKKSSSLEITAV
RPADTASYFCATDANGTVGFGKGTRLHILP
(SEQ ID NO:28)

Fig. 5 (20)

SQQGEEDPQALSIQEGENVTINCSYKTSINNLQWYRQNSGRGLVHLILIRSNEREKHSGRLRVTLDTSKKSSSLEITAV
RPADTASYFCATDANGRWMFGKGTRLHILP
(SEQ ID NO:29)

Fig. 5 (21)

SQQGEEDPQALSIQEGENVTINCSYKTSINNLQWYRQNSGRGLVHLILIRSNEREKHSGRLRVTLDTSKKSSSLEITAV
RPADTASYFCATDANGLWSFGKGTRLHILP
(SEQ ID NO:30)

Fig. 5 (22)

SQQGEEDPQALSIQEGENVTINCSYKGWAQNLQWYRQNSGRGLVHLILIRTGEQEKHSGRLRVTLDTSKKSSSLEITAV
RPADTASYFCATDANARWDFGKGTRLHILP
(SEQ ID NO:31)

Fig. 5 (23)

SQQGEEDPQALSIQEGENVTINCSYKGWAQNLQWYRQNSGRGLVHLILIRTGQAEKHSGRLRVTLDTSKKSSSLEITAV
RPADTASYFCATDANARWEFGKGTRLHILP
(SEQ ID NO:32)

Fig. 5 (24)

SQQGEEDPQALSIQEGENVTINCSYK<u>GSIQ</u>NLQWYRQNSGRGLVHLILI<u>RSNEREK</u>HSGRLRVTLDTSKKSSSLEITAV
RPADTASYFCATDA<u>FAWW</u>IFGKGTRLHILP
(SEQ ID NO:33)

Fig. 5 (25)

SQQGEEDPQALSIQEGENVTINCSYK<u>GWVQ</u>NLQWYRQNSGRGLVHLILI<u>RTGEQEK</u>HSGRLRVTLDTSKKSSSLEITAV
RPADTASYFCATDAN<u>ARWN</u>FGKGTRLHILP
(SEQ ID NO:34)

Fig. 5 (26)

SQQGEEDPQALSIQEGENVTINCSYK<u>GSIQ</u>NLQWYRQNSGRGLVHLILI<u>RTGEQEK</u>HSGRLRVTLDTSKKSSSLEITAV
RPADTASYFCATDA<u>WARW</u>IFGKGTRLHILP
(SEQ ID NO:35)

Fig. 5 (27)

SQQGEEDPQALSIQEGENVTINCSYK<u>GWVQ</u>NLQWYRQNSGRGLVHLILI<u>RTGQAEK</u>HSGRLRVTLDTSKKSSSLEITAV
RPADTASYFCATDAN<u>ARWE</u>FGKGTRLHILP
(SEQ ID NO:36)

Fig. 5 (28)

SQQGEEDPQALSIQEGENVTINCSYK<u>GSIQ</u>NLQWYRQNSGRGLVHLILI<u>RTGEQEK</u>HSGRLRVTLDTSKKSSSLEITAV
RPADTASYFCATDAN<u>ARWN</u>FGKGTRLHILP
(SEQ ID NO:37)

Fig. 5 (29)

DAGVTQSPRHESVEMGQEVTLRCKPISGHDYLFWYRQTPKRGLELLIYF<u>NHGAV</u>IDDSGMPEDRFSAKMPNASFSTLKI
QPVEPRDSAVYFCAS<u>SLG</u>SNEQYFGPGTRLTVT
(SEQ ID NO:38)

Fig. 6 (1)

DAGVTQSPRHESVEMGQEVTLRCKPISGHDYLFWYRQTPKRGLELLIYF<u>NHGAV</u>IDDSGMPEDRFSAKMPNASFSTLKI
QPVEPRDSAVYFCAS<u>QRG</u>SNEQYFGPGTRLTVT
(SEQ ID NO:39)

Fig. 6 (2)

DAGVTQSPRHESVEMGQEVTLRCKPISGHDYLFWYRQTPKRGLELLIYF<u>NHGAV</u>IDDSGMPEDRFSAKMPNASFSTLKI
QPVEPRDSAVYFCAS<u>QKGA</u>NEQYFGPGTRLTVT
(SEQ ID NO:40)

Fig. 6 (3)

DAGVTQSPRHESVEMGQEVTLRCKPISGHDYLFWYRQTPKRGLELLIYF<u>NHGAV</u>IDDSGMPEDRFSAKMPNASFSTLKI
QPVEPRDSAVYFCAS<u>QLG</u>SNEQYFGPGTRLTVT
(SEQ ID NO:41)

Fig. 6 (4)

DAGVTQSPRHESVEMGQEVTLRCKPISGHDYLFWYRQTPKRGLELLIYF<u>NHGAV</u>IDDSGMPEDRFSAKMPNASFSTLKI
QPVEPRDSAVYFCAS<u>QLGA</u>NEQYFGPGTRLTVT
(SEQ ID NO:42)

Fig. 6 (5)

DAGVTQSPRHESVEMGQEVTLRCKPISGHDYLFWYRQTPKRGLELLIYF<u>NNNVP</u>IDDSGMPEDRFSAKMPNASFSTLKI
QPVEPRDSAVYFCAS<u>QLGG</u>NEQYFGPGTRLTVT
(SEQ ID NO:43)

Fig. 6 (6)

DAGVTQSPRHESVEMGQEVTLRCKPISGHDYLFWYRQTPKRGLELLIYFNNNVPIDDSGMPEDRFSAKMPNASFSTLKI
QPVEPRDSAVYFCASQKGANEQYFGPGTRLTVT
(SEQ ID NO:44)

Fig. 6(7)

DAGVTQSPRHESVEMGQEVTLRCKPISGHDYLFWYRQTPKRGLELLIYFNNNVPIDDSGMPEDRFSAKMPNASFSTLKI
QPVEPRDSAVYFCASQLGPNEQYFGPGTRLTVT
(SEQ ID NO:45)

Fig. 6(8)

DAGVTQSPRHESVEMGQEVTLRCKPISGHDYLFWYRQTPKRGLELLIYFNNNVPIDDSGMPEDRFSAKMPNASFSTLKI
QPVEPRDSAVYFCASQRGANEQYFGPGTRLTVT
(SEQ ID NO:46)

Fig. 6(9)

DAGVTQSPRHESVEMGQEVTLRCKPISGHDYLFWYRQTPKRGLELLIYFNNNVPIDDSGMPEDRFSAKMPNASFSTLKI
QPVEPRDSAVYFCASQMGSNEQYFGPGTRLTVT
(SEQ ID NO:47)

Fig. 6(10)

DAGVTQSPRHESVEMGQEVTLRCKPISGHDYLFWYRQTPKRGLELLIYFNNNVPIDDSGMPEDRFSAKMPNASFSTLKI
QPVEPRDSAVYFCASQLGSNEQYFGPGTRLTVT
(SEQ ID NO:48)

Fig. 6(11)

DAGVTQSPRHESVEMGQEVTLRCKPISGHDYLFWYRQTPKRGLELLIYFNNNVPIDDSGMPEDRFSAKMPNASFSTLKI
QPVEPRDSAVYFCASQLGANEQYFGPGTRLTVT
(SEQ ID NO:49)

Fig. 6(12)

DAGVTQSPRHESVEMGQEVTLRCKPISGHDYLFWYRQTPKRGLELLIYFNNNVPIDDSGMPEDRFSAKMPNASFSTLKI
QPVEPRDSAVYFCASQMGSNEQYFGPGTRLTVT
(SEQ ID NO:50)

Fig. 6(13)

DAGVTQSPRHESVEMGQEVTLRCKPISGHDYLFWYRQTPKRGLELLIYFNNNVPIDDSGMPEDRFSAKMPNASFSTLKI
QPVEPRDSAVYFCASQRGSNEQYFGPGTRLTVT
(SEQ ID NO:51)

Fig. 6(14)

DAGVTQSPRHESVEMGQEVTLRCKPISGHDYLFWYRQTPKRGLELLIYFNNNVPIDDSGMPEDRFSAKMPNASFSTLKI
QPVEPRDSAVYFCASQMGANEQYFGPGTRLTVT
(SEQ ID NO:52)

Fig. 6(15)

DAGVTQSPRHESVEMGQEVTLRCKPISGHDYLFWYRQTPKRGLELLIYFNNNVPIDDSGMPEDRFSAKMPNASFSTLKI
QPVEPRDSAVYFCASMLGSNEQYFGPGTRLTVT
(SEQ ID NO:53)

Fig. 6(16)

SQQGEEDPQALSIQEGENVTINCSYKTSINNLQWYRQNSGRGLVHLILIRSNEREKHSGRLRVTLDTSKKSSSLEITAV
RPADTASYFCATDANGKIIFGKGTRLHILPGGGSEGGGSEGGGSEGGGSEGGTGDAGVTQSPRHESVEMGQEVTLRCKP
ISGHDYLFWYRQTPKRGLELLIYFNNNVPIDDSGMPEDRFSAKMPNASFSTLKIQPVEPRDSAVYFCASSLGSNEQYFG
PGTRLTVT (SEQ ID NO:54)

Fig. 7a

TCTCAACAAGGtGAAGAAGATCCGCAGGCCCTGAGTATTCAAGAAGGTGAAAATGTGACCATCAACTGCTCTTACAAAA
CGAGTATCAACAATCTGCAGTGGTACCGTCAAAATTCTGGCCGCGGTCTGGTTCATCTGATTCTGATCCGTTCCAACGA
ACGCGAAAAACACTCAGGCCGTCTGCGCGTTACCCTGGATACCAGCAAAAAATCTTCTAGTCTGGAAATCACCGCAGTC
CGTCCGGCAGATACGGCAAGCTATTTTGTGCAACCGACGCTAATGGTAAAATTATCTTCGGCAAAGGTACCCGCCTGC
ATATTCTGCCGGGCGGTGGCTCCGAAGGTGGCGGTTCAGAAGGCGGTGGCTCGGAAGGTGGCGGTAGCGAAGGCGGTAC
CGGTGATGCGGGTGTCACGCAGTCTCCGCGTCATGAAAGTGTGGAAATGGGCCAAGAAGTTACGCTGCGCTGCAAACCG
ATCAGCGGTCACGACTACCTGTTTTGGTACCGTCAGACCCCGAAACGCGGCCTGGAACTGCTGATCTACTTCAACAATA
ACGTTCCGATTGATGACTCGGGTATGCCGGAAGATCGTTTTAGCGCGAAAATGCCGAATGCCTCGTTCAGCACGCTGAA
AATTCAGCCGGTCGAACCGCGTGACTCCGCAGTGTATTTTTGTGCTTCCTCACTGGGCAGTAACGAACAGTACTTCGGC
CCGGGTACCCGTCTGACCGTGACG (SEQ ID NO:55)

Fig. 7b

SQQGEEDPQALSIQEGENATMNCSYKTSINNLQWYRQNSGRGLVHLILIRSNEREKHSGRLRVTLDTSKKSSSLLITAS
RAADTASYFCATDANGKIIFGKGTRLHILPNIQNPDPAVYQLRDSKSSDKSVCLFTDFDSQTNVSQSKDSDVYITDKCV
LDMRSMDFKSNSAVAWSNKSDFACANAFNNSIIPEDTFFPSPESS (SEQ ID NO:56)

Fig. 8a

DAGVIQSPRHEVTEMGQEVTLRCKPISGHDYLFWYRQTMMRGLELLIYFNNNVPIDDSGMPEDRFSAKMPNASFSTLKI
QPSEPRDSAVYFCASSLGSNEQYFGPGTRLTVTEDLKNVFPPEVAVFEPSEAEISHTQKATLVCLATGFYPDHVELSWW
VNGKEVHSGVCTDPQPLKEQPALNDSRYALSSRLRVSATFWQDPRNHFRCQVQFYGLSENDEWTQDRAKPVTQIVSAEA
WGRAD (SEQ ID NO:57)

Fig. 8b

SQQGEEDPQALSIQEGENATMNCSYKTSINNLQWYRQNSGRGLVHLILIRSNEREKHSGRLRVTLDTSKKSSSLLITAS
RAADTASYFCATDAFAWWIFGKGTRLHILP
(SEQ ID NO:58)

Fig. 9 (1)

SQQGEEDPQALSIQEGENATMNCSYKGWAQNLQWYRQNSGRGLVHLILIRTGEQEKHSGRLRVTLDTSKKSSSLLITAS
RAADTASYFCATDANARWNFGKGTRLHILP
(SEQ ID NO:59)

Fig. 9 (2)

SQQGEEDPQALSIQEGENATMNCSYKGSIQNLQWYRQNSGRGLVHLILIRTGEQEKHSGRLRVTLDTSKKSSSLLITAS
RAADTASYFCATDANARWEFGKGTRLHILP
(SEQ ID NO:60)

Fig. 9 (3)

SQQGEEDPQALSIQEGENATMNCSYKGSIQNLQWYRQNSGRGLVHLILIRTGEQEKHSGRLRVTLDTSKKSSSLLITAS
RAADTASYFCATDANARWDFGKGTRLHILP
(SEQ ID NO:61)

Fig. 9 (4)

SQQGEEDPQALSIQEGENATMNCSYKGWAQNLQWYRQNSGRGLVHLILIRSNEREKHSGRLRVTLDTSKKSSSLLITAS
RAADTASYFCATDANARWNFGKGTRLHILP
(SEQ ID NO:62)

Fig. 9 (5)

SQQGEEDPQALSIQEGENATMNCSYKGWVQNLQWYRQNSGRGLVHLILIRTGEQEKHSGRLRVTLDTSKKSSSLLITAS
RAADTASYFCATDANARWDFGKGTRLHILP
(SEQ ID NO:63)

Fig. 9 (6)

SQQGEEDPQALSIQEGENATMNCSYK<u>GSIQNL</u>QWYRQNSGRGLVHLILIRSNEREKHSGRLRVTLDTSKKSSSLLITAS
RAADTASYFCATDAN<u>ARWD</u>FGKGTRLHILP
(SEQ ID NO:64)

Fig. 9 (7)

SQQGEEDPQALSIQEGENATMNCSYK<u>GWAQN</u>RQNSGRGLVHLILIRSNEREKHSGRLRVTLDTSKKSSSLLITASRAAD
TASYFCATDAN<u>ARWD</u>FGKGTRLHILP
(SEQ ID NO:65)

Fig. 9 (8)

SQQGEEDPQALSIQEGENATMNCSYK<u>GSIQNL</u>QWYRQNSGRGLVHLILIRSNEREKHSGRLRVTLDTSKKSSSLLITAS
RAADTASYFCATDAN<u>ARWE</u>FGKGTRLHILP
(SEQ ID NO:66)

Fig. 9 (9)

SQQGEEDPQALSIQEGENATMNCSYK<u>TSINNL</u>QWYRQNSGRGLVHLILIRSNEREKHSGRLRVTLDTSKKSSSLLITAS
RAADTASYFC<u>MYDENGKI</u>IFGKGTRLHILP
(SEQ ID NO:67)

Fig. 9 (10)

SQQGEEDPQALSIQEGENATMNCSYK<u>TSINNL</u>QWYRQNSGRGLVHLILIRSNEREKHSGRLRVTLDTSKKSSSLLITAS
RAADTASYFC<u>MYDQNGKI</u>IFGKGTRLHILP
(SEQ ID NO:68)

Fig. 9 (11)

SQQGEEDPQALSIQEGENATMNCSYK<u>TSINNL</u>QWYRQNSGRGLVHLILIRSNEREKHSGRLRVTLDTSKKSSSLLITAS
RAADTASYFCATDA<u>YGTVQ</u>FGKGTRLHILP
(SEQ ID NO:69)

Fig. 9 (12)

SQQGEEDPQALSIQEGENATMNCSYK<u>TSINNL</u>QWYRQNSGRGLVHLILIRSNEREKHSGRLRVTLDTSKKSSSLLITAS
RAADTASYFCATDANG<u>TVQ</u>FGKGTRLHILP
(SEQ ID NO:70)

Fig. 9 (13)

SQQGEEDPQALSIQEGENATMNCSYK<u>TSINNL</u>QWYRQNSGRGLVHLILIRSNEREKHSGRLRVTLDTSKKSSSLLITAS
RAADTASYFCATDANG<u>SVQ</u>FGKGTRLHILP
(SEQ ID NO:71)

Fig. 9 (14)

SQQGEEDPQALSIQEGENATMNCSYK<u>TSINNL</u>QWYRQNSGRGLVHLILIRSNEREKHSGRLRVTLDTSKKSSSLLITAS
RAADTASYFCATDA<u>YGRY</u>IFGKGTRLHILP
(SEQ ID NO:72)

Fig. 9 (15)

SQQGEEDPQALSIQEGENATMNCSYK<u>TSINNL</u>QWYRQNSGRGLVHLILIRSNEREKHSGRLRVTLDTSKKSSSLLITAS
RAADTASYFCATDAN<u>QMWK</u>FGKGTRLHILP
(SEQ ID NO:73)

Fig. 9 (16)

SQQGEEDPQALSIQEGENATMNCSYK<u>TSINNL</u>QWYRQNSGRGLVHLILIRSNEREKHSGRLRVTLDTSKKSSSLLITAS
RAADTASYFCATDA<u>YGLP</u>IFGKGTRLHILP
(SEQ ID NO:74)

Fig. 9 (17)

SQQGEEDPQALSIQEGENATMNCSYKTSINNLQWYRQNSGRGLVHLILIRSNEREKHSGRLRVTLDTSKKSSSLLITAS
RAADTASYFCATDANGLPVFGKGTRLHILP
(SEQ ID NO:75)

Fig. 9 (18)

SQQGEEDPQALSIQEGENATMNCSYKTSINNLQWYRQNSGRGLVHLILIRSNEREKHSGRLRVTLDTSKKSSSLLITAS
RAADTASYFCATDANGRWEFGKGTRLHILP
(SEQ ID NO:76)

Fig. 9 (19)

SQQGEEDPQALSIQEGENATMNCSYKTSINNLQWYRQNSGRGLVHLILIRSNEREKHSGRLRVTLDTSKKSSSLLITAS
RAADTASYFCATDANGTVGFGKGTRLHILP
(SEQ ID NO:77)

Fig. 9 (20)

SQQGEEDPQALSIQEGENATMNCSYKTSINNLQWYRQNSGRGLVHLILIRSNEREKHSGRLRVTLDTSKKSSSLLITAS
RAADTASYFCATDANGRWMFGKGTRLHILP
(SEQ ID NO:78)

Fig. 9 (21)

SQQGEEDPQALSIQEGENATMNCSYKTSINNLQWYRQNSGRGLVHLILIRSNEREKHSGRLRVTLDTSKKSSSLLITAS
RAADTASYFCATDANGLWSFGKGTRLHILP
(SEQ ID NO:79)

Fig. 9 (22)

SQQGEEDPQALSIQEGENATMNCSYKGWAQNLQWYRQNSGRGLVHLILIRTGEQEKHSGRLRVTLDTSKKSSSLLITAS
RAADTASYFCATDANARWDFGKGTRLHILP
(SEQ ID NO:80)

Fig. 9 (23)

SQQGEEDPQALSIQEGENATMNCSYKGWAQNLQWYRQNSGRGLVHLILIRTGQAEKHSGRLRVTLDTSKKSSSLLITAS
RAADTASYFCATDANARWEFGKGTRLHILP
(SEQ ID NO:81)

Fig. 9 (24)

SQQGEEDPQALSIQEGENATMNCSYKGSIQNLQWYRQNSGRGLVHLILIRSNEREKHSGRLRVTLDTSKKSSSLLITAS
RAADTASYFCATDAFAWWIFGKGTRLHILP
(SEQ ID NO:82)

Fig. 9 (25)

SQQGEEDPQALSIQEGENATMNCSYKGWVQNLQWYRQNSGRGLVHLILIRTGEQEKHSGRLRVTLDTSKKSSSLLITAS
RAADTASYFCATDANARWNFGKGTRLHILP
(SEQ ID NO:83)

Fig. 9 (26)

SQQGEEDPQALSIQEGENATMNCSYKGSIQNLQWYRQNSGRGLVHLILIRTGEQEKHSGRLRVTLDTSKKSSSLLITAS
RAADTASYFCATDAWARWIFGKGTRLHILP
(SEQ ID NO:84)

Fig. 9 (27)

SQQGEEDPQALSIQEGENATMNCSYK<u>GWVQ</u>NLQWYRQNSGRGLVHLILI<u>RTGQ</u>AEKHSGRLRVTLDTSKKSSSLLITAS
RAADTASYFCATDAN<u>ARWEF</u>GKGTRLHILP (SEQ ID NO:85)

Fig. 9 (28)

SQQGEEDPQALSIQEGENATMNCSYK<u>GSIQ</u>NLQWYRQNSGRGLVHLILI<u>RTGEQ</u>EKHSGRLRVTLDTSKKSSSLLITAS
RAADTASYFCATDAN<u>ARWN</u>FGKGTRLHILP (SEQ ID NO:86)

Fig. 9 (29)

DAGVIQSPRHEVTEMGQEVTLRCKPISGHDYLFWYRQTMMRGLELLIYFN<u>HGAV</u>IDDSGMPEDRFSAKMPNASFSTLKI
QPSEPRDSAVYFCASSLGSNEQYFGPGTRLTVT (SEQ ID NO:87)

Fig. 10 (1)

DAGVIQSPRHEVTEMGQEVTLRCKPISGHDYLFWYRQTMMRGLELLIYFN<u>HGAV</u>IDDSGMPEDRFSAKMPNASFSTLKI
QPSEPRDSAVYFCAS<u>QR</u>GSNEQYFGPGTRLTVT (SEQ ID NO:88)

Fig. 10 (2)

DAGVIQSPRHEVTEMGQEVTLRCKPISGHDYLFWYRQTMMRGLELLIYFN<u>HGAV</u>IDDSGMPEDRFSAKMPNASFSTLKI
QPSEPRDSAVYFCAS<u>QKGA</u>NEQYFGPGTRLTVT (SEQ ID NO:89)

Fig. 10 (3)

DAGVIQSPRHEVTEMGQEVTLRCKPISGHDYLFWYRQTMMRGLELLIYFN<u>HGAV</u>IDDSGMPEDRFSAKMPNASFSTLKI
QPSEPRDSAVYFCAS<u>Q</u>LGSNEQYFGPGTRLTVT (SEQ ID NO:90)

Fig. 10 (4)

DAGVIQSPRHEVTEMGQEVTLRCKPISGHDYLFWYRQTMMRGLELLIYFN<u>HGAV</u>IDDSGMPEDRFSAKMPNASFSTLKI
QPSEPRDSAVYFCAS<u>Q</u>L<u>GA</u>NEQYFGPGTRLTVT (SEQ ID NO:91)

Fig. 10 (5)

DAGVIQSPRHEVTEMGQEVTLRCKPISGHDYLFWYRQTMMRGLELLIYFNNNVPIDDSGMPEDRFSAKMPNASFSTLKI
QPSEPRDSAVYFCAS<u>Q</u>LGGNEQYFGPGTRLTVT (SEQ ID NO:92)

Fig. 10 (6)

DAGVIQSPRHEVTEMGQEVTLRCKPISGHDYLFWYRQTMMRGLELLIYFNNNVPIDDSGMPEDRFSAKMPNASFSTLKI
QPSEPRDSAVYFCAS<u>QKGA</u>NEQYFGPGTRLTVT (SEQ ID NO:93)

Fig. 10 (7)

DAGVIQSPRHEVTEMGQEVTLRCKPISGHDYLFWYRQTMMRGLELLIYFNNNVPIDDSGMPEDRFSAKMPNASFSTLKI
QPSEPRDSAVYFCAS<u>Q</u>LG<u>P</u>NEQYFGPGTRLTVT (SEQ ID NO:94)

Fig. 10 (8)

DAGVIQSPRHEVTEMGQEVTLRCKPISGHDYLFWYRQTMMRGLELLIYFNNNVPIDDSGMPEDRFSAKMPNASFSTLKI
QPSEPRDSAVYFCAS<u>QR</u>G<u>A</u>NEQYFGPGTRLTVT (SEQ ID NO:95)

Fig. 10 (9)

DAGVIQSPRHEVTEMGQEVTLRCKPISGHDYLFWYRQTMMRGLELLIYFNNNVPIDDSGMPEDRFSAKMPNASFSTLKI
QPSEPRDSAVYFCASQMGSNEQYFGPGTRLTVT (SEQ ID NO:96)

Fig. 10 (10)

DAGVIQSPRHEVTEMGQEVTLRCKPISGHDYLFWYRQTMMRGLELLIYFNNNVPIDDSGMPEDRFSAKMPNASFSTLKI
QPSEPRDSAVYFCASQLGSNEQYFGPGTRLTVT (SEQ ID NO:97)

Fig. 10 (11)

DAGVIQSPRHEVTEMGQEVTLRCKPISGHDYLFWYRQTMMRGLELLIYFNNNVPIDDSGMPEDRFSAKMPNASFSTLKI
QPSEPRDSAVYFCASQLGANEQYFGPGTRLTVT (SEQ ID NO:98)

Fig. 10 (12)

DAGVIQSPRHEVTEMGQEVTLRCKPISGHDYLFWYRQTMMRGLELLIYFNNNVPIDDSGMPEDRFSAKMPNASFSTLKI
QPSEPRDSAVYFCASQMGSNEQYFGPGTRLTVT (SEQ ID NO:99)

Fig. 10 (13)

DAGVIQSPRHEVTEMGQEVTLRCKPISGHDYLFWYRQTMMRGLELLIYFNNNVPIDDSGMPEDRFSAKMPNASFSTLKI
QPSEPRDSAVYFCASQRGSNEQYFGPGTRLTVT (SEQ ID NO:100)

Fig. 10 (14)

DAGVIQSPRHEVTEMGQEVTLRCKPISGHDYLFWYRQTMMRGLELLIYFNNNVPIDDSGMPEDRFSAKMPNASFSTLKI
QPSEPRDSAVYFCASQMGANEQYFGPGTRLTVT (SEQ ID NO:101)

Fig. 10 (15)

DAGVIQSPRHEVTEMGQEVTLRCKPISGHDYLFWYRQTMMRGLELLIYFNNNVPIDDSGMPEDRFSAKMPNASFSTLKI
QPSEPRDSAVYFCASMLGSNEQYFGPGTRLTVT (SEQ ID NO:102)

Fig. 10 (16)

SQQGEEDPQALSIQEGENATMNCSYKTSINNLQWYRQNSGRGLVHLILIRSNEREKHSGRLRVTLDTSKKSSSLLITAS
RAADTASYFCATDANGKIIFGKGTRLHILPNIQNPDPAVYQLRDSKSSDKSVCLFTDFDSQTNVSQSKDSDVYITDKTV
LDMRSMDFKSNSAVAWSNKSDFACANAFNNSIIPEDTFFPSPESS (SEQ ID NO:103)

Fig. 11a

DAGVIQSPRHEVTEMGQEVTLRCKPISGHDYLFWYRQTMMRGLELLIYFNNNVPIDDSGMPEDRFSAKMPNASFSTLKI
QPSEPRDSAVYFCASSLGSNEQYFGPGTRLTVTEDLKNVFPPEVAVFEPSEAEISHTQKATLVCLATGFYPDHVELSWW
VNGKEVHSGVSTDPQPLKEQPALNDSRYALSSRLRVSATFWQDPRNHFRCQVQFYGLSENDEWTQDRAKPVTQIVSAEA
WGRAD (SEQ ID NO:104)

Fig. 11b

HIGH-AFFINITY TCR FOR NY-ESO

STATEMENT REGARDING SEQUENCE LISTING

This application contains a Sequence Listing which has been submitted electronically in ASCII format and is hereby incorporated by reference in its entirety. Said ASCII copy, created on Jun. 6, 2022, is named P2019-0257_Sequence_listing.txt and is 120,266 bytes in size.

TECHNICAL FIELD

The present invention relates to the field of biotechnology, and in particular to a T cell receptor (TCR) capable of recognizing a polypeptide derived from NY-ESO-1 protein. The invention also relates to the preparation and uses of such receptors.

BACKGROUND

There are only two types of molecules that can recognize antigens in a specific manner. One is immunoglobulin or antibody and the other is T cell receptor (TCR), which is α/β or γ/δ heterodimeric glycoprotein on cell membrane. The physical repertoire of TCR of immune system is generated in thymus through V (D) J recombination, followed by positive and negative selections. In peripheral environment, TCRs mediate the recognition of specific Major Histocompatibility Complex-peptide complexes (pMHC) by T cells and, as such, are essential to the immunological functioning of cells in the immune system.

TCR is the only receptor for presenting specific peptide antigens in Major Histocompatibility Complex (MHC). The exogenous or endogenous peptides may be the only sign of abnormality in a cell. In the immune system, once antigen-specific TCRs bind with pMHC complexes, it causes direct physical contact of a T-cell and an antigen presenting cell (APC). Then, the interaction of other membrane molecules in T cell and APC occurs and the subsequent cell signaling and other physiological responses are initiated so that a range of different antigen-specific T cells exert immune effects on their target cells.

Molecular ligands of MHC class I and class II corresponding to TCR are also proteins of the immunoglobulin superfamily but are specific for antigen presentation, and different individuals have different MHCs, thereby presenting different short peptides in one protein antigen to the surface of respective APC cells. Human MHC is commonly referred to as HLA gene or HLA complex.

Short peptide SLLMWITQC (SEQ ID NO: 105) is derived from NY-ESO-1 protein expressed by various tumor cells (Chen et al., (1997) PNAS USA 94 1914-1918). A HLA molecule of type I in tumor cells presents a short peptide derived from NY-ESO-1 including SLLMWITQC (SEQ ID NO: 105). Therefore, SLLMWITQC (SEQ ID NO: 105)-HLA A2 complex provides a marker for TCR targeting tumor cells. The TCR capable of binding to SLLMWITQC (SEQ ID NO: 105)-HLA A2 complex has high application value for treating tumors. For example, a TCR capable of targeting the tumor cell marker can be used to deliver a cytotoxic agent or immunostimulatory agent to target cells, or have the same transformed into T cells, such that the T cell expressing the TCR can destroy the tumor cells and can be administered to a patient during the course of treatment of so called adoptive immunotherapy. For the former purpose, the ideal TCR has a higher affinity, allowing the TCR to reside on the targeted cells for a long period of time. For the latter purpose, it is preferred to use a medium affinity TCR. Accordingly, a skilled person in the art is directed to developing TCRs that can be used to target tumor cell markers for different purposes.

SUMMARY OF THE INVENTION

It is an object of the present invention to provide a TCR having a higher affinity for SLLMWITQC (SEQ ID NO: 105)-HLA A2 complex.

It is still another object of the present invention to provide a method for preparing the TCR of the above type and the use of the TCR of the above type.

In a first aspect of the invention, a T cell receptor (TCR) is provided, which has an activity of binding to SLLMWITQC(SEQ ID NO: 105)-HLA A2 complex.

In another preferred embodiment, the T cell receptor (TCR) has an activity of binding to SLLMWITQC(SEQ ID NO: 105)-HLA A2 complex, and the T cell receptor comprises a TCR α chain variable domain and a TCR β chain variable domain, the TCRα chain variable domain comprises three CDR regions, and the reference sequences of the three CDR regions of the TCR α chain variable domain are listed as follows, CDR1α: TSINN (SEQ ID NO: 106)
CDR2α: IRSNERE (SEQ ID NO: 107)
CDR3α: ATDANGKII (SEQ ID NO: 108) and contains at least one of the following mutations:

| Residue before mutation | Residue after mutation |
|---|---|
| T at position 1 of CDR1α | G |
| S at position 2 of CDR1α | W |
| I at position 3 of CDR1α | A or V |
| N at position 4 of CDR1α | Q |
| S at position 3 of CDR2α | T |
| N at position 4 of CDR2α | G |
| E at position 5 of CDR2α | Q |
| R at position 6 of CDR2α | A or Q |
| A at position 1 of CDR3α | M |
| T at position 2 of CDR3α | Y |
| A at position 4 of CDR3α | E or Q |
| N at position 5 of CDR3α | F or Y or W |
| G at position 6 of CDR3α | A or Q |
| K at position 7 of CDR3α | W or R or T or S or M or L |
| I at position 8 of CDR3α | W or V or Y or P, and |
| I at position 9 of CDR3α | N or E or D or Q or V or K or G or M or S | and/or, the TCR β chain variable domain comprises three CDR regions, and the reference sequences of the three CDR regions of the TCR β chain variable domain are listed as follows, CDR1β: SGHDY (SEQ ID NO: 109)
CDR2β: FNNNVP (SEQ ID NO: 110)
CDR3β: ASSLGSNEQY (SEQ ID NO: 111) and contains at least one of the following mutations:

| Residue before mutation | Residue after mutation |
|---|---|
| N at position 3 of CDR2β | H |
| N at position 4 of CDR2β | G |
| V at position 5 of CDR2β | A |
| P at position 6 of CDR2β | V |
| S at position 3 of CDR3β | Q or M |
| L at position 4 of CDR3β | R or K or M, and |
| S at position 6 of CDR3β | A or G or P |

In another preferred embodiment, the number of mutations in the CDR region of the TCR α chain may be 1, 2, 3, 4, 5, 6, 7, 8, 9, 10, 11 or 12.

In another preferred embodiment, the number of mutations in the CDR region of the TCR β chain may be 1, 2, 3, 4, 5, 6, 7, 8, 9, 10 or 11.

In another preferred embodiment, the T cell receptor (TCR) according to the invention comprises a TCR α chain variable domain and a TCR β chain variable domain, and said TCR α chain variable domain comprises CDR1α, CDR2α and CDR3α.

In another preferred embodiment, the CDR3a comprises a sequence:
[3αX1][3αX2]D[3αX3][3αX4][3αX5][3αX6][3αX7][3αX8] (SEQ ID NO: 149), where [3αX1], [3αX2], [3αX3], [3αX4], [3αX5], [3αX6], [3αX7], [3αX8] are independently selected from any natural amino acid residue.

In another preferred embodiment, [3αX1] is A or M.
In another preferred embodiment, [3αX2] is T or Y.
In another preferred embodiment, [3αX3] is A or E or Q.
In another preferred embodiment, [3αX4] is N or F or Y or W.
In another preferred embodiment, [3αX5] is G or A or Q.
In another preferred embodiment, [3αX6] is K or W or R or T or S or M or L.
In another preferred embodiment, [3αX7] is I or W or V or Y or P.
In another preferred embodiment, [3αX8] is I or N or E or D or Q or V or K or G or M or S.
In another preferred embodiment, [3αX1] is A, [3αX2] is T, [3αX3] is A, [3αX4] is N or F or W, [3αX5] is A, [3αX6] is W or R, [3αX7] is W, and [3αX8] is I or N or E or D.

In another preferred embodiment, the CDR3α comprises a sequence selected from the group consisting of:

```
ATDANARWN (SEQ ID NO: 112),
ATDANARWE (SEQ ID NO: 113),
ATDANARWD (SEQ ID NO: 114),
ATDAFAWWI (SEQ ID NO: 115) and
ATDAWARWI (SEQ ID NO: 146).
```

In another preferred embodiment, the CDR1α comprises a sequence:
[1αX1][1αX2][1αX3][1αX4]N (SEQ ID NO: 150), wherein [1αX1], [1αX2], [1αX3], [1αX4] and [1αX5] are independently selected from any natural amino acid residue.

In another preferred embodiment, [1αX1] is T or G.
In another preferred embodiment, [1αX2] is S or W.
In another preferred embodiment, [1αX3] is I or A or V.
In another preferred embodiment, [1αX4] is N or Q.
In another preferred embodiment, [1αX1] is G, [1αX2] is S or W, [1αX3] is I or A or V, and [1αX4] is Q.

In another preferred embodiment, the CDR1α comprises a sequence selected from the group consisting of:

```
GSIQN (SEQ ID NO: 117),
GWAQN (SEQ ID NO: 118),
GWVQN (SEQ ID NO: 119) and
TSINN (SEQ ID NO: 106).
```

In another preferred embodiment, the CDR2α comprises a sequence:
IR [2αX1][2αX2][2αX3][2αX4]E (SEQ ID NO: 151), wherein [2αX1], [2αX2], [2αX3], [2αX4] are independently selected from any natural amino acid residue.

In another preferred embodiment, [2αX1] is S or T.
In another preferred embodiment, [2αX2] is N or G.
In another preferred embodiment, [2αX3] is E or Q.
In another preferred embodiment, [2αX4] is R, A or Q.

In another preferred embodiment, CDR2α comprises a sequence selected from the group consisting of:

```
IRTGEQE (SEQ ID NO: 120),
IRTGQAE (SEQ ID NO: 121)
and
IRSNERE (SEQ ID NO: 107).
```

In another preferred embodiment, the TCR comprises a TCRα chain variable domain and a TCRβ chain variable domain, and the TCRβ chain comprises CDR1β, CDR2β and CDR3β, wherein the CDR1β comprises the sequence: SGHDY (SEQ ID NO: 109).

In another preferred embodiment, CDR2P comprises a sequence:
FN[2βX1][2βX2][2βX3] [2βX4] (SEQ ID NO: 152), wherein each of [2βX1], [2βX2], [2βX3] and [2βX4] is independently selected from any natural amino acid residue.

In another preferred embodiment, [2βX1] is N or H.
In another preferred embodiment, [2βX2] is N or G.
In another preferred embodiment, [2βX3] is V or A.
In another preferred embodiment, [2βX4] is P or V.

In another preferred embodiment, CDR2β comprises a sequence selected from the group consisting of:

```
FNHGAV (SEQ ID NO: 122)
and
FNNNVP (SEQ ID NO: 110).
```

In another preferred embodiment, the CDR3P comprises a sequence: AS[3βX1][3βX2]G[3βX3]NEQY (SEQ ID NO: 153), wherein [3βX1], [3βX2], and [3βX3] are independently selected from any natural amino acid residue.

In another preferred embodiment, [3βX1] is S, Q or M.
In another preferred embodiment, [3βX2] is L, R, K, or M.
In another preferred embodiment, [3βX3] is S, A, G or P.

In another preferred embodiment, the CDR3β comprises a sequence selected from the group consisting of:

```
ASQRGSNEQY (SEQ ID NO: 123),
ASQKGANEQY (SEQ ID NO: 124),
ASQLGSNEQY (SEQ ID NO: 125),
ASQLGANEQY (SEQ ID NO: 126),
ASQLGGNEQY (SEQ ID NO: 127),
ASQLGPNEQY (SEQ ID NO: 128),
ASQRGANEQY (SEQ ID NO: 129),
```

-continued

ASQMGSNEQY (SEQ ID NO: 130),

ASQMGANEQY (SEQ ID NO: 131)
and

ASMLGSNEQY (SEQ ID NO: 132).

In another preferred embodiment, the TCRα chain variable domain of the TCR does not simultaneously comprise the following CDRs:

CDR1α: TSINN (SEQ ID NO: 106); CDR2α: IRSNERE (SEQ ID NO: 107); and CDR3α: ATDANGKII (SEQ ID NO: 108).

In another preferred embodiment, the TCRβ chain variable domain of the TCR does not simultaneously comprise the following CDRs: CDR1β: SGHDY (SEQ ID NO: 109); CDR2β: FNNNVP (SEQ ID NO: 110); and CDR3β: ASSLGSNEQY (SEQ ID NO: 111).

In another preferred embodiment, the mutation occurs in one or more CDR regions of the α chain and/or β chain variable domain.

In another preferred embodiment, the mutation occurs in CDR1, CDR2 and/or CDR3 of the α chain, and/or the mutation occurs in CDR2 and/or CDR3 of the β chain.

In a preferred embodiment of the invention, the affinity of the TCR for SLLMWITQC(SEQ ID NO: 105)-HLA A2 complex is at least 2 times of that of the wild type TCR; preferably at least 5 times; more preferably at least 10 times.

In another preferred embodiment, the affinity of the TCR for SLLMWITQC(SEQ ID NO: 105)-HLA A2 complex is at least 50 times of that of the wild type TCR; preferably, at least 100 times; more preferably, at least 500 times; most preferably, at least 1000 times.

In another preferred embodiment, the affinity of the TCR for SLLMWITQC(SEQ ID NO: 105)-HLA A2 complex is at least $10^4$ times of that of the wild type TCR; preferably, at least $10^5$ times; more preferably, at least $10^6$ times; most preferably, at least $10^7$ times.

In particular, the dissociation equilibrium constant $K_D$ of the TCR to SLLMWITQC(SEQ ID NO: 105)-HLA A2 complex is $\leq 20$ μM;

In another preferred embodiment, the dissociation equilibrium constant of the TCR to SLLMWITQC(SEQ ID NO: 105)-HLA A2 complex is 5 μM$\leq K_D \leq$10 μM; preferably, 0.1 μM$\leq K_D \leq$1 μM; more preferably, 1 nM$\leq K_D \leq$100 nM;

In another preferred embodiment, the dissociation equilibrium constant of the TCR to SLLMWITQC(SEQ ID NO: 105)-HLA A2 complex is 100 pM$\leq K_D \leq$1000 pM; preferably, 10 pM$\leq K_D \leq$100 pM; more preferably, 1 pM$\leq K_D \leq$10 pM.

In another referred embodiment the TCR has a CDR selected from the group consisting of:

| TCR No. | CDR1α | CDR2α | CDR3α | CDR1β | CDR2β | CDR3β |
|---|---|---|---|---|---|---|
| 1 | TSINN (SEQ ID NO: 106) | IRSNERE (SEQ ID NO: 107) | ATDAFAWWI (SEQ ID NO: 115) | SGHDY (SEQ ID NO: 109) | FNNNVP (SEQ ID NO: 110) | ASSLGSNEQY (SEQ ID NO: 111) |
| 2 | GWAQN (SEQ ID NO: 118) | IRTGEQE (SEQ ID NO: 120) | ATDANARWN (SEQ ID NO: 112) | SGHDY (SEQ ID NO: 109) | FNHGAV (SEQ ID NO: 122) | ASSLGSNEQY (SEQ ID NO: 111) |
| 3 | GSIQN (SEQ ID NO: 117) | IRTGEQE (SEQ ID NO: 120) | ATDANARWE (SEQ ID NO: 113) | SGHDY (SEQ ID NO: 109) | FNHGAV (SEQ ID NO: 122) | ASSLGSNEQY (SEQ ID NO: 111) |
| 4 | GSIQN (SEQ ID NO: 117) | IRTGEQE (SEQ ID NO: 120) | ATDANARWE (SEQ ID NO: 113) | SGHDY (SEQ ID NO: 109) | FNHGAV (SEQ ID NO: 122) | ASQRGSNEQY (SEQ ID NO: 123) |
| 5 | GSIQN (SEQ ID NO: 117) | IRTGEQE (SEQ ID NO: 120) | ATDANARWE (SEQ ID NO: 113) | SGHDY (SEQ ID NO: 109) | FNHGAV (SEQ ID NO: 122) | ASQKGANEQY (SEQ ID NO: 124) |
| 6 | GSIQN (SEQ ID NO: 117) | IRTGEQE (SEQ ID NO: 120) | ATDANARWD (SEQ ID NO: 114) | SGHDY (SEQ ID NO: 109) | FNHGAV (SEQ ID NO: 122) | ASQLGSNEQY (SEQ ID NO: 125) |
| 7 | GWAQN (SEQ ID NO: 118) | IRSNERE (SEQ ID NO: 107) | ATDANARWN (SEQ ID NO: 112) | SGHDY (SEQ ID NO: 109) | FNHGAV (SEQ ID NO: 122) | ASQLGSNEQY (SEQ ID NO: 125) |
| 8 | GWVQN (SEQ ID NO: 119) | IRTGEQE (SEQ ID NO: 120) | ATDANARWD (SEQ ID NO: 114) | SGHDY (SEQ ID NO: 109) | FNHGAV (SEQ ID NO: 122) | ASSLGSNEQY (SEQ ID NO: 111) |
| 9 | GSIQN (SEQ ID NO: 117) | IRSNERE (SEQ ID NO: 107) | ATDANARWD (SEQ ID NO: 114) | SGHDY (SEQ ID NO: 109) | FNHGAV (SEQ ID NO: 122) | ASQLGANEQY (SEQ ID NO: 126) |
| 10 | GWAQN (SEQ ID NO: 118) | IRSNERE (SEQ ID NO: 107) | ATDANARWD (SEQ ID NO: 114) | SGHDY (SEQ ID NO: 109) | FNHGAV (SEQ ID NO: 122) | ASQLGSNEQY (SEQ ID NO: 125) |
| 11 | GSIQN (SEQ ID NO: 117) | IRSNERE (SEQ ID NO: 107) | ATDANARWE (SEQ ID NO: 113) | SGHDY (SEQ ID NO: 109) | FNHGAV (SEQ ID NO: 122) | ASQKGANEQY (SEQ ID NO: 124) |

-continued

| TCR No. | CDR1α | CDR2α | CDR3α | CDR1β | CDR2β | CDR3β |
|---|---|---|---|---|---|---|
| 12 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQLGGNEQY (SEQ ID NO: 127) |
| 13 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQKGANEQY (SEQ ID NO: 124) |
| 14 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQLGPNEQY (SEQ ID NO: 128) |
| 15 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQRGANEQY (SEQ ID NO: 129) |
| 16 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQMGSNEQY (SEQ ID NO: 130) |
| 17 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQLGSNEQY (SEQ ID NO: 125) |
| 18 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQLGANEQY (SEQ ID NO: 126) |
| 19 | TSINN (SEQ ID NO: 106) | IRSNERE (SEQ ID NO: 107) | MYDENGKII (SEQ ID NO: 133) | SGHDY (SEQ ID NO: 109) | FNNNVP (SEQ ID NO: 110) | ASSLGSNEQY (SEQ ID NO: 111) |
| 20 | TSINN (SEQID NO: 106) | IRSNERE (SEQ ID NO: 107) | MYDQNGKII (SEQ ID NO: 134) | SGHDY (SEQ ID NO: 109) | FNNNVP (SEQ ID NO: 110) | ASSLGSNEQY (SEQ ID NO: 111) |
| 21 | TSINN (SEQ ID NO: 106) | IRSNERE (SEQ ID NO: 107) | ATDAYGTVQ (SEQ ID NO: 135) | SGHDY (SEQ ID NO: 109) | FNNNVP (SEQ ID NO: 110) | ASSLGSNEQY (SEQ ID NO: 111) |
| 22 | TSINN (SEQ ID NO: 106) | IRSNERE (SEQ ID NO: 107) | ATDANGTVQ (SEQ ID NO: 136) | SGHDY (SEQ ID NO: 109) | FNNNVP (SEQ ID NO: 110) | ASSLGSNEQY (SEQ ID NO: 111) |
| 23 | TSINN (SEQ ID NO: 106) | IRSNERE (SEQ ID NO: 107) | ATDANGSVQ (SEQ ID NO: 137) | SGHDY (SEQ ID NO: 109) | FNNNVP (SEQ ID NO: 110) | ASSLGSNEQY (SEQ ID NO: 111) |
| 24 | TSINN (SEQ ID NO: 106) | IRSNERE (SEQ ID NO: 107) | ATDAYGRYI (SEQ ID NO: 138) | SGHDY (SEQ ID NO: 109) | FNNNVP (SEQ ID NO: 110) | ASSLGSNEQY (SEQ ID NO: 111) |
| 25 | TSINN (SEQ ID NO: 106) | IRSNERE (SEQ ID NO: 107) | ATDANQMWK (SEQ ID NO: 139) | SGHDY (SEQ ID NO: 109) | FNNNVP (SEQ ID NO: 110) | ASSLGSNEQY (SEQ ID NO: 111) |
| 26 | TSINN (SEQ ID NO: 106) | IRSNERE (SEQ ID NO: 107) | ATDAYGLPI (SEQ ID NO: 140) | SGHDY (SEQ ID NO: 109) | FNNNVP (SEQ ID NO: 110) | ASSLGSNEQY (SEQ ID NO: 111) |
| 27 | TSINN (SEQ ID NO: 106) | IRSNERE (SEQ ID NO: 107) | ATDANGLPV (SEQ ID NO: 141) | SGHDY (SEQ ID NO: 109) | FNNNVP (SEQ ID NO: 110) | ASSLGSNEQY (SEQ ID NO: 111) |
| 28 | TSINN (SEQ ID NO: 106) | IRSNERE (SEQ ID NO: 107) | ATDANGRWE (SEQ ID NO: 142) | SGHDY (SEQ ID NO: 109) | FNNNVP (SEQ ID NO: 110) | ASSLGSNEQY (SEQ ID NO: 111) |
| 29 | TSINN (SEQ ID NO: 106) | IRSNERE (SEQ ID NO: 107) | ATDANGTVG (SEQ ID NO: 143) | SGHDY (SEQ ID NO: 109) | FNNNVP (SEQ ID NO: 110) | ASSLGSNEQY (SEQ ID NO: 111) |
| 30 | TSINN (SEQ ID NO: 106) | IRSNERE (SEQ ID NO: 107) | ATDANGRWM (SEQ ID NO: 144) | SGHDY (SEQ ID NO: 109) | FNNNVP (SEQ ID NO: 110) | ASSLGSNEQY (SEQ ID NO: 111) |

-continued

| TCR No. | CDR1α | CDR2α | CDR3α | CDR1β | CDR2β | CDR3β |
|---|---|---|---|---|---|---|
| 31 | TSINN (SEQ ID NO: 106) | IRSNERE (SEQ ID NO: 107) | ATDANGLWS (SEQ ID NO: 145) | SGHDY (SEQ ID NO: 109) | FNNNVP (SEQ ID NO: 110) | ASSLGSNEQY (SEQ ID NO: 111) |
| 32 | GWAQN (SEQ ID NO: 118) | IRTGEQE (SEQ ID NO: 120) | ATDANARWD (SEQ ID NO: 114) | SGHDY (SEQ ID NO: 109) | FNNNVP (SEQ ID NO: 110) | ASSLGSNEQY (SEQ ID NO: 111) |
| 33 | GWAQN (SEQ ID NO: 118) | IRTGQAE (SEQ ID NO: 121) | ATDANARWE (SEQ ID NO: 113) | SGHDY (SEQ ID NO: 109) | FNNNVP (SEQ ID NO: 110) | ASSLGSNEQY (SEQ ID NO: 111) |
| 34 | GSIQN (SEQ ID NO: 117) | IRSNERE (SEQ ID NO: 107) | ATDAFAWWI (SEQ ID NO: 115) | SGHDY (SEQ ID NO: 109) | FNNNVP (SEQ ID NO: 110) | ASSLGSNEQY (SEQ ID NO: 111) |
| 35 | GWVQN (SEQ ID NO: 119) | IRTGEQE (SEQ ID NO: 120) | ATDANARWN (SEQ ID NO: 112) | SGHDY (SEQ ID NO: 109) | FNNNVP (SEQ ID NO: 110) | ASSLGSNEQY (SEQ ID NO: 111) |
| 36 | GWAQN (SEQ ID NO: 118) | IRTGEQE (SEQ ID NO: 120) | ATDANARWN (SEQ ID NO: 112) | SGHDY (SEQ ID NO: 109) | FNNNVP (SEQ ID NO: 110) | ASSLGSNEQY (SEQ ID NO: 111) |
| 37 | GWVQN (SEQ ID NO: 119) | IRTGEQE (SEQ ID NO: 120) | ATDANARWD (SEQ ID NO: 114) | SGHDY (SEQ ID NO: 109) | FNNNVP (SEQ ID NO: 110) | ASSLGSNEQY (SEQ ID NO: 111) |
| 38 | GSIQN (SEQ ID NO: 117) | IRTGEQE (SEQ ID NO: 120) | ATDAWARWI (SEQ ID NO: 146) | SGHDY (SEQ ID NO: 109) | FNNNVP (SEQ ID NO: 110) | ASSLGSNEQY (SEQ ID NO: 111) |
| 39 | GWVQN (SEQ ID NO: 119) | IRTGQAE (SEQ ID NO: 121) | ATDANARWE (SEQ ID NO: 113) | SGHDY (SEQ ID NO: 109) | FNNNVP (SEQ ID NO: 110) | ASSLGSNEQY (SEQ ID NO: 111) |
| 40 | GSIQN (SEQ ID NO: 117) | IRTGEQE (SEQ ID NO: 120) | ATDANARWN (SEQ ID NO: 112) | SGHDY (SEQ ID NO: 109) | FNNNVP (SEQ ID NO: 110) | ASSLGSNEQY (SEQ ID NO: 111) |
| 41 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQMGSNEQY (SEQ ID NO: 130) |
| 42 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQRGSNEQY (SEQ ID NO: 123) |
| 43 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQMGANEQY (SEQ ID NO: 131) |
| 44 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASMLGSNEQY (SEQ ID NO: 132) |

In another preferred embodiment, the TCR is soluble.

In another preferred embodiment, the TCR is an αβ heterodimeric TCR or a single chain TCR.

In another preferred embodiment, the TCR of the present invention is an αβ heterodimeric TCR, and the α chain variable domain of the TCR comprises an amino acid sequence having at least 85%, preferably at least 90%; more preferably, at least 92%; most preferably, at least 94% (e.g., may be at least 88%, 89%, 90%, 91%, 92%, 93%, 94%, 95%, 96%, 97%, 98%, 99% of sequence homology) of sequence homology with the amino acid sequence shown in SEQ ID NO: 1; and/or the β chain variable domain of the TCR comprises an amino acid sequence having at least 90%, preferably at least 92%; more preferably at least 94%; most preferably at least 97% (e.g., may be at least 91%, 92%, 93%, 94%, 95%, 96%, 97%, 98%, 99% of sequence homology) of sequence homology with the amino acid sequence shown in SEQ ID NO: 2.

In another preferred embodiment, the TCR comprises (i) all or part of the TCR α chain other than its transmembrane domain, and (ii) all or part of the TCR β chain other than its transmembrane domain, wherein both of (i) and (ii) comprise the variable domain and at least a portion of the constant domain of the TCR chain.

In another preferred embodiment, the TCR is an αβ heterodimeric TCR, and an artificial interchain disulfide bond is contained between the α chain variable region and the β chain constant region of the TCR.

In another preferred embodiment, cysteine residues forming an artificial interchain disulfide bond between the α chain variable region and the β chain constant region of the TCR are substituted for one or more groups of amino acids selected from the following:

amino acid at position 46 of TRAV and amino acid at position 60 of TRBC1*01 or TRBC2*01 exon 1;
amino acid at position 47 of TRAV and amino acid at position 61 of TRBC1*01 or TRBC2*01 exon 1;
amino acid at position 46 of TRAV and amino acid at position 61 of TRBC1*01 or TRBC2*01 exon 1; or
amino acid at position 47 of TRAV and amino acid at position 60 of TRBC1*01 or TRBC2*01 exon 1.

In another preferred embodiment, the TCR comprising an artificial interchain disulfide bond between α chain variable region and β chain constant region comprises α chain variable domain and β chain variable domain as well as all or part of β chain constant domains other than its transmembrane domain, however it does not comprise α chain constant domain, and α chain variable domain and β chain of the TCR form a heterodimer.

In another preferred embodiment, the TCR comprising an artificial interchain disulfide bond between α chain variable region and β chain constant region comprises (i) all or part of TCR α chain other than its transmembrane domain, and (ii) all or part of TCR β chain other than its transmembrane domain, wherein both of (i) and (ii) comprise the variable domain and at least a portion of constant domains of the TCR chain.

In another preferred embodiment, the TCR is an αβ heterodimeric TCR comprising (i) all or part of TCR α chain other than its transmembrane domain, and (ii) all or part of TCR β chain other than its transmembrane domain, wherein both of (i) and (ii) comprise the variable domain and at least a portion of the constant domain of the TCR chain, and an artificial interchain disulfide bond is contained between α chain constant region and β chain constant region.

In another preferred embodiment, cysteine residues forming an artificial interchain disulfide bond between the TCR α chain constant region and β chain constant region are substituted for one or more groups of amino acids selected from the following:

Thr48 of TRAC*01 exon 1 and Ser57 of TRBC1*01 or TRBC2*01 exon 1;
Thr45 of TRAC*01 exon 1 and Ser77 of TRBC1*01 or TRBC2*01 exon 1;
Tyr10 of TRAC*01 exon 1 and Ser17 of TRBC1*01 or TRBC2*01 exon 1;
Thr45 of TRAC*01 exon 1 and Asp59 of TRBC1*01 or TRBC2*01 exon 1;
Ser15 of TRAC*01 exon 1 and Glu15 of TRBC1*01 or TRBC2*01 exon 1;
Arg53 of TRAC*01 exon 1 and Ser54 of TRBC1*01 or TRBC2*01 exon 1;
Pro89 of TRAC*01 exon 1 and Ala19 of TRBC1*01 or TRBC2*01 exon 1; and
Tyr10 of TRAC*01 exon 1 and Glu20 of TRBC1*01 or TRBC2*01 exon 1.

In another preferred embodiment, the TCR is a single chain TCR.

In another preferred embodiment, the TCR is a single-chain TCR consisting of an α chain variable domain and a β chain variable domain, and the α chain variable domain and the β chain variable domain are connected by a flexible short peptide sequence (linker).

In another preferred embodiment, the hydrophobic core of the TCR α chain variable domain and/or β chain variable domain is mutated.

In another preferred embodiment, the TCR, in which the hydrophobic core is mutated, is a single-chain TCR consisting of an α variable domain and a β variable domain, and the α variable domain and the β variable domain are connected by a flexible short peptide sequence (linker).

In another preferred embodiment, based on the number shown in SEQ ID NO: 1, one or more of the amino acid residues 19A (i.e., position 19 of the α chain variable region listed in IMGT), 21M (i.e., position 21 of the α chain variable region listed in IMGT) and 79S (i.e., position 94 of the α chain variable region listed in IMGT) in the hydrophobic core of α chain variable domain of the TCR of the present invention are mutated, and/or based on the number shown in SEQ ID NO: 2, one or more of the amino acid residues 13T (i.e., position 13 of the β chain variable region listed in IMGT), 82S (i.e., position 94 of the β chain variable region listed in IMGT) in the hydrophobic core of β chain variable domain of the TCR are mutated.

In another preferred embodiment, based on the number shown in SEQ ID NO: 1, the hydrophobic core of α chain variable domain of the present invention comprises one or more of amino acid residues 19V, 21I and 79V and/or, based on the number shown in SEQ ID NO: 2, the hydrophobic core of β variable domain of TCR comprises one or more of amino acid residues 13V and 82V. More specifically, the mutated form of hydrophobic core in the TCRα variable domain comprises one or more of A19V, M21I and S79V; and the mutated form of hydrophobic core in the TCRβ variable domain comprises one or more of T13V and S82V.

In another preferred embodiment, the TCR of the present invention is a single-chain TCR, and the α chain variable domain of the TCR comprises an amino acid sequence having at least 85%, preferably at least 90%; more preferably, at least 92%; most preferably at least 94% (e.g., may be at least 88%, 89%, 90%, 91%, 92%, 93%, 94%, 95%, 96%, 97%, 98%, 99% of sequence homology) of sequence homology with the amino acid sequence shown in SEQ ID NO: 3; and/or the β chain variable domain of the TCR comprises an amino acid sequence having at least 90%, preferably at least 92%; more preferably, at least 94%; most preferably at least 97% (e.g., may be at least 91%, 92%, 93%, 94%, 95%, 96%, 97%, 98%, 99% of sequence homology) of sequence homology with the amino acid sequence shown in SEQ ID NO: 4.

In another preferred embodiment, the amino acid sequence of the α chain variable domain of the TCR is selected from the group consisting of: SEQ ID NOs: 9-37 and 58-86; and/or the amino acid sequence of the β chain variable domain of the TCR is selected from the group consisting of: SEQ ID NOs: 38-53 and 87-102.

In another preferred embodiment, the TCR is selected from the group consisting of:

| TCR Number | Sequence of α chain variable domain SEQ ID NO: | Sequence of β chain variable domain SEQ ID NO: |
| --- | --- | --- |
| s-1 | 9 | 4 |
| s-2 | 10 | 38 |
| s-3 | 11 | 38 |
| s-4 | 11 | 39 |
| s-5 | 11 | 40 |
| s-6 | 12 | 41 |
| s-7 | 13 | 41 |
| s-8 | 14 | 38 |
| s-9 | 15 | 42 |
| s-10 | 16 | 41 |
| s-11 | 17 | 40 |

| TCR Number | Sequence of α chain variable domain SEQ ID NO: | Sequence of β chain variable domain SEQ ID NO: |
| --- | --- | --- |
| s-12 | 3 | 43 |
| s-13 | 3 | 44 |
| s-14 | 3 | 45 |
| s-15 | 3 | 46 |
| s-16 | 3 | 47 |
| s-17 | 3 | 48 |
| s-18 | 3 | 49 |
| s-19 | 18 | 4 |
| s-20 | 19 | 4 |
| s-21 | 20 | 4 |
| s-22 | 21 | 4 |
| s-23 | 22 | 4 |
| s-24 | 23 | 4 |
| s-25 | 24 | 4 |
| s-26 | 25 | 4 |
| s-27 | 26 | 4 |
| s-28 | 27 | 4 |
| s-29 | 28 | 4 |
| s-30 | 29 | 4 |
| s-31 | 30 | 4 |
| s-32 | 31 | 4 |
| s-33 | 32 | 4 |
| s-34 | 33 | 4 |
| s-35 | 34 | 4 |
| s-36 | 10 | 4 |
| s-37 | 14 | 4 |
| s-38 | 35 | 4 |
| s-39 | 36 | 4 |
| s-40 | 37 | 4 |
| s-41 | 3 | 50 |
| s-42 | 3 | 51 |
| s-43 | 3 | 52 |
| s-44 | 3 | 53 |

In another preferred embodiment, the TCR is selected from the group consisting of:

| TCR number | Sequence of α chain variable domain SEQ ID NO: | Sequence of β chain variable domain SEQ ID NO: |
| --- | --- | --- |
| 1 | 58 | 2 |
| 2 | 59 | 87 |
| 3 | 60 | 87 |
| 4 | 60 | 88 |
| 5 | 60 | 89 |
| 6 | 61 | 90 |
| 7 | 62 | 90 |
| 8 | 63 | 87 |
| 9 | 64 | 91 |
| 10 | 65 | 90 |
| 11 | 66 | 89 |
| 12 | 1 | 92 |
| 13 | 1 | 93 |
| 14 | 1 | 94 |
| 15 | 1 | 95 |
| 16 | 1 | 96 |
| 17 | 1 | 97 |
| 18 | 1 | 98 |
| 19 | 67 | 2 |
| 20 | 68 | 2 |
| 21 | 69 | 2 |
| 22 | 70 | 2 |
| 23 | 71 | 2 |
| 24 | 72 | 2 |
| 25 | 73 | 2 |
| 26 | 74 | 2 |
| 27 | 75 | 2 |
| 28 | 76 | 2 |
| 29 | 77 | 2 |
| 30 | 78 | 2 |
| 31 | 79 | 2 |
| 32 | 80 | 2 |
| 33 | 81 | 2 |
| 34 | 82 | 2 |
| 35 | 83 | 2 |
| 36 | 59 | 2 |
| 37 | 63 | 2 |
| 38 | 84 | 2 |
| 39 | 85 | 2 |
| 40 | 86 | 2 |
| 41 | 1 | 99 |
| 42 | 1 | 100 |
| 43 | 1 | 101 |
| 44 | 1 | 102. |

In another preferred embodiment, a conjugate binds to the α chain and/or β chain of the TCR at C- or N-terminus.

In another preferred embodiment, the conjugate that binds to the TCR is a detectable label, a therapeutic agent, a PK modified moiety, or a combination of any of these.

In another preferred embodiment, the therapeutic agent that binds to the TCR is an anti-CD3 antibody linked to the α or β chain of the TCR at C- or N-terminus.

In a preferred embodiment of the invention, the T cell receptor (TCR) has the activity of binding to SLLMWITQC (SEQ ID NO: 105)-HLA A2 complex and comprises a TCR α chain variable domain and a TCR β chain variable domain, there is a mutation in the α chain variable domain of the TCR as shown in SEQ ID NO: 1, and the mutated amino acid residue site includes one or more of 27T, 28S, 29I, 30N, 51S, 52N, 53E, 54R, 90A, 91T, 93A, 94N, 95G, 96K, 97I and 98I, wherein the amino acid residue is numbered as shown in SEQ ID NO: 56 or 1; and/or there is a mutation in the β chain variable domain of the TCR as shown in SEQ ID NO: 2, and the mutated amino acid residue site includes one or more of 51N, 52N, 53V, 54P, 95S, 96L and 98S, wherein the amino acid residue is numbered as shown in SEQ ID NO: 57 or 2.

Preferably, upon mutation, the TCR α chain variable domain comprises one or more amino acid residues selected from the group consisting of: 27G, 28W, 29A or 29V, 30Q, 51T, 52G, 53Q, 54Q or 54A, 90M, 91Y, 93E or 93Q, 94F or 94Y or 94W, 95A or 95Q, 96W or 96R or 96T or 96S or 96M or 96L, 97W or 97V or 97Y or 97P, and 98E or 98N or 98D or 98Q or 98K or 98V or 98G or 98M or 98S, wherein the amino acid residue is numbered as shown in SEQ ID NO: 1; and/or upon mutation, the TCR β chain variable domain comprises one or more amino acid residues selected from the group consisting of: 51H, 52G, 53A, 54V, 95Q or 95M, 96R or 96K or 96M, and 98A or 98G or 98P, wherein the amino acid residue is numbered as shown in SEQ ID NO: 2.

In a second aspect of the invention, a multivalent TCR complex comprising at least two TCR molecules is provided, and at least one TCR molecule is the TCR of the first aspect of the invention.

In a third aspect of the invention, a nucleic acid molecule is provided, comprising a nucleic acid sequence encoding the TCR molecule of the first aspect of the invention or the multivalent TCR complex of the second aspect of the invention, or a complement sequence thereof; In a fourth aspect of the invention, a vector is provided, comprising the nucleic acid molecule of the third aspect of the invention.

In a fifth aspect of the present invention, a host cell is provided, comprising the vector of the fourth aspect of the present invention or having the exogenous nucleic acid molecule of the third aspect of the present invention integrated into its genome.

In a sixth aspect of the invention, an isolated cell is provided, expressing the TCR of the first aspect of the invention.

In a seventh aspect of the invention, a pharmaceutical composition is provided, comprising a pharmaceutically acceptable carrier, and a TCR of the first aspect of the invention, or a TCR complex of the second aspect of the invention, or the cell of the sixth aspect of the invention.

In an eighth aspect of the present invention, a method for treating a disease is provided, comprising administering an appropriate amount of the TCR of the first aspect of the present invention, or the TCR complex of the second aspect of the present invention, or the cell of the sixth aspect of the invention, or the pharmaceutical composition of the seventh aspect of the invention to a subject in need thereof.

In a ninth aspect of the invention, use of the TCR of the first aspect of the invention, or the TCR complex of the second aspect of the invention, or the cell of the sixth aspect of the invention is provided for preparing a medicament for treating tumor.

In a tenth aspect of the invention, a method for preparing the T cell receptor of the first aspect of the invention is provided, comprising the steps of
(i) culturing the host cell of the fifth aspect of the invention to express the T cell receptor of the first aspect of the invention;
(ii) isolating or purifying the T cell receptor.

It is to be understood that within the scope of the present invention, the various technical features of the present invention and the technical features specifically described hereinafter (as in the embodiments) may be combined with each other to constitute a new or preferred technical solution, which will not be repeated herein one by one.

DESCRIPTION OF DRAWINGS

FIG. 1a and FIG. 1b show the amino acid sequences of wild-type TCR α and β chain variable domain that are capable of specifically binding to SLLMWITQC(SEQ ID NO: 105)-HLA A2 complex, respectively.

FIG. 2a and FIG. 2b show the amino acid sequences of the α variable domain and the β chain variable domain of the single-chain template TCR constructed in the present invention, respectively.

FIG. 3a and FIG. 3b show the DNA sequences of the α variable domain and the β chain variable domain of the single-chain template TCR constructed in the present invention, respectively.

FIG. 4a and FIG. 4b are the amino acid sequence and nucleotide sequence of the linking short peptide (linker) of the single-chain template TCR constructed in the present invention, respectively.

FIGS. 5(1)-(29) show the amino acid sequences of α-chain variable domain of single-chain TCRs with high affinity for SLLMWITQC(SEQ ID NO: 105)-HLA A2 complex, respectively, and the mutated residues are underlined.

FIGS. 6(1)-(16) show the amino acid sequences of β-chain variable domain of single-chain TCRs with high affinity for SLLMWITQC(SEQ ID NO: 105)-HLA A2 complex, respectively, and the mutated residues are underlined.

FIG. 7a and FIG. 7b show the amino acid sequence and DNA sequence of the single-chain template TCR constructed in the present invention, respectively.

FIGS. 8a and 8b show the amino acid sequences of the reference TCR α and β chains in the present invention, respectively.

FIGS. 9(1)-(29) show the amino acid sequences of α-chain variable domain of a heterodimeric TCR with high affinity for SLLMWITQC(SEQ ID NO: 105)-HLA A2 complex, respectively, and the mutated residues are underlined.

FIGS. 10(1)-(16) show the amino acid sequences of β-chain variable domain of a heterodimeric TCR with high affinity for SLLMWITQC(SEQ ID NO: 105)-HLA A2 complex, respectively, and the mutated residues are underlined.

FIG. 11a and FIG. 11b show the amino acid sequences of wild-type TCR α and β chain that are capable of specifically binding to SLLMWITQC(SEQ ID NO: 105)-HLA A2 complex, respectively.

MODES FOR CARRYING OUT THE INVENTION

Figure 12:
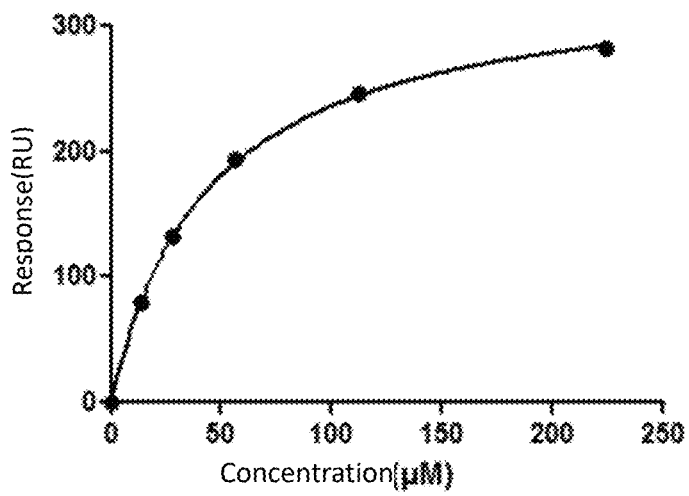
FIG. 12 is a binding curve of a reference TCR, i.e., wild-type TCR with SLLMWITQC(SEQ ID NO: 105)-HLA A2 complex.

Through extensive and intensive research, the present inventors obtained a high affinity T cell receptor (TCR) recognizing SLLMWITQC(SEQ ID NO: 105) short peptide (derived from NY-ESO-1 protein) which is presented in a form of peptide-HLA A2 complexe. The high affinity TCR has three CDR regions in its α chain variable domain
CDR1α: TSINN (SEQ ID NO: 106)
CDR2α: IRSNERE (SEQ ID NO: 107)
CDR3α: a mutation in ATDANGKII (SEQ ID NO: 108); and/or three CDR regions in its β-chain variable domain
CDR1β: SGHDY (SEQ ID NO: 109)
CDR2β: FNNNVP (SEQ ID NO: 110)
CDR3β: a mutation in ASSLGSNEQY (SEQ ID NO: 111); and, after mutation, the affinity and/or binding half-life of the TCR of the present invention for the above SLLMWITQC(SEQ ID NO: 105)-HLA A2 complex is at least 2-fold greater than that of the wild-type TCR.

Before the present invention is described, it is to be understood that the invention is not limited to the specific methods and experimental conditions described, as such methods and conditions may vary. It is also understood that the terminology used herein is for the purpose of describing particular embodiments, and is not intended to be limiting, and the scope of the present invention shall be only limited by the attached claim set.

All technical and scientific terms used herein have the same meaning as commonly understood by a skilled person in the art to which this invention belongs, unless otherwise defined.

Although any methods and materials similar or equivalent to those described in the present invention can be used in the practice or testing of the present invention, the preferred methods and materials are exemplified herein.

Term

T Cell Receptor (TCR)

International Immunogenetics Information System (IMGT) can be used to describe a TCR. A native αβ heterodimeric TCR has an α chain and a β chain. Generally speaking, each chain comprises a variable region, a junction region and a constant region, and the β chain typically also contains a short hypervariable region between the variable region and junction region, which however is often considered as a part of the junction region. The TCR junction region is determined by the unique TRAJ and TRBJ of IMGT, and the constant region of a TCR is determined by TACT and TRBC of IMGT.

Each variable region comprises three CDRs (complementarity determining regions), CDR1, CDR2 and CDR3, which are chimeric in the framework sequence. In IMGT nomenclature, the different numbers of TRAV and TRBV refer to different Vα types and Vβ types, respectively. In IMGT system, there are following symbols for α chain constant domain: TRAC*01, where "TR" represents T cell receptor gene; "A" represents α chain gene; C represents the constant region; "*01" represents allele gene 1. There are following symbols for β-chain constant domain: TRBC1*01 or TRBC2*01, where "TR" represents T cell receptor gene; "B" represents β-chain gene; C represents constant region; "*01" represents allele gene 1. The constant region of α chain is uniquely defined, and in the form of β chain, there are two possible constant region genes "C1" and "C2". A skilled person in the art can obtain constant region gene sequences of TCR α and β chains through the disclosed IMGT database.

The α and β chains of TCR are generally considered as having two "domains" respectively, i.e., variable domain and constant domain. The variable domain consists of a connected variable region and a connection region. Therefore, in the specification and claims of the present application, "TCR α chain variable domain" refers to a connected TRAV and TRAJ region, and likewise, "TCR β chain variable domain" refers to a connected TRBV and TRBD/TRBJ region. The three CDRs of TCR α chain variable domain are CDR1α, CDR2α and CDR3α, respectively; and the three CDRs of TCR β chain variable domain are CDR1β, CDR2β and CDR3β, respectively. The framework sequences of TCR variable domains of the invention may be of murine or human origin, preferably of human origin. The constant domain of TCR comprises an intracellular portion, transmembrane region, and extracellular portion. To obtain a soluble TCR for determining the affinity between TCR and SLLMWITQC(SEQ ID NO: 105)-HLA A2 complex, TCR of the invention preferably does not comprise a transmembrane region. More preferably, the amino acid sequence of the TCR of the present invention refers to the extracellular amino acid sequence of the TCR.

The α chain amino acid sequence and β chain amino acid sequence of the "wild type TCR" described in the present invention are SEQ ID NO: 103 and SEQ ID NO: 104, respectively, as shown in FIGS. 11a and 11b. In the present invention, the α chain amino acid sequence and β chain amino acid sequence of the "reference TCR" are SEQ ID NO: 56 and SEQ ID NO: 57, respectively, as shown in FIGS. 8a and 8b. In the present invention, the α and β chain variable domain amino acid sequences of the wild type TCR capable of binding to SLLMWITQC(SEQ ID NO: 105)-HLA A2 complex are SEQ ID NO: 1 and SEQ ID NO: 2, respectively, as shown in FIGS. 1a and 1b. In the present invention, the terms "polypeptide of the present invention", "TCR of the present invention" and "T cell receptor of the present invention" are used interchangeably.

In a preferred embodiment of the invention, the T cell receptor (TCR) according to the invention comprises a TCR α chain variable domain and a TCR β chain variable domain, and said TCR α chain variable domain comprising CDR1α, CDR2α and CDR3α.

In another preferred embodiment, the CDR3α comprises a sequence:

[3αX1][3αX2]D[3αX3][3αX4][3αX5][3αX6][3αX7][3αX8] (SEQ ID NO: 149), where [3αX1], [3αX2], [3αX3], [3αX4], [3αX5], [3αX6], [3αX7], [3αX8] are independently selected from any natural amino acid residues.

In another preferred embodiment, the [3αX1] is A or M.

In another preferred embodiment, the [3αX2] is T or Y.

In another preferred embodiment, the [3αX3] is A or E or Q.

In another preferred embodiment, the [3αX4] is N or F or Y or W.

In another preferred embodiment, the [3αX5] is G or A or Q.

In another preferred embodiment, the [3αX6] is K or W or R or T or S or M or L.

In another preferred embodiment, the [3αX7] is I or W or V or Y or P.

In another preferred embodiment, the [3αX8] is I or N or E or D or Q or V or K or G or M or S.

In another preferred embodiment, the [3αX1] is A, [3αX2] is T, [3αX3] is A, [3αX4] is N or F or W, [3αX5] is A, [3αX6] is W or R, [3αX7] is W and [3αX8] is I or N or E or D.

In another preferred embodiment, the CDR3α comprises a sequence selected from the group consisting of:

```
ATDANARWN (SEQ ID NO: 112),
ATDANARWE (SEQ ID NO: 113),
ATDANARWD (SEQ ID NO: 114),
ATDAFAWWI (SEQ ID NO: 115)
and
ATDAWARWI (SEQ ID NO: 146).
```

In another preferred embodiment, the CDR1α comprises a sequence:

[1αX1][1αX2][1αX3][1αX4]N (SEQ ID NO: 150), wherein [1αX1], [1αX2], [1αX3], [1αX4], [1αX5] are independently selected from any natural amino acid residue.

In another preferred embodiment, the [1αX1] is T or G.

In another preferred embodiment, the [1αX2] is S or W.

In another preferred embodiment, the [1αX3] is I or A or V.

In another preferred embodiment, the [1αX4] is N or Q.

In another preferred embodiment, the [1αX1] is G, [1αX2] is S or W, [1αX3] is I or A or V and [1αX4] is Q.

In another preferred embodiment, the CDR1α comprises a sequence selected from the group consisting of:

```
GSIQN (SEQ ID NO: 117),
GWAQN (SEQ ID NO: 118),
GWVQN (SEQ ID NO: 119)
and
TSINN (SEQ ID NO: 106).
```

In another preferred embodiment, the CDR2α comprises a sequence:

IR [2αX1][2αX2][2αX3][2αX4]E (SEQ ID NO: 151), wherein [2αX1], [2αX2], [2αX3], [2αX4] are independently selected from any natural amino acid residue.

In another preferred embodiment, the [2αX1] is S or T.
In another preferred embodiment, the [2αX2] is N or G.
In another preferred embodiment, the [2αX3] is E or Q.
In another preferred embodiment, the [2αX4] is R, A or Q.

In another preferred embodiment, the CDR2α comprises a sequence selected from the group consisting of:

```
IRTGEQE (SEQ ID NO: 120),

IRTGQAE (SEQ ID NO: 121)
and

IRSNERE (SEQ ID NO: 107).
```

In a preferred embodiment of the present invention, the TCR comprises a TCRα chain variable domain and a TCRβ chain variable domain, and the TCRβ chain variable domain comprises CDR1β, CDR2β and CDR3β, wherein the CDR1β comprises a sequence: SGHDY (SEQ ID NO: 109).

In another preferred embodiment, the CDR2β comprises a sequence:

FN[2βX1][2βX2][2βX3][2βX4] (SEQ ID NO: 152), wherein each of [2βX1], [2βX2], [2βX3] and [2βX4] is independently selected from any natural amino acid residue.

In another preferred embodiment, the [2βX1] is N or H.
In another preferred embodiment, the [2βX2] is N or G.
In another preferred embodiment, the [2βX3] is V or A.
In another preferred embodiment, the [2βX4] is P or V.

In another preferred embodiment, the CDR2β comprises a sequence selected from the group consisting of:

```
FNHGAV (SEQ ID NO: 122)
and

FNNNVP (SEQ ID NO: 110).
```

In another preferred embodiment, the CDR3β comprises a sequence: AS[3βX1][3βX2]G[3βX3]NEQY (SEQ ID NO: 153), wherein [3βX1], [3βX2], [3βX3] are independently selected from any natural amino acid residue.

In another preferred embodiment, the [3βX1] is S, Q or M.
In another preferred embodiment, the [3βX2] is L, R, K, or M.
In another preferred embodiment, the [3βX3] is S, A, G or P.

In another preferred embodiment, the CDR3β comprises a sequence selected from the group consisting of:

```
ASQRGSNEQY (SEQ ID NO: 123),

ASQKGANEQY (SEQ ID NO: 124),

ASQLGSNEQY (SEQ ID NO: 125),

ASQLGANEQY (SEQ ID NO: 126),

ASQLGGNEQY (SEQ ID NO: 127),

ASQLGPNEQY (SEQ ID NO: 128),

ASQRGANEQY (SEQ ID NO: 129),

ASQMGSNEQY (SEQ ID NO: 130),

ASQMGANEQY (SEQ ID NO: 131)
and

ASMLGSNEQY (SEQ ID NO: 132).
```

In another preferred embodiment, the TCRα chain variable domain of the TCR does not simultaneously comprise following CDRs:

CDR1α: TSINN (SEQ ID NO: 106); CDR2α: IRSNERE (SEQ ID NO: 107); and CDR3α: ATDANGKII (SEQ ID NO: 108).

In another preferred embodiment, the TCRβ chain variable domain of the TCR does not simultaneously comprise following CDRs: CDR CDR1β: SGHDY (SEQ ID NO: 109); CDR2β: FNNNVP (SEQ ID NO: 110); and CDR3β: ASSLGSNEQY (SEQ ID NO: 111).

Natural Interchain Disulfide Bond and Artificial Interchain Disulfide Bond

A group of disulfide bonds is present between the Cα and Cβ chains in the membrane proximal region of a native TCR, which is named herein as "natural interchain disulfide bond". In the present invention, an interchain covalent disulfide bond which is artificially introduced and the position of which is different from the position of a natural interchain disulfide bond is named as "artificial interchain disulfide bond".

For convenience of description, in the present invention, the positions of the amino acid sequences of TRAC*01 and TRBC1*01 or TRBC2*01 are sequentially numbered in order from N-terminal to C-terminal. For example, the 60$^{th}$ amino acid in the order from N-terminal to C-terminal in TRBC1*01 or TRBC2*01 is P (valine), which can be described as Pro60 of TRBC1*01 or TRBC2*01 exon 1 in the present invention, and can also be expressed as the amino acid at position 60 of TRBC1*01 or TRBC2*01 exon 1. For another example, the 61$^{st}$ amino acid in the order from N-terminal to C-terminal in TRBC1*01 or TRBC2*01 is Q (glutamine), which can be described as Gln61 of TRBC1*01 or TRBC2*01 exon 1 in the invention, and can also be expressed as the amino acid at position 61 of TRBC1*01 or TRBC2*01 exon 1, and so on. In the present invention, the positions of the amino acid sequences of variable regions TRAV and TRBV are numbered according to the positions listed in IMGT. As for an amino acid in TRAV, the position is numbered as 46 in IMGT, which is described in the present invention as the amino acid at position 46 of TRAV, and so on. In the present invention, if the sequence positions of other amino acids are specifically described, the special description shall prevail.

Tumor

The term "tumor" refers to include all types of cancer cell growth or carcinogenic processes, metastatic tissues or malignant transformed cells, tissues or organs, regardless of pathological type or stage of infection. Examples of tumors include, without limitation, solid tumors, soft tissue tumors, and metastatic lesions. Examples of solid tumors include: malignant tumors of different organ systems, such as sarcoma, lung squamous cell carcinoma, and cancer. For example: infected prostate, lung, breast, lymph, gastrointestinal (e.g., colon) and genitourinary tract (e.g., kidney, epithelial cells), pharynx. Squamous cell carcinoma of lung includes malignant tumors, for example, most of colon cancer, rectal cancer, renal cell carcinoma, liver cancer, non-small cell cancer of lung, small intestine cancer and esophageal cancer. Metastatic lesions of the above cancers can likewise be treated and prevented using the methods and compositions of the invention.

DETAILED DESCRIPTION OF THE INVENTION

It is well known that the α chain variable domain and the β chain variable domain of a TCR contain three CDRs (similar to the complementarity determining regions of antibodies), respectively. CDR3 interacts with the antigen short peptide, and CDR1 and CDR2 interact with HLA. Therefore, the CDR of a TCR molecule determines its interaction with the antigen short peptide-HLA complex. The amino acid sequences of α chain variable domain and β chain variable domain of a wild type TCR capable of binding the complex of antigen short peptide SLLMWITQC (SEQ ID NO: 105) and HLA A2 (i.e., SLLMWITQC(SEQ ID NO: 105)-HLA A2 complex) are SEQ ID NO: 1 and SEQ ID NO: 2, respectively. This sequence was firstly discovered by the inventors. It has the following CDR regions:

α chain variable domain CDR CDR1: TSINN (SEQ ID NO: 106)
CDR2α: IRSNERE (SEQ ID NO: 107)
CDR3α: ATDANGKII (SEQ ID NO: 108)
and β chain variable domain CDR CDR1β: SGHDY (SEQ ID NO: 109)
CDR2β: FNNNVP (SEQ ID NO: 110)
CDR3β: ASSLGSNEQY (SEQ ID NO: 111)

In the present invention, a high affinity TCR is obtained by subjecting mutation and screen in the above CDR regions, which has an affinity for SLLMWITQC(SEQ ID NO: 105)-HLA A2 complex that is at least 2 times greater than that of a wild type TCR for SLLMWITQC(SEQ ID NO: 105)-HLA A2 complex.

In the present invention, a T cell receptor (TCR) is provided, which has an activity in binding to SLLMWITQC (SEQ ID NO: 105)-HLA A2 complex.

The T cell receptor comprises a TCR α chain variable domain and a TCR β chain variable domain, the TCR α chain variable domain comprises three CDR regions, and the reference sequences of the three CDR regions in the TCR α chain variable domain are listed follows, CDR1α: TSINN (SEQ ID NO: 106)
CDR2α: IRSNERE (SEQ ID NO: 107)
CDR3α: ATDANGKII (SEQ ID NO: 108) and contain at least one of the following mutations:

| Residue before mutation | Residue after mutation |
|---|---|
| T at position 1 of CDR1α | G |
| S at position 2 of CDR1α | W |
| I at position 3 of CDR1α | A or V |
| N at position 4 of CDR1α | Q |
| S at position 3 of CDR2α | T |
| N at position 4 of CDR2α | G |
| E at position 5 of CDR2α | Q |
| R at position 6 of CDR2α | A or Q |
| A at position 1 of CDR3α | M |
| T at position 2 of CDR3α | Y |
| A at position 4 of CDR3α | E or Q |
| N at position 5 of CDR3α | F or Y or W |
| G at position 6 of CDR3α | A or Q |
| K at position 7 of CDR3α | W or R or T or S or M or L |
| I at position 8 of CDR3α | W or V or Y or P, and |
| I at position 9 of CDR3α | N or E or D or Q or V or K or G or M or S |

And/or, the TCR β chain variable domain comprises three CDR regions, and the reference sequences of the three CDR regions of the TCR β chain variable domain are listed as follows, CDR1β: SGHDY (SEQ ID NO: 109)
CDR2β: FNNNVP (SEQ ID NO: 110)
CDR3β: ASSLGSNEQY (SEQ ID NO: 111) and contain at least one of the following mutations:

| Residue before mutation | Residue after mutation |
|---|---|
| N at position 3 of CDR2β | H |
| N at position 4 of CDR2β | G |
| V at position 5 of CDR2β | A |
| P at position 6 of CDR2β | V |
| S at position 3 of CDR3β | Q or M |
| L at position 4 of CDR3β | R or K or M, and |
| S at position 6 of CDR3β | A or G or P |

In more detail, the number of mutations in the CDR region of the TCR α chain is 3 or 4 or 6 or 8 or 9 or 11 or 12; and/or the number of mutations in the CDR region of the TCR β chain is 1 or 2 or 3 or 4 or 5 or 6 or 7.

Furthermore, the TCR of the present invention is an αβ heterodimeric TCR, and the α chain variable domain of the TCR comprises an amino acid sequence having at least 85%, preferably at least 90%; more preferably, at least 92%; most preferably at least 94% (e.g., may be at least 88%, 89%, 90%, 91%, 92%, 93%, 94%, 95%, 96%, 97%, 98%, 99% of sequence homology) of sequence homology with the amino acid sequence shown in SEQ ID NO: 1; and/or the β chain variable domain of the TCR comprises an amino acid sequence having at least 90%, preferably at least 92%; more preferably, at least 94%; most preferably at least 97% (e.g., may be at least 91%, 92%, 93%, 94%, 95%, 96%, 97%, 98%, 99% of sequence homology) of sequence homology with the amino acid sequence shown in SEQ ID NO: 2.

Furthermore, the TCR of the present invention is a single-chain TCR, and the α chain variable domain of the TCR comprises an amino acid sequence having at least 85%, preferably at least 90%; more preferably, at least 92%; most preferably at least 94% (e.g., may be at least 88%, 89%, 90%, 91%, 92%, 93%, 94%, 95%, 96%, 97%, 98%, 99% of sequence homology) of sequence homology with the amino acid sequence shown in SEQ ID NO: 3; and/or the β chain variable domain of the TCR comprises an amino acid sequence having at least 90%, preferably at least 92%; more preferably, at least 94%; most preferably at least 97% (e.g., may be at least 91%, 92%, 93%, 94%, 95%, 96%, 97%, 98%, 99% of sequence homology) of sequence homology with the amino acid sequence shown in SEQ ID NO: 4.

Preferably, the TCR comprises (i) all or part of a TCR α chain other than its transmembrane domain, and (ii) all or part of a TCR β chain other than its transmembrane domain, wherein both of (i) and (ii) comprise the variable domain and at least a portion of the constant domain of TCβ chain.

In the present invention, the three CDRs of α chain variable domain SEQ ID NO: 1 of the wild type TCR, i.e., CDR1, CDR2 and CDR3 are located at positions 27-31, 49-55 and 90-98 of SEQ ID NO: 1, respectively. Accordingly, the amino acid residue is numbered as shown in SEQ ID NO: 1, 27T is T at the first position of CDR1α, 28S is S at the second position of CDR1α, 29I is I at the third position of CDR1α, 30N is N at the $4^{th}$ position of CDR1α, 51S is S at the $3^{rd}$ position of CDR2α, 52N is N at $4^{th}$ position of CDR2α, 53E is E at the $5^{th}$ position of CDR2α, 54R is R at the $6^{th}$ position of CDR2α, 90A is A at the first position of CDR3α, 91T is T at the second position of CDR3α, 93A is A of the 4$^{th}$ position of CDR3α, 94N is N at the 5$^{th}$ position of CDR3α, 95G is G at the 6$^{th}$ position of CDR3α, 96K is K at the 7$^{th}$ position of CDR3α, 97I is I at the 8$^{th}$ position of CDR3α, and 98I is I at the 9$^{th}$ position of CDR3α.

Similarly, in the present invention, the three CDRs of β chain variable domain SEQ ID NO: 2 of the wild type TCR, i.e., CDR1, CDR2 and CDR3 are located at positions 27-31, 49-54 and 93-102 of SEQ ID NO: 2, respectively. Therefore, the amino acid residue number is numbered as shown in SEQ ID NO: 2, 51N is N at the 3$^{rd}$ position of CDR2β, 52N is N at the 4$^{th}$ position of CDR2β, 53V is V at the 5$^{th}$ position of CDR2β, 54P is P at the 6$^{th}$ position of CDR2β, 95S is S at the 3$^{rd}$ position of CDR3O, 96L is L at the 4$^{th}$ position of CDR3β, and 98S is S at the 6$^{th}$ position of CDR3O.

The present invention provides a TCR having the property of binding to SLLMWITQC(SEQ ID NO: 105)-HLA A2 complex, and comprises an α chain variable domain and a β chain variable domain, wherein the TCR has a mutation in the α chain variable domain shown in SEQ ID NO: 1, and the site of the mutated amino acid residue includes one or more of 27T, 28S, 29I, 30N, 51S, 52N, 53E, 54R, 90A, 91T, 93A, 94N, 95G, 96K, 97I, and 98I, wherein the amino acid residue is numbered as shown in SEQ ID NO: 1; and/or the TCR has a mutation in the β chain variable domain shown in SEQ ID NO: 2, and the site of the mutated amino acid residue includes one or more of 51N, 52N, 53V, 54P, 95S, 96L and 98S, wherein the amino acid residue is numbered as shown in SEQ ID NO: 2;

Preferably, the mutated TCR α chain variable domain comprises one or more amino acid residues selected from the group consisting of: 27G, 28W, 29A or 29V, 30Q, 51T, 52G, 53Q, 54Q or 54A, 90M, 91Y, 93E or 93Q, 94F or 94Y or 94W, 95A or 95Q, 96W or 96R or 96T or 96S or 96M or 96L, 97W or 97V or 97Y or 97P, and 98E or 98N or 98D or 98Q or 98K or 98V or 98G or 98M or 98S, wherein the amino acid residue is numbered as shown in SEQ ID NO: 1; and/or the mutated TCR β chain variable domain comprises one or more amino acid residues selected from the group consisting of: 51H, 52G, 53A, 54V, 95Q or 95M, 96R or 96K or 96M, and 98A or 98G or 98P, wherein the amino acid residue is numbered as shown in SEQ ID NO: 2.

More specifically, in the α chain variable domain, specific forms of the mutation include one or more groups of T27G, S28W, I29A/V, N30Q, S51T, N52G, E53Q, R54Q/A, A90M, T91Y, A93E/Q, N94F/Y/W, G95A/Q, K96W/R/T/S/M/L, I97W/V/Y/P and I98N/E/D/Q/K/V/G/M/S; and in the β chain variable domain, specific forms of the mutation include one or more groups of N51H, N52G, V53A, P54V, S95Q/M, L96R/K/M, and S98A/G/P.

Thr48 of the wild type TCR α chain constant region TRAC*01 exon 1 was mutated to cysteine according to the site-directed mutagenesis method well known to a skilled person in the art, and Ser57 of the β chain constant region TRBC1*01 or TRBC2*01 exon 1 was mutated to cysteine, so as to obtain a reference TCR, the amino acid sequences of which are shown in FIGS. 8a and 8b, respectively, and the mutated cysteine residues are indicated by bold letters. The above cysteine substitutions can form an artificial interchain disulfide bond between the constant regions of α and β chain of the reference TCR to form a more stable soluble TCR, so that it is easier to evaluate the binding affinity and/or binding half-life between TCR and SLLMWITQC(SEQ ID NO: 105)-HLA A2 complex. It will be appreciated that the CDR regions of the TCR variable region determine its affinity for pMHC complex, therefore, the above cysteine substitutions in the TCR constant region won't affect the binding affinity and/or binding half-life of TCR. Therefore, in the present invention, the measured binding affinity between the reference TCR and SLLMWITQC(SEQ ID NO: 105)-HLA A2 complex is considered to be the binding affinity between the wild-type TCR and SLLMWITQC(SEQ ID NO: 105)-HLA A2 complex. Similarly, if the binding affinity between the TCR of the invention and SLLMWITQC(SEQ ID NO: 105)-HLA A2 complex is determined to be at least 10 times the binding affinity between the reference TCR and SLLMWITQC(SEQ ID NO: 105)-HLA A2 complex, the binding affinity between the TCR of the present invention and SLLMWITQC(SEQ ID NO: 105)-HLA A2 complex is at least 10 times the binding affinity between the wild type TCR and SLLMWITQC(SEQ ID NO: 105)-HLA A2 complex.

The binding affinity (in inverse proportion to the dissociation equilibrium constant $K_D$) and the binding half-life (expressed as $T_{1/2}$) can be determined by any suitable method. It should be understood that doubling of the affinity of the TCR will halve $K_D$. $T_{1/2}$ is calculated as ln2 divided by dissociation rate ($K_{off}$). Therefore, doubling of $T_{1/2}$ will halve $K_{off}$. Preferably, the binding affinity or binding half-life of a given TCR is detected for several times by using the same test protocol, for example 3 or more times, and the average of the results is taken. In a preferred embodiment, these measurements are performed using the surface plasmon resonance (BIAcore) method in the Examples herein. The dissociation equilibrium constant $K_D$ of the reference TCR to SLLMWITQC(SEQ ID NO: 105)-HLA A2 complex is detected as 4.3E-05M, that is, 43 pM by the method, and in the present invention, the dissociation equilibrium constant $K_D$ of the wild type TCR to SLLMWITQC(SEQ ID NO: 105)-HLA A2 complex is also considered as 43 pM. Since doubling of the affinity of TCR will halve $K_D$, if the dissociation equilibrium constant $K_D$ of the high affinity TCR to SLLMWITQC(SEQ ID NO: 105)-HLA A2 complex is detected as 4.3E-06M, i.e., 4.3 pM, the affinity of the high affinity TCR for SLLMWITQC(SEQ ID NO: 105)-HLA A2 complex is 10 times that of the wild type TCR for SLLMWITQC(SEQ ID NO: 105)-HLA A2 complex. A skilled person is familiar with the conversion relationship between $K_D$ value units, i.e., 1 M=1000 μM, 1 μM=1000 nM, and 1 nM=1000 pM.

In a preferred embodiment of the invention, the affinity of the TCR for SLLMWITQC(SEQ ID NO: 105)-HLA A2 complex is at least 2 times that of the wild type TCR; preferably at least 5 times; more preferably at least 10 times.

In another preferred embodiment, the affinity of the TCR for SLLMWITQC(SEQ ID NO: 105)-HLA A2 complex is at least 50 times that of the wild type TCR; preferably, at least 100 times; more preferably, at least 500 times; most preferably, at least 1000 times.

In another preferred embodiment, the affinity of the TCR for SLLMWITQC(SEQ ID NO: 105)-HLA A2 complex is at least $10^4$ times that of the wild type TCR; preferably, at least 105 times; more preferably, at least $10^6$ times; most preferably, at least $10^7$ times.

Specifically, the dissociation equilibrium constant $K_D$ of the TCR for SLLMWITQC(SEQ ID NO: 105)-HLA A2 complex is ≤20 μM;

In another preferred embodiment, the dissociation equilibrium constant of the TCR for SLLMWITQC(SEQ ID NO: 105)-HLA A2 complex is 5 μM≤$K_D$≤10 μM; preferably, 0.1 μM≤$K_D$≤1 μM; more preferably, 1 nM≤$K_D$≤100 nM;

In another preferred embodiment, the dissociation equilibrium constant of the TCR for SLLMWITQC(SEQ ID NO:

105)-HLA A2 complex is 100 pM≤$K_D$≤1000 pM; preferably, 10 pM≤$K_D$≤100 pM; more preferably, 1 pM≤$K_D$≤10 pM.

Mutations can be carried out by any suitable method including, but not limited to, those based on polymerase chain reaction (PCR), restriction enzyme-based cloning or linkage-independent cloning (LIC) methods. Many standard molecular biology textbooks describe these methods in detail. More details about polymerase chain reaction (PCR) mutagenesis and cloning based on restriction enzymes can be found in Sambrook and Russell, (2001) Molecular Cloning-A Laboratory Manual (Third Edition) CSHL Publishing house. More information about LIC method can be found in Rashtchian, (1995) Curr Opin Biotechnol 6(1): 30-6.

The method for producing the TCR of the present invention may be, but not limited to, screening for a TCR having high affinity for SLLMWITQC(SEQ ID NO: 105)-HLA-A2 complex from a diverse library of phage particles displaying such TCRs, as described in a literature (Li, et al). (2005) Nature Biotech 23(3): 349-354).

It will be appreciated that genes expressing amino acid of α and β chain variable domain of a wild-type TCR or genes expressing amino acid of α and β chain variable domain of a slightly modified wild-type TCR can be used to prepare template TCRs. Changes necessary to produce the high affinity TCR of the invention are then introduced into the DNA encoding the variable domain of the template TCR.

The high affinity TCR of the present invention comprises one of α chain variable domain amino acid sequences of SEQ ID NO: 58, 59, 60, 61, 62, 63, 64, 65, 66, 67, 68, 69, 70, 71, 72, 73, 74, 75, 76, 77, 78, 79, 80, 81, 82, 83, 84, 85, 86 and/or one of β chain variable domain amino acid sequences of SEQ ID NO: 87, 88, 89, 90, 91, 92, 93, 94, 95, 96, 97, 98, 99, 100, 101, 102. Therefore, a TCR α chain comprising α chain variable domain amino acid sequence of the wild-type TCR (SEQ ID NO: 1) can bind to a TCR β chain comprising one of SEQ ID NO: 87, 88, 89, 90, 91, 92, 93, 94, 95, 96, 97, 98, 99, 100, 101, 102 to form a heterodimeric TCR or a single-chain TCR molecule. Alternatively, a TCR β chain comprising R variable domain amino acid sequence of the wild type TCR (SEQ ID NO: 2) can bind to a TCR α chain comprising one of SEQ ID NO: 58, 59, 60, 61, 62, 63, 64, 65, 66, 67, 68, 69, 70, 71, 72, 73, 74, 75, 76, 77, 78, 79, 80, 81, 82, 83, 84, 85, 86 to form a heterodimeric TCR or single-chain TCR molecule. Alternatively, a TCR α chain comprising one of TCR α chain variable domain amino acid sequences SEQ ID NO: 58, 59, 60, 61, 62, 63, 64, 65, 66, 67, 68, 69, 70, 71, 72, 73, 74, 75, 76, 77, 78, 79, 80, 81, 82, 83, 84, 85, 86 can bind to a TCR β chain comprising one of TCR β chain variable domain amino acid sequences SEQ ID NO: 87, 88, 89, 90, 91, 92, 93, 94, 95, 96, 97, 98, 99, 100, 101, 102 to form a heterodimeric TCR or a single-chain TCR molecule. In the present invention, the amino acid sequences of the α chain variable domain and β chain variable domain which form the heterodimeric TCR molecule are preferably selected from the following Table 1:

TABLE 1

| TCR Number | α chain variable domain sequence SEQ ID NO: | β chain variable domain sequence SEQ ID NO: |
|---|---|---|
| 1 | 58 | 2 |
| 2 | 59 | 87 |
| 3 | 60 | 87 |
| 4 | 60 | 88 |
| 5 | 60 | 89 |
| 6 | 61 | 90 |
| 7 | 62 | 90 |
| 8 | 63 | 87 |
| 9 | 64 | 91 |
| 10 | 65 | 90 |
| 11 | 66 | 89 |
| 12 | 1 | 92 |
| 13 | 1 | 93 |
| 14 | 1 | 94 |
| 15 | 1 | 95 |
| 16 | 1 | 96 |
| 17 | 1 | 97 |
| 18 | 1 | 98 |
| 19 | 67 | 2 |
| 20 | 68 | 2 |
| 21 | 69 | 2 |
| 22 | 70 | 2 |
| 23 | 71 | 2 |
| 24 | 72 | 2 |
| 25 | 73 | 2 |
| 26 | 74 | 2 |
| 27 | 75 | 2 |
| 28 | 76 | 2 |
| 29 | 77 | 2 |
| 30 | 78 | 2 |
| 31 | 79 | 2 |
| 32 | 80 | 2 |
| 33 | 81 | 2 |
| 34 | 82 | 2 |
| 35 | 83 | 2 |
| 36 | 59 | 2 |
| 37 | 63 | 2 |
| 38 | 84 | 2 |
| 39 | 85 | 2 |
| 40 | 86 | 2 |
| 41 | 1 | 99 |
| 42 | 1 | 100 |
| 43 | 1 | 101 |
| 44 | 1 | 102 |

For the purposes of the present invention, the TCR of the invention is a moiety having at least one TCR α and/or TCR β chain variable domain. They usually comprise both of TCR α chain variable domain and TCR β chain variable domain. They may be αβ heterodimers or single-chain forms or any other stable forms. In adoptive immunotherapy, the full length chain of the αβ heterodimeric TCR (including the cytoplasmic and transmembrane domains) can be transfected. The TCR of the present invention can be used as a targeting agent for delivering a therapeutic agent to an antigen presenting cell or in combination with other molecules to prepare a bifunctional polypeptide to direct effector cells, when the TCR is preferably in a soluble form.

For stability, it is disclosed in the prior art that a soluble and stable TCR molecule can be obtained by introducing an artificial interchain disulfide bond between the α and β chain constant domains of a TCR, as described in PCT/CN2015/093806. Therefore, the TCR of the invention may be a TCR that an artificial interchain disulfide bond is introduced between the residues of its α and β chain constant domains. Cysteine residues form an artificial interchain disulfide bond between the α and β chain constant domains of the TCR. A cysteine residue can replace other amino acid residue at a suitable position in a native TCR to form an artificial interchain disulfide bond. For example, Thr48 of TRAC*01 exon 1 and Ser57 of TRBC1*01 or TRBC2*01 exon 1 can be replaced to form a disulfide bond. Other sites for introducing a cysteine residue to form a disulfide bond may be: Thr45 of TRAC*01 exon 1 and Ser77 of TRBC1*01 or TRBC2*01 exon 1; Tyr10 of of TRAC*01 exon 1 and Ser17 of TRBC1*01 or TRBC2*01 exon 1; Thr45 of TRAC*01 exon 1 and Asp59 of TRBC1*01 or TRBC2*01 exon 1; Ser15 of TRAC*01 exon 1 and Glu15 of TRBC1*01 or TRBC2*01 exon 1; Arg53 of TRAC*01 exon 1 and Ser54 of TRBC1*01 or TRBC2*01 exon 1; Pro89 of TRAC*01 exon 1 and Ala19 of TRBC1*01 or TRBC2*01 exon 1; or Tyr10 of TRAC*01 exon 1 and Glu20 of TRBC1*01 or TRBC2*01 exon 1. That is, cysteine residues replace any group of the above-mentioned sites in α and β chain constant domains. A maximum of 15, or a maximum of 10, or a maximum of 8 or fewer amino acids may be truncated at one or more C-termini of the constant domain of the TCR of the invention such that it does not include cysteine residues to achieve the purpose of deleting native interchain disulfide bonds, or the cysteine residues forming a natural interchain disulfide bond can also be mutated to another amino acid for achieving the above purpose.

As described above, the TCR of the present invention may comprise an artificial interchain disulfide bond introduced between residues of its α and β chain constant domains. It should be noted that the introduced artificial disulfide bond as described above can be contained or not contained between the constant domains, and the TCR of the present invention may contain a TRAC constant domain sequence and a TRBC1 or TRBC2 constant domain sequence. The TRAC constant domain sequence and the TRBC1 or TRBC2 constant domain sequence of the TCR can be joined by a natural interchain disulfide bond present in the TCR.

Additionally, as for stability, it was also disclosed in a patent literature PCT/CN2016/077680 that the introduction of an artificial interchain disulfide bond between α chain variable region and β chain constant region of a TCR can significantly improve the stability of the TCR. Therefore, an artificial interchain disulfide bond may be contained between α chain variable region and β chain constant region of a high affinity TCR of the present invention. Specifically, cysteine residues forming an artificial interchain disulfide bond between α chain variable region and β chain constant region of the TCR is substituted for: an amino acid at position 46 of TRAV and amino acid at position 60 of TRBC1*01 or TRBC2*01 exon 1; an amino acid at position 47 of TRAV and amino acid at position 61 of TRBC1*01 or TRBC2*01 exon 1; amino acid at position 46 of TRAV and amino acid at position 61 of TRBC1*01 or TRBC2*01 exon 1; or an amino acid at position 47 of TRAV and amino acid at position 60 of TRBC1*01 or TRBC2*01 exon 1. Preferably, such a TCR may comprises (i) all or part of TCR α chain other than its transmembrane domain, and (ii) all or part of TCR β chain other than its transmembrane domain, wherein both of (i) and (ii) comprise the variable domain and at least a portion of constant domains of the TCR chain, and the α chain and β chain form a heterodimer. More preferably, such TCR may comprise α chain variable domain and β chain variable domain and all or part of β chain constant domain other than the transmembrane domain, which, however, does not comprise α chain constant domain, and the α chain variable domain of the TCR and the β chain form a heterodimer.

For stability, in another aspect, the TCR of the present invention also includes a TCR having a mutation in its hydrophobic core region, and these mutations in hydrophobic core region are preferably mutations capable of increasing the stability of the TCR of the present invention, as described in WO 2014/206304. Such a TCR can have mutations at following positions in the variable domain hydrophobic core: (α and/or β chain) variable region amino acids at position 11, 13, 19, 21, 53, 76, 89, 91, 94, and/or α chain J gene (TRAJ) short peptide amino acid at reciprocal positions 3, 5, 7 and/or β chain J gene (TRBJ) short peptide amino acid at reciprocal positions 2, 4, 6, wherein the positions in amino acid sequence are numbered according to the position numbers listed in the International Immunogenetics Information System (IMGT). A skilled person in the art will know the above-described international immunogenetic information system and can obtain the position numbers of the amino acid residues of different TCRs in the IMGT based on the database.

More specifically, in the present invention, a TCR in which there is a mutation in the hydrophobic core region may be a high-stability single-chain TCR consisting of TCR α and β chain variable domains that linked by a flexible peptide chain. The CDR regions of TCR variable region determine its affinity for the short peptide-HLA complex, and mutations in hydrophobic core can increase the stability of the TCR, but won't affect its affinity for the short peptide-HLA complex. It should be noted that the flexible peptide chain in the present invention may be any peptide chain suitable for linking TCR α and β chain variable domains. The template chain constructed in Example 1 of the present invention for screening high-affinity TCRs is a high-stability single-chain TCR containing mutations in hydrophobic core as described above. The affinity between a TCR and SLLMWITQC(SEQ ID NO: 105)-HLA-A2 complex can be easily evaluated by using a TCR with higher stability.

The CDR regions of α chain variable domain and β chain variable domain of the single chain template TCR are identical to the CDR regions of the wild type TCR. That is, the three CDRs of α chain variable domain are CDR1α: TSINN (SEQ ID NO: 106), CDR2α: IRSNERE (SEQ ID NO: 107), and CDR3α: ATDANGKII (SEQ ID NO: 108) and the three CDRs of β chain variable domains are CDR1α: SGHDY (SEQ ID NO: 109), CDR2β: FNNNVP (SEQ ID NO: 110), and CDR3β: ASSLGSNEQY (SEQ ID NO: 111), respectively. The amino acid sequence (SEQ ID NO: 54) and nucleotide sequence (SEQ ID NO: 55) of the single-chain template TCR are shown in FIGS. 7a and 7b, respectively, thereby screening a single-chain TCR consisting of α-chain variable domain and β-chain variable domain and having high affinity for SLLMWITQC(SEQ ID NO: 105)-HLA A2 complex.

In the present invention, the three CDRs of α chain variable domain of the single-chain template TCR (SEQ ID NO: 3), i.e., CDR1, CDR2 and CDR3 are located at positions 27-31, 49-55 and 90-98 of SEQ ID NO: 3, respectively. Accordingly, the amino acid residues are numbered according to the number as shown in SEQ ID NO: 3. 27T is T at the first position of CDR1α, 28S is S at the second position of CDR1α, 29I is I at the third position of CDR1α, 30N is N at the $4^{th}$ position of CDR1α, 51S is S at the $3^{rd}$ position of CDR2α, 52N is N at the $4^{th}$ position of CDR2α, 53E is E at the $5^{th}$ position of CDR2α, 54R is R at the $6^{th}$ position of CDR2α, 90A is A at the first position of CDR3α, 91T is T at the second position of CDR3α, 93A is A at the $4^{th}$ position of CDR3α, 94N is N at the $5^{th}$ position of CDR3α, 95G is G at the $6^{th}$ position of CDR3α, 96K is K at the $7^{th}$ position of CDR3α, 97I is I at the $8^{th}$ position of CDR3α, and 98I is I at the $9^{th}$ position of CDR3α.

Similarly, in the present invention, the three CDRs of β chain variable domain of the single-chain template TCR (SEQ ID NO: 4), i.e., CDR1, CDR2 and CDR3 are located at positions 27-31, 49-54 and 93-102 of SEQ ID NO: 2, respectively. Therefore, the amino acid residues are numbered according to the number as shown in SEQ ID NO: 2. 51N is N at the $3^{rd}$ position of CDR2β, 52N is N at the $4^{th}$ position of CDR2β, 53V is V at the $5^{th}$ position of CDR2β, 54P is P at the $6^{th}$ position of CDR2β, 95S is A at the $3^{rd}$ position of CDR3β, 96L is L at the $4^{th}$ position of CDR3β, and 98S is S at the $6^{th}$ position of CDR3β.

The αβ heterodimer of the present invention having high affinity for SLLMWITQC(SEQ ID NO: 105)-HLA-A2 complex is obtained by transferring the CDR regions of α and β chain variable domains of the selected high affinity single-chain TCR to the corresponding positions of α chain variable domain (SEQ ID NO: 1) and β chain variable domain (SEQ ID NO: 2) of a wild type TCR.

In some embodiments of the invention, when using the numbering set forth in SEQ ID NO: 1, one or more of amino acid residue 19A (i.e., the $19^{th}$ position of α chain variable region listed in IMGT), 21M (i.e., the $21^{st}$ position of α chain variable region listed in IMGT) and 79S (i.e., the $94^{th}$ position of α chain variable region listed in IMGT) in the hydrophobic core of α chain variable domain of the TCR of the invention mutates and/or when using the numbering set forth in SEQ ID NO: 2, one or more of amino acid residue 13T (i.e., the $13^{th}$ position of β chain variable region listed in IMGT) and 82S (i.e., the $94^{th}$ position of β chain variable region listed in IMGT) in the hydrophobic core of β chain variable domain of the TCR mutates.

More specifically, in some preferred embodiments of the invention, when using the numbering set forth in SEQ ID NO: 1, one or more of amino acid residues 19V, 21I and 79V are contained in the hydrophobic core of α chain variable domain of the invention and/or when using the numbering set forth in SEQ ID NO: 2, one or more of amino acid residues 13V and 82V are contained in the hydrophobic core of TCRβ chain variable domain. More specifically, the mutated form of TCRα variable domain hydrophobic core comprises one or more of A19V, M21I and S79V; and the mutated form of TCRβ variable domain hydrophobic core comprises one or more of T13V and S82V.

The high affinity TCR of the invention further comprises one of α chain variable domain amino acid sequences of SEQ ID NO: 9, 10, 11, 12, 13, 14, 15, 16, 17, 18, 19, 20, 21, 22, 23, 24, 25, 26, 27, 28, 29, 30, 31, 32, 33, 34, 35, 36 and 37 and/or one of β chain variable domain amino acid sequences of SEQ ID NO: 38, 39, 40, 41, 42, 43, 44, 45, 46, 47, 48, 49, 50, 51, 52 and 53. Therefore, the α chain variable domain (SEQ ID NO: 3) of the above described high-stability single-chain TCR as a template chain can be combined with TCR β chain variable domain, the amino acid sequence of which is SEQ ID NO: 38, 39, 40, 41, 42, 43, 44, 45, 46, 47, 48, 49, 50, 51, 52 or 53, to form the single-chain TCR molecule. Alternatively, the β chain variable domain (SEQ ID NO: 4) of the above described high-stability single-chain TCR as a template chain can be combined with TCR α chain variable domain, the amino acid sequence of which is SEQ ID NO: 9, 10, 11, 12, 13, 14, 15, 16, 17, 18, 19, 20, 21, 22, 23, 24, 25, 26, 27, 28, 29, 30, 31, 32, 33, 34, 35, 36 or 37, to form the single-chain TCR molecule. Alternatively, one of the TCR α chain variable domains SEQ ID NO: 9, 10, 11, 12, 13, 14, 15, 16, 17, 18, 19, 20, 21, 22, 23, 24, 25, 26, 27, 28, 29, 30, 31, 32, 33, 34, 35, 36 and 37 can be combined with one of the TCR β chain variable domains SEQ ID NO: 38, 39, 40, 41, 42, 43, 44, 45, 46, 47, 48, 49, 50, 51, 52 and 53 to form the single-chain TCR molecule. In the present invention, the amino acid sequences of α chain variable domain and β chain variable domain of the high-affinity single-chain TCR molecule are preferably selected from the following Table 2:

TABLE 2

| TCR numbering | α chain variable domain sequence SEQ ID NO: | β chain variable domain sequence SEQ ID NO: |
| --- | --- | --- |
| s-1 | 9 | 4 |
| s-2 | 10 | 38 |
| s-3 | 11 | 38 |
| s-4 | 11 | 39 |
| s-5 | 11 | 40 |
| s-6 | 12 | 41 |
| s-7 | 13 | 41 |
| s-8 | 14 | 38 |
| s-9 | 15 | 42 |
| s-10 | 16 | 41 |
| s-11 | 17 | 40 |
| s-12 | 3 | 43 |
| s-13 | 3 | 44 |
| s-14 | 3 | 45 |
| s-15 | 3 | 46 |
| s-16 | 3 | 47 |
| s-17 | 3 | 48 |
| s-18 | 3 | 49 |
| s-19 | 18 | 4 |
| s-20 | 19 | 4 |
| s-21 | 20 | 4 |
| s-22 | 21 | 4 |
| s-23 | 22 | 4 |
| s-24 | 23 | 4 |
| s-25 | 24 | 4 |
| s-26 | 25 | 4 |
| s-27 | 26 | 4 |
| s-28 | 27 | 4 |
| s-29 | 28 | 4 |
| s-30 | 29 | 4 |
| s-31 | 30 | 4 |
| s-32 | 31 | 4 |
| s-33 | 32 | 4 |
| s-34 | 33 | 4 |
| s-35 | 34 | 4 |
| s-36 | 10 | 4 |
| s-37 | 14 | 4 |
| s-38 | 35 | 4 |
| s-39 | 36 | 4 |
| s-40 | 37 | 4 |
| s-41 | 3 | 50 |
| s-42 | 3 | 51 |
| s-43 | 3 | 52 |
| s-44 | 3 | 53 |

The TCR of the present invention can be provided in a form of multivalent complex. The multivalent TCR complex of the present invention comprises a polymer formed by combining two, three, four or more TCRs of the present invention, for example, a tetrameric domain of p53 can be used to produce a tetramer. Alternatively, more TCRs of the invention can be combined with another molecule to form a complex. The TCR complexes of the invention can be used to track or target cells that present a particular antigen in vitro or in vivo, or produce intermediates of other multivalent TCR complexes with such uses.

The TCR of the present invention may be used alone or combined with a conjugate in a covalent manner or other manner, preferably in a covalent manner. The conjugate includes a detectable label (for diagnostic purposes, wherein the TCR is used to detect the presence of a cell presenting SLLMWITQC(SEQ ID NO: 105)-HLA-A2 complex), a therapeutic agent, a PK (protein kinase) modifying moiety, or combination of any of the above described substances.

Detectable labels for diagnostic purposes include, but are not limited to, fluorescent or luminescent labels, radioactive labels, MRI (magnetic resonance imaging) or CT (electron computed tomography) contrast agents, or enzymes capable of producing detectable products.

Therapeutic agents that can be combined with or coupled to the TCRs of the invention include, but are not limited to: 1. Radionuclides (Koppe et al., 2005, Cancer metastasis reviews 24, 539); 2. Biotoxin (Chaudhary et al., 1989, Nature 339, 394; Epel et al., 2002, Cancer Immunology and Immunotherapy 51, 565); 3. Cytokines, such as IL-2, etc. (Gillies et al., 1992, National Academy of Sciences (PNAS) 89, 1428; Card et al., 2004, Cancer Immunology and Immunotherapy 53, 345; Halin et al., 2003, Cancer Research 63, 3202); 4. Antibody Fc fragment (Mosquera et al., 2005, The Journal Of Immunology 174, 4381); 5. Antibody scFv fragments (Zhu et al., 1995, International Journal of Cancer 62, 319); 6. Gold nanoparticles/Nanorods (Lapotko et al., 2005, Cancer letters 239, 36; Huang et al., 2006, Journal of the American Chemical Society 128, 2115); 7. Viral particles (Peng et al., 2004, Gene therapy 11, 1234); 8. Liposomes (Mamot et al., 2005, Cancer research 65, 11631); 9. Nanomagnetic particles; 10. Prodrug activating enzymes (e.g., DT-diaphorase (DTD) or biphenyl hydrolase-like protein (BPHL); 11. chemotherapeutic agent (e.g., cisplatin) or any form of nanoparticles, and the like.

An antibody to which the TCR of the present invention binds or a fragment thereof includes an anti-T cell or an NK-cell determining antibody, such as an anti-CD3 or anti-CD28 or anti-CD16 antibody, and the above antibody or a fragment thereof binds to a TCR, thereby better directing effector cells to target cells. In a preferred embodiment, the TCR of the invention binds to an anti-CD3 antibody or a functional fragment or variant thereof. Specifically, a fusion molecule of the TCR of the present invention and an anti-CD3 single-chain antibody comprises a TCR α chain variable domain, the amino acid sequence of which is selected from the group consisting of SEQ ID NO: 9, 10, 11, 12, 13, 14, 15, 16, 17, 18, 19, 20, 21, 22, 23, 24, 25, 26, 27, 28, 29, 30, 31, 32, 33, 34, 35, 36, 37, 58, 59, 60, 61, 62, 63, 64, 65, 66, 67, 68, 69, 70, 71, 72, 73, 74, 75, 76, 77, 78, 79, 80, 81, 82, 83, 84, 85, 86 and a TCR β chain variable domain, the amino acid sequence of which is selected from the group consisting of SEQ ID NO: 38, 39, 40, 41, 42, 43, 44, 45, 46, 47, 48, 49, 50, 51, 52, 53, 87, 88 89, 90, 91, 92, 93, 94, 95, 96, 97, 98, 99, 100, 101, 102.

The invention also relates to a nucleic acid molecule encoding the TCR of the invention. The nucleic acid molecule of the invention may be in a form of DNA or RNA. DNA can be a coding strand or a non-coding strand. For example, a nucleic acid sequence encoding the TCR of the invention may be the same as the nucleic acid sequence set forth in the Figures of the invention or a degenerate variant thereof. By way of example, "degenerate variant", as used herein, refers to a nucleic acid sequence which encodes a protein with a sequence of SEQ ID NO: 54, but is differences from the sequence of SEQ ID NO: 55.

The full length sequence of the nucleic acid molecule of the present invention or a fragment thereof can generally be obtained by, but not limited to, PCR amplification, recombinant methods or synthetic methods. At present, it has been possible to obtain a DNA sequence encoding the TCR (or a fragment thereof, or a derivative thereof) of the present invention completely by chemical synthesis. And then the DNA sequence can be introduced into various existing DNA molecules (or vectors) and cells known in the art.

The invention also relates to vectors comprising the nucleic acid molecules of the invention, as well as host cells genetically engineered using the vectors or coding sequences of the invention.

The invention also encompasses isolated cells, particularly T cells, which express the TCR of the invention. There are a number of methods suitable for T cell transfection with DNA or RNA encoding the high affinity TCR of the invention (e.g., Robbins et al., (2008) J. Immunol. 180: 6116-6131). T cells expressing the high affinity TCR of the invention can be used in adoptive immunotherapy. A skilled person in the art can know many suitable methods for performing adoptive therapy (e.g., Rosenberg et al., (2008) Nat Rev Cancer 8(4): 299-308).

The invention also provides a pharmaceutical composition, comprising a pharmaceutically acceptable carrier and a TCR of the invention, or a TCR complex of the invention, or cells presenting the TCR of the invention.

The invention also provides a method for treating a disease, comprising administering to a subject in need thereof an appropriate amount of a TCR of the invention, or a TCR complex of the invention, or cells presenting a TCR of the invention, or a pharmaceutical composition of the invention.

It should be understood that the amino acid names herein are identified by internationally accepted single English letters, and the corresponding three-letter abbreviated names of an amino acid are: Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y), Val (V);

In the present invention, both of Pro60 or 60P represent proline at position 60. Further, regarding the expression of the specific form of mutation in the present invention, such as "T27G" represents that T at the $27^{th}$ position is substituted by G. Similarly, "I29A/V" means that I at the $29^{th}$ position is substituted by A or substituted by V, and so on.

In the art, when an amino acid with similar properties is used for substitution, the function of the protein is usually not altered. The addition of one or several amino acids at C-terminus and/or N-terminus generally does not alter the structure and function of the protein. Therefore, the TCR of the invention further includes a TCR, wherein up to 5, preferably up to 3, more preferably up to 2, the most preferably 1 amino acid (especially an amino acid located outside CDR regions) of the TCR of the invention is replaced by an amino acid with similar properties and still be able to maintain its function.

The present invention also includes a TCR obtained from the TCR of the present invention by slight modification. Form of modification (usually without altering the primary structure) includes: chemically derived forms of the TCR of the invention, such as acetylation or carboxylation. Modifications also include glycosylation, such as those TCRs produced by glycosylation modifications in the synthesis and processing or in further processing steps of the TCR of the invention. Such modification can be accomplished by exposing the TCR to an enzyme performing glycosylation (such as a mammalian glycosylation enzyme or a deglycosylation enzyme). Modification forms also include sequences having phosphorylated amino acid residues (such as phosphotyrosine, phosphoserine, phosphothreonine). Also included are TCRs that have been modified to enhance their antiproteolytic properties or optimize solubility properties.

The TCR, TCR complexes of the invention or T cells transfected by the TCRs of the invention can be provided in a pharmaceutical composition together with a pharmaceutically acceptable carrier. The TCR, multivalent TCR complex or cell of the invention is typically provided as part of a sterile pharmaceutical composition, which typically comprises a pharmaceutically acceptable carrier. The pharmaceutical composition can be of any suitable form (depending on the desired method for administration to a patient). It can be provided in a unit dosage form, usually in a sealed container, and can be provided as part of a kit. Such kit (but not required) includes instructions. It can include a plurality of said unit dosage form.

Furthermore, the TCR of the invention may be used alone or in combination with other therapeutic agents (e.g., formulated in the same pharmaceutical composition).

The pharmaceutical composition may also contain a pharmaceutically acceptable carrier. The term "pharmaceutically acceptable carrier" refers to a carrier for the administration of a therapeutic agent. The term refers to such pharmaceutical carriers which themselves do not induce the production of antibodies harmful to the individual receiving the composition and which are not excessively toxic after administration. These carriers are well known to a skilled person in the art. A full discussion of pharmaceutically acceptable excipients can be found in Remington's Pharmaceutical Sciences (Mack Pub. Co., N. J. 1991). Such carriers include, but are not limited to, saline, buffer, dextrose, water, glycerol, ethanol, adjuvants, and combinations thereof.

The pharmaceutically acceptable carrier in the therapeutic composition may contain a liquid such as water, saline, glycerol and ethanol. In addition, auxiliary substances such as wetting or emulsifying agents, pH buffering substances and the like may also be present in these carriers.

In general, the therapeutic compositions can be formulated as injectables, such as liquid solutions or suspensions; and solid forms such as liquid carriers, which may be suitable for being formulated in solution or suspension prior to injection.

Once a composition of the invention is formulated, it can be administered by conventional routes including, but not limited to, intraocular, intramuscular, intravenous, subcutaneous, intradermal, or topical administration, preferably parenteral, including subcutaneous, intramuscular or intravenous administration. A subject to be prevented or treated may be an animal; especially a human.

When the pharmaceutical composition of the present invention is used for actual treatment, pharmaceutical compositions of various dosage forms may be employed depending on the uses, preferably, an injection, an oral preparation, or the like.

These pharmaceutical compositions can be formulated by mixing, diluting or dissolving according to conventional methods, occasionally, suitable pharmaceutical additives can be added such as excipients, disintegrating agents, binders, lubricants, diluents, buffers, isotonicity Isotonicities, preservatives, wetting agents, emulsifiers, dispersing agents, stabilizers and co-solvents, and the formulation process can be carried out in a customary manner depending on the dosage form.

The pharmaceutical composition of the present invention can also be administered in the form of a sustained release preparation. For example, the TCR of the present invention can be incorporated into a pill or microcapsule in which the sustained release polymer is used as a carrier, and then the pill or microcapsule is surgically implanted into the tissue to be treated. Examples of the sustained-release polymer include ethylene-vinyl acetate copolymer, polyhydrometaacrylate, polyacrylamide, polyvinylpyrrolidone, methylcellulose, lactic acid polymer, lactic acid-glycolic acid copolymer or the like, preferably biodegradable polymer, such as lactic acid polymer and lactic acid-glycolic acid copolymer.

When the pharmaceutical composition of the present invention is used for actual treatment, the amount of the TCR or TCR complex of the present invention or the cell presenting the TCR of the present invention as an active ingredient may be reasonably determined based on the body weight, age, sex, and degree of symptoms of each patient to be treated, and ultimately by a doctor.

Main Advantages of the Invention:

(1) The affinity and/or binding half-life of the TCR of the present invention for SLLMWITQC(SEQ ID NO: 105)-HLA-A2 complex is at least 2 times, preferably at least 10 times that of a wild type TCR.

(2) The affinity and/or binding half-life of the TCR of the present invention for SLLMWITQC(SEQ ID NO: 105)-HLA-A2 complex is at least 100 times, preferably at least 1000 times, and more preferably up to $10^4$-$10^7$ times that of a wild type TCR.

(3) Effector cells transduced with the high-affinity TCR of the present invention exhibit a strong killing effect on target cells.

The invention is further illustrated by the following specific examples. It is to be understood that these examples are for illustrative purposes only and are not intended to limit the scope of the invention. The experimental methods in the following examples which do not specify the specific conditions are usually performed under conventional conditions, for example, conditions described in Sambrook and Russell et al., Molecular Cloning-A Laboratory Manual (Third Edition) (2001) CSHL Publishing company, or in accordance with the conditions recommended by the manufacturer. Percentages and parts are by weight unless otherwise stated.

Materials and Method

The experimental materials used in the examples of the present invention can commercially available, unless otherwise specified, among which E. coli DH5u was purchased from Tiangen, E. coli BL21 (DE3) was purchased from Tiangen, E. coli Tuner (DE3) was purchased from Novagen, and plasmid pET28a was purchased from Novagen.

Example 1. Generation of Stable Single-Chaind TCR Template Chains with Mutations in Hydrophobic Core In the present invention, a method of site-directed mutagenesis was used according to a patent literture WO2014/206304 to construct a stable single-chain TCR molecule consisting of TCR α and β-chain variable domain connected by a flexible short peptide, and the amino acid and DNA sequences of which are SEQ ID NO: 54 and SEQ ID NO: 55, respectively, as shown in FIGS. 7a and 7b. The single-chain TCR molecule was used as a template for screening high-affinity TCR molecules. The amino acid sequences of a variable domain (SEQ ID NO: 3) and β variable domain (SEQ ID NO: 4) of the template chain are shown in FIGS. 2a and 2b; the corresponding DNA sequences are SEQ ID NO: 5 and 6, respectively, as shown in FIGS. 3a and 3b; and the amino acid sequence and DNA sequence of the flexible short linker are SEQ ID NOS: 7 and 8, respectively, as shown in FIGS. 4a and 4b.

The target gene carrying the template chain was digested with NcoI and NotI, and ligated with pET28a vector digested with NcoI and NotI. The ligation product was transformed into E. coli DH5u, plated on a kanamycin-containing LB plate, inverted and cultured at 37° C. overnight, and the positive clones were picked for PCR screening. Positive recombinants were sequenced to determine the correct sequence and the recombinant plasmid was extracted and transferred into *E. coli* BL21 (DE3) for expression.

Example 2. Expression, Renaturation and Purification of the Stable Single-Chain TCR Constructed in Example 1

All of BL21(DE 3) colonies containing the recombinant plasmid pET28a-template chain prepared in Example 1 were inoculated into LB medium containing kanamycin, and cultured at 37° C. until $OD_{600}$ was 0.6-0.8. IPTG was added to a final concentration of 0.5 mM, and cultured at 37° C. for another 4 hrs. The cell pellets were harvested by centrifugation at 5000 rpm for 15 mins, and the cell pellets were lysed with Bugbuster Master Mix (Merck). The inclusion bodies were recovered by centrifugation at 6000 rpm for 15 min, followed by washing with Bugbuster (Merck) to remove cell debris and membrane fraction. The inclusion bodies were collected by centrifugation at 6000 rpm for 15 min, and dissolved in a buffer (20 mM Tris-HCl pH 8.0, 8 M urea), and the insoluble matters were removed by high-speed centrifugation. The supernatant was quantitativly determined by BCA method, and then dispensed and stored at −80° C. until use.

To 5 mg of dissolved single-chain TCR inclusion body protein, 2.5 mL of buffer (6 M Gua-HCl, 50 mM Tris-HCl pH 8.1, 100 mM NaCl, 10 mM EDTA) was added, then DTT was added to a final concentration of 10 mM, and incubated at 37° C. for 30 min. The single-chain TCRs as treated above was added dropwise to a 125 mL of refolding buffer (100 mM Tris-HCl pH 8.1, 0.4 M L-arginine, 5 M urea, 2 mM EDTA, 6.5 mM β-mercapthoethylamine, 1.87 mM Cystamine) with a syringe, and stirred at 4° C. for 10 min. Then the refolded solution was loaded into a cellulose membrane dialysis bag with a cut-off of 4 kDa, and the dialysis bag was placed in 1 L of pre-cooled water, and stirred slowly at 4° C. overnight. After 17 hours, the dialysis liquid was changed to 1 L of pre-chilled buffer (20 mM Tris-HCl pH 8.0) and dialysis was continued for 8 h at 4° C. The dialysis liquid was then replaced with the same fresh buffer and dialysis was continued overnight. After 17 hours, the sample was filtered through a 0.45 μm filter, vacuum degassed and purified through an anion exchange column (HiTrap Q HP, GE Healthcare) with a linear gradient elution of 0-1 M NaCl prepared with 20 mM Tris-HCl pH 8.0. The collected fractions were subjected to SDS-PAGE analysis, and the fractions containing single-chain TCRs were concentrated and further purified by a gel filtration column (Superdex 75 10/300, GE Healthcare), and the target components were also subjected to SDS-PAGE analysis.

The eluted fractions for BIAcore analysis was further tested for purity using gel filtration. The conditions were as follows: chromatographic column Agilent Bio SEC-3 (300 A, φ7.8×300 mm), mobile phase 150 mM phosphate buffer, flow rate 0.5 mL/min, column temperature 25° C., and UV detection wavelength 214 nm.

Example 3. Binding Characterization

BIAcore Analysis

The binding activity of the TCR molecule to SLLMWITQC(SEQ ID NO: 105)-HLA-A2 complex was detected using BIAcore T200 real-time analysis system. The anti-streptavidin antibody (GenScript) was added to a coupling buffer (10 mM sodium acetate buffer, pH 4.77), and then the antibody was passed through a CM5 chip pre-activated with EDC and NHS to immobilize the antibody on the surface of the chip. The unreacted activated surface was finally blocked with a solution of ethanolamine in hydrochloric acid to complete the coupling process at a coupling level of about 15,000 RU.

A low concentration of streptavidin flowed over the surface of the antibody-coated chip, then SLLMWITQC (SEQ ID NO: 105)-HLA-A2 complex flowed through the detection channel with another channel being used as a reference channel. 0.05 mM biotin flowed over the chip for 2 min at a flow rate of 10 μL/min, thereby blocking the remaining binding sites for streptavidin. The affinity was determined by single-cycle kinetic analysis. TCR was diluted to several different concentrations with HEPES-EP buffer (10 mM HEPES, 150 mM NaCl, 3 mM EDTA, 0.005% P20, pH 7.4), and flowed over the surface of the chip in turn at a flow rate of 30 μL/min, with a binding time of 120 s per injection. After the last injection, the chip was placed for dissociation for 600 s. At the end of each round of assay, the chip was regenerated with 10 mM Gly-HCl, pH 1.75. Kinetic parameters were calculated using BIAcore Evaluation software.

The preparation process for the above SLLMWITQC (SEQ ID NO: 105)-HLA-A2 complex is described as follows:

a. Purification 100 ml of *E. coli* liquid induced to express heavy or light chain was collected, and centrifuged at 8000 g for 10 min at 4° C., and the cells were washed once with 10 ml of PBS, and then vigorously shaken in 5 ml of BugBuster Master Mix Extraction Reagents (Merck) for resuspending the cells. The suspension was incubated for 20 min at room temperature, and then centrifuged at 6000 g for 15 min at 4° C. The supernatant was discarded to collect inclusion bodies.

The above inclusion bodies was resuspended in 5 ml BugBuster Master Mix and incubated vortically at room temperature for 5 min. 30 ml of 10 time-diluted BugBuster was added, mixed, and centrifuged at 6000 g for 15 min at 4° C. The supernatant was discarded, 30 ml of 10 time-diluted BugBuster was added to resuspend the inclusion body, mixed, and centrifuged twice at 6000 g at 4° C. for 15 min. 30 ml of 20 mM Tris-HCl pH 8.0 was added to resuspend the inclusion bodies, mixed, and centrifuged at 6000 g at 4° C. for 15 min. Finally, inclusion bodies were dissolved in 20 mM Tris-HCl 8M urea, and the purity of inclusion bodies was determined by SDS-PAGE and the concentration was measured by BCA kit.

b. Refolding

Synthesized short peptide SLLMWITQC(SEQ ID NO: 105) (Beijing Saibaisheng Gene Technology Co., Ltd.) were dissolved in DMSO to a concentration of 20 mg/ml. Inclusion bodies of light and heavy chains were solubilized in 8 M urea, 20 mM Tris pH 8.0, 10 mM DTT, and further denatured by adding 3 M guanidine hydrochloride, 10 mM sodium acetate, 10 mM EDTA before refolding. SLLMWITQC(SEQ ID NO: 105) peptide was added to a refolding buffer (0.4 M L-arginine, 100 mM Tris pH 8.3, 2 mM EDTA, 0.5 mM oxidized glutathione, 5 mM reduced glutathione, 0.2 mM PMSF, cooled to 4° C.) at 25 mg/L (final concentration). Then 20 mg/L of light chain and 90 mg/L of heavy chain (final concentration, heavy chain was added in three portions, 8 h/portion) were successively added, and refolded at 4° C. for at least 3 days to completion of refolding, and SDS-PAGE was used to confirm refolding.

c. Purification Upon Refolding

The refolding buffer was replaced with 10 volumes of 20 mM Tris pH 8.0 for dialysis, and the buffer was exchanged for at least two times to substantially reduce the ionic strength of the solution. After dialysis, the protein solution was filtered through a 0.45 μm cellulose acetate filter and loaded onto a HiTrap Q HP (GE, General Electric Company) anion exchange column (5 ml bed volume). The protein was eluted with a linear gradient of 0-400 mM NaCl prepared in 20 mM Tris pH 8.0 using Akta Purifier (GE), and the pMHC was eluted at approximately 250 mM NaCl. Peak fractions were collected and the purity thereof was detected by SDS-PAGE.

d. Biotinylation

Purified pMHC molecules were concentrated in a Millipore ultrafiltration tube, while the buffer was replaced with 20 mM Tris pH 8.0, and then biotinylation reagent 0.05 M Bicine pH 8.3, 10 mM ATP, 10 mM MgOAc, 50 μM D-Biotin, 100 μg/ml BirA enzyme (GST-BirA) was added. The resulting mixture was incubated at room temperature overnight, and SDS-PAGE was used to detect the completion of biotinylation.

e. Purification of Biotinylated Complex

The biotinylated and labeled pMHC molecules were concentrated to 1 ml in a Millipore ultrafiltration tube. The biotinylated pMHC was purified by gel filtration chromatography. 1 ml of concentrated biotinylated pMHC molecules was loaded on a HiPrep™ 16/60 S200 HR column (GE) pre-equilibrated with filtered PBS using an Akta Purifier (GE) and eluted with PBS at a flow rate of 1 ml/min. The biotinylated pMHC molecules were eluted as a single peak at about 55 ml. The protein-containing fractions were combined and concentrated in a Millipore ultrafiltration tube. The concentration of protein was determined by BCA method (Thermo), protease inhibitor cocktail (Roche) was added and the biotinylated pMHC molecules were dispensed and stored at −80° C.

Example 4. Generation of High-Affinity Single-Chain TCR

Phage display technology is a means to generate high affinity TCR variant libraries for screening high affinity variants. The TCR phage display and screening method described by Li et al. ((2005) Nature Biotech 23(3): 349-354) was applied to the single-chain TCR template of Example 1. A library of high affinity TCRs was established by mutating CDR regions of the template chain and panned. After several rounds of panning, the phage library can specifically bind to the corresponding antigen, the monoclone was picked and sequence analysis was performed.

BIAcore method of Example 3 was used to analyze the interaction between a TCR molecule and SLLMWITQC (SEQ ID NO: 105)-HLA-A2 complex, and a high affinity TCR with affinity and/or binding half-life of at least 2 times that of the wild-type TCR was screened out, that is, the dissociation equilibrium constant $K_D$ of the screened high affinity TCR for binding SLLMWITQC(SEQ ID NO: 105)-HLA-A2 complex is less than or equal to one-half of the dissociation equilibrium constant $K_D$ of the wild type TCR for binding SLLMWITQC(SEQ ID NO: 105)-HLA-A2 complex, and the results are shown in Table 3 below. $K_D$ value of the interaction between the reference TCR and SLLMWITQC(SEQ ID NO: 105)-HLA-A2 complex was detected to be 43 μM by using the above method, and the interaction curve is shown in FIG. 12, that is, $K_D$ value of the wild type TCR interacting with SLLMWITQC(SEQ ID NO: 105)-HLA-A2 complex is 43 μM too (4.3E-05M).

Specifically, when using the numbering shown in SEQ ID NO: 1, an amino acid at one or more of the following sites in the α chain variable domain of these high-affinity TCR mutants mutated: 27T, 28S, 29I, 30N, 51S, 52N, 53E, 54R, 90A, 91T, 93A, 94N, 95G, 96K, 97I and 98I and/or when using the numbering shown in SEQ ID NO: 41, an amino acid at one or more of the following sites in the β chain variable domain of these high-affinity TCR mutants mutated: 51N, 52N, 53V, 54P, 95S, 96L and 98S.

More specifically, when using the numbering shown in SEQ ID NO: 1, the α chain variable domains of these high-affinity TCRs comprise one or more amino acid residues selected from the group consisting of 27G, 28W, 29A or 29V, 30Q, 51T, 52G, 53Q, 54Q or 54A, 90M, 91Y, 93E or 93Q, 94F or 94Y or 94W, 95A or 95Q, 96W or 96R or 96T or 96S or 96M or 96L, 97W or 97V or 97Y or 97P, and 98E or 98N or 98D or 98Q or 98K or 98V or 98G or 98M or 98S; and/or when using the numbering shown in SEQ ID NO: 2, the β chain variable domains of these high-affinity TCRs comprise one or more amino acid residues selected from the group consisting of 51H, 52G, 53A, 54V, 95Q or 95M, 96R or 96K or 96M and 98A or 98G or 98P.

The specific amino acid sequences of α chain variable domains (SEQ ID NOs: 9, 10, 11, 12, 13, 14, 15, 16, 17, 18, 19, 20, 21, 22, 23, 24, 25, 26, 27, 28, 29, 30, 31, 32, 33, 34, 35, 36 and 37) and β chain variable domains (SEQ ID NO: 38, 39, 40, 41, 42, 43, 44 45, 46, 47, 48, 49, 50, 51, 52 and 53) of the high-affinity single-chain TCRs are shown in FIGS. 5(1)-(29) and FIGS. 6(1)-(16), respectively.

TABLE 3

| Single chain TCR numbering | Single chain TCR variable domain (SEQ ID NO.) | | $K_D$(M) |
|---|---|---|---|
| | α | β | |
| s-1 | 9 | 4 | 2.97E-09 |
| s-2 | 10 | 38 | 2.66E-10 |
| s-3 | 11 | 38 | 2.78E-10 |
| s-4 | 11 | 39 | 4.75E-10 |
| s-5 | 11 | 40 | 3.57E-10 |
| s-6 | 12 | 41 | 3.42E-10 |
| s-7 | 13 | 41 | 2.95E-10 |
| s-8 | 14 | 38 | 3.41E-10 |
| s-9 | 15 | 42 | 3.17E-10 |
| s-10 | 16 | 41 | 4.25E-10 |
| s-11 | 17 | 40 | 5.72E-10 |
| s-12 | 3 | 43 | 3.80E-07 |
| s-13 | 3 | 44 | 1.58E-06 |
| s-14 | 3 | 45 | 4.91E-06 |
| s-15 | 3 | 46 | 8.51E-07 |
| s-16 | 3 | 47 | 1.69E-06 |
| s-17 | 3 | 48 | 1.01E-07 |
| s-18 | 3 | 49 | 1.57E-07 |
| s-19 | 18 | 4 | 4.73E-06 |
| s-20 | 19 | 4 | 3.33E-07 |
| s-21 | 20 | 4 | 1.08E-07 |
| s-22 | 21 | 4 | 1.54E-07 |
| s-23 | 22 | 4 | 3.25E-07 |
| s-24 | 23 | 4 | 2.79E-07 |
| s-25 | 24 | 4 | 1.97E-07 |
| s-26 | 25 | 4 | 1.06E-07 |
| s-27 | 26 | 4 | 1.09E-06 |
| s-28 | 27 | 4 | 3.96E-07 |
| s-29 | 28 | 4 | 1.27E-06 |
| s-30 | 29 | 4 | 1.04E-06 |
| s-31 | 30 | 4 | 1.31E-06 |
| s-32 | 31 | 4 | 4.71E-10 |
| s-33 | 32 | 4 | 3.14E-10 |
| s-34 | 33 | 4 | 7.16E-10 |
| s-35 | 34 | 4 | 5.11E-10 |
| s-36 | 10 | 4 | 8.43E-10 |
| s-37 | 14 | 4 | 8.55E-10 |
| s-38 | 35 | 4 | 9.43E-10 |
| s-39 | 36 | 4 | 1.08E-09 |
| s-40 | 37 | 4 | 1.11E-09 |
| s-41 | 3 | 50 | 5.21E-08 |

TABLE 3-continued

| Single chain TCR numbering | Single chain TCR variable domain (SEQ ID NO.) α | β | $K_D(M)$ |
|---|---|---|---|
| s-42 | 3 | 51 | 7.60E−08 |
| s-43 | 3 | 52 | 9.39E−08 |
| s-44 | 3 | 53 | 6.68E−08 |

Example 5. Generation of High-Affinity Up Heterodimeric TCR

The mutations in CDR regions of the high-affinity single-chain TCRs screened in Example 4 were introduced into the corresponding sites of the variable domain of the αβ heterodimeric TCR, and its affinity for SLLMWITQC(SEQ ID NO: 105)-HLA-A2 complex was detected by BIAcore. The mutated sites of high-affinity can be introduced in the above CDR regions by a method of site-directed mutagenesis well known to a skilled person in the art. The amino acid sequences of α chain and β chain variable domain of the above wild type TCR are shown in FIGS. 1a (SEQ ID NO: 1) and 1b (SEQ ID NO: 2), respectively.

It should be noted that in order to obtain a more stable soluble TCR for easier evaluation of the binding affinity and/or binding half-life between the TCR and SLLMWITQC(SEQ ID NO: 105)-HLA A2 complex, the αβ heterodimeric TCR may be such a TCR in which a cysteine residue is respectively introduced into α and β chain constant domain to form an artificial interchain disulfide bond. In this example, the amino acid sequences of TCR α and β chains after introducing a cysteine residue are shown in FIG. 8a (SEQ ID NO: 56) and 8b (SEQ ID NO: 57), and the introduced cysteine residues are indicated by bold letters.

According to standard methods described in Molecular Cloning a Laboratory Manual (3rd edition, Sambrook and Russell), genes of extracellular sequences of the TCR α and β chains to be expressed are synthesized and inserted into an expression vector pET28a+(Novagene), in which the upstream and downstream cloning sites are NcoI and NotI, respectively. Mutations in the CDR regions are introduced by overlap PCR well known to a skilled person in the art. The inserted fragment was sequenced to confirm that it was correct.

Example 6. Expression, Refolding and Purification of Up Heterodimeric TCR

Expression vectors for TCR α and β chain were transformed into the expression bacteria BL21 (DE3) by chemical transformation, respectively. The bacteria were grown in LB medium and induced with a final concentration of 0.5 mM IPTG at $OD_{600}$=0.6. The inclusion bodies formed after the TCR α and β chains were expressed were extracted by BugBuster Mix (Novagene) and repeatedly washed with BugBuster solution. The inclusion bodies were finally dissolved in 6 M guanidine hydrochloride, 10 mM dithiothreitol (DTT), 10 mM ethylenediaminetetraacetic acid (EDTA) and 20 mM Tris (pH 8.1).

The dissolved TCR α and β chains were rapidly mixed in 5 M urea, 0.4 M arginine, 20 mM Tris (pH 8.1), 3.7 mM cystamine, and 6.6 mM β-mercapoethylamine (4° C.) at a mass ratio of 1:1. The final concentration is 60 mg/mL. After mixing, the solution was dialyzed against 10 volumes of deionized water (4° C.), and after 12 hours, deionized water was exchanged with a buffer (20 mM Tris, pH 8.0) and dialysis was continued at 4° C. for 12 hours. After completion of the dialysis, the solution was filtered through a 0.45 pM filter and purified through an anion exchange column (HiTrap Q HP, 5 ml, GE Healthcare). The elution peak of TCR containing successfully refolded a and β dimers was confirmed by SDS-PAGE gel. The TCR was then further purified by gel filtration chromatography (HiPrep 16/60, Sephacryl S-100 HR, GE Healthcare). The purity of the purified TCR was determined by SDS-PAGE to be greater than 90%, and the concentration thereof was determined by BCA method.

Example 7. Results of BIAcore Analysis

The affinity of the αβ heterodimeric TCR, in which a high affinity CDR region was introduced, for SLLMWITQC (SEQ ID NO: 105)-HLA-A2 complex was detected by using the method described in Example 3.

The CDR regions selected from the high-affinity single-chain TCR α and f chain were transferred into the corresponding positions of the wild-type TCR α chain variable domain SEQ ID NO: 1 and β chain variable domain SEQ ID NO: 2, respectively, to form an αβ heterodimeric TCR. The amino acid sequences of resulting new TCR α and β chain variable domains are shown in FIGS. 9(1)-(29) and FIGS. 10(1)-(16), respectively. Since the CDR regions of a TCR molecule determine their affinity for the corresponding pMHC complex, a skilled person in the art can anticipate that an αβ heterodimeric TCR, in which a high affinity mutation site is introduced also has a high affinity for SLLMWITQC(SEQ ID NO: 105)-HLA-A2 complex. The expression vector was constructed by the method described in Example 5, the above-mentioned αβ heterodimeric TCR with a high-affinity mutation being introduced was expressed, refolded and purified by the method described in Example 6, and then the affinity of the TCR for SLLMWITQC(SEQ ID NO: 105)-HLA-A2 complex is determined by BIAcore T200, as shown in Table 4 below.

TABLE 4

| TCR numbering | TCR variable domain (SEQ ID NO) α | β | $K_D(M)$ |
|---|---|---|---|
| 1 | 58 | 2 | 2.90E−10 |
| 2 | 59 | 87 | 1.10E−11 |
| 3 | 60 | 87 | 1.13E−11 |
| 4 | 60 | 88 | 1.43E−11 |
| 5 | 60 | 89 | 1.35E−11 |
| 6 | 61 | 90 | 1.19E−11 |
| 7 | 62 | 90 | 6.63E−12 |
| 8 | 63 | 87 | 8.77E−12 |
| 9 | 64 | 91 | 8.41E−12 |
| 10 | 65 | 90 | 6.05E−12 |
| 11 | 66 | 89 | 9.70E−12 |
| 12 | 1 | 92 | 2.13E−06 |
| 13 | 1 | 93 | 1.72E−06 |
| 14 | 1 | 94 | 1.02E−06 |
| 15 | 1 | 95 | 1.04E−06 |
| 16 | 1 | 96 | 1.60E−06 |
| 17 | 1 | 97 | 3.01E−07 |
| 18 | 1 | 98 | 1.33E−07 |
| 19 | 67 | 2 | 9.69E−07 |
| 20 | 68 | 2 | 2.24E−05 |
| 21 | 69 | 2 | 3.26E−08 |
| 22 | 70 | 2 | 1.12E−07 |
| 23 | 71 | 2 | 3.57E−07 |
| 24 | 72 | 2 | 1.54E−07 |
| 25 | 73 | 2 | 3.10E−07 |
| 26 | 74 | 2 | 1.15E−07 |

TABLE 4-continued

| TCR numbering | TCR variable domain (SEQ ID NO) α | β | $K_D(M)$ |
|---|---|---|---|
| 27 | 75 | 2 | 5.69E−07 |
| 28 | 76 | 2 | 2.97E−07 |
| 29 | 77 | 2 | 5.90E−07 |
| 30 | 78 | 2 | 4.37E−07 |
| 31 | 79 | 2 | 6.86E−07 |
| 32 | 80 | 2 | 2.57E−11 |
| 33 | 81 | 2 | 3.80E−11 |
| 34 | 82 | 2 | 2.17E−11 |
| 35 | 83 | 2 | 4.55E−11 |
| 36 | 59 | 2 | 3.55E−11 |
| 37 | 63 | 2 | 3.03E−11 |
| 38 | 84 | 2 | 3.29E−11 |
| 39 | 85 | 2 | 5.70E−11 |
| 40 | 86 | 2 | 1.13E−10 |
| 41 | 1 | 99 | 1.59E−06 |
| 42 | 1 | 100 | 2.43E−06 |
| 43 | 1 | 101 | 1.04E−06 |
| 44 | 1 | 102 | 7.02E−06 |

As can be seen from Table 4 above, the αβ heterodimeric TCR with mutation sites introduced into CDR regions maintains high affinity for SLLMWITQC(SEQ ID NO: 105)-HLA-A2 complex. The affinity of the heterodimeric TCR for SLLMWITQC(SEQ ID NO: 105)-HLA-A2 complex is at least 2 times of that of the wild-type TCR.

Example 8. Expression, Refolding and Purification of Fusions of Anti-CD3 Antibodies with High-Affinity Single-Chain TCR The high-affinity single-chain TCR molecule of the present invention is fused with a single-chain molecule (scFv) of an anti-CD3 antibody to construct a fusion molecule. Primers were designed by overlapping PCR, and the genes of anti-CD3 antibodies and high-affinity single-chain TCR molecule were ligated. The intermediate linker was designed as GGGGS, and the gene fragment of the fusion molecule had restriction enzyme sites NcoI and NotI. The PCR amplification product was digested with NcoI and NotI and ligated with pET28a vector digested with NcoI and NotI. The ligation product was transformed into E. coli DH5α competent cells, and plated on LB plate containing kanamycin and inverted and cultured overnight at 37° C. Positive clones were picked for PCR screening, and the positive recombinants were sequenced to determine the correct sequence. The recombinant plasmids were extracted and transformed into E. coli BL21 (DE3) competent cells for expression.

Expression of Fusion Protein

The expression plasmid containing the gene of interest was transformed into E. coli strain BL21 (DE3), plated on a LB plate (kanamycin, 50 μg/ml) and cultured at 37° C. overnight. On the next day, the clones were picked and inoculated into 10 ml of LB liquid medium (kanamycin, 50 g/ml), cultured for 2-3 h, then inoculated to 1 L of LB medium (kanamycin, 50 μg/ml) at a volume ratio of 1:100, cultured until the $OD_{600}$ was 0.5-0.8, and then induced to express the protein of interest using IPTG at a final concentration of 0.5 mM. 4 hours after induction, the cells were harvested by centrifugation at 6000 rpm for 10 min. The cells were washed once in PBS buffer, and dispensed. Cells corresponding to 200 ml of the bacterial culture were taken and lysed with 5 ml of BugBuster Master Mix (Novagen), and the inclusion bodies were collected by centrifugation at 6000 g for 15 minutes. The inclusion bodies were washed for 4 times with detergent to remove cell debris and membrane components. The inclusion bodies are then washed with a buffer such as PBS to remove detergent and salt. Finally, the inclusion bodies were dissolved in Tris buffer solution containing 8 M urea, the concentration of inclusion bodies was measured, and inclusion bodies were dispensed and cryopreserved at −80° C.

Refolding of Fusion Proteins

About 10 mg of inclusion bodies were taken from a −80° C. ultra-low temperature freezer and thawed, and dithiothreitol (DTT) was added to a final concentration of 10 mM, and incubated at 37° C. for 30 min to 1 hour to ensure complete opening of the disulfide bond. The solution of inclusion body sample was then added dropwise into 200 ml of 4° C. pre-cooled refolding buffer (100 mM Tris pH 8.1, 400 mM L-arginine, 2 mM EDTA, 5 M urea, 6.5 mM β-mercaptoethylamine, 1.87 mM Cystamine), respectively, and stirred slowly at 4° C. for about 30 minutes. The refolding solution was dialyzed against 8 volumes of pre-cooled $H_2O$ for 16-20 hours. It was further dialyzed twice with 8 volumes of 10 mM Tris pH 8.0, and dialysis was continued at 4° C. for about 8 hours. After dialysis, the sample was filtered and subjected to the following purification process.

First Step Purification of Fusion Protein

The dialyzed and refolded material (in 10 mM Tris pH 8.0) was eluted on a POROS HQ/20 anion exchange chromatography prepacked column (Applied Biosystems) with a gradient of 0-600 mM NaCl using AKTA Purifier (GE Healthcare). Each component was analyzed by Coomassie brilliant blue stained SDS-PAGE and then combined.

Second Step Purification of the Fusion Protein

The purified and combined sample solution from the first step was concentrated for purification in this step, and the fusion protein was purified by Superdex 75 10/300 GL gel filtration chromatography prepacked column (GE Healthcare) pre-equilibrated in PBS buffer. The components of the peaks were analyzed by Coomassie Brilliant Blue-stained SDS-PAGE and then combined.

Example 9. Expression, Refolding and Purification of Fusions of Anti-CD3 Antibody with High-Affinity Up Heterodimeric TCR A fusion molecule was prepared by fusing an anti-CD3 single-chain antibody (scFv) with an αβ heterodimeric TCR. The anti-CD3 scFv was fused with β chain of the TCR, and the TCR β chain may comprise β chain variable domain of any of the above high-affinity αβ heterodimeric TCRs, and the TCR α chain of the fusion molecule may comprise α chain variable domain of any of the above high-affinity αβ heterodimeric TCR.

Construction of Expression Vector for Fusion Molecule

1. Construction of expression vector for α chain

The target gene carrying α chain of the αβ heterodimeric TCR was digested with NcoI and NotI, and ligated with pET28a vector digested with NcoI and NotI. The ligation product was transformed into E. coli DH5α, plated on a LB plate containing kanamycin, and inverted and cultured overnight at 37° C. Positive clones were picked for PCR screening, and the positive recombinants were sequenced to determine the correct sequence. The recombinant plasmids were extracted and transformed into E. coli Tuner (DE3) for expression.

2. Construction of expression vector for anti-CD3 (scFv)-β chain

Primers were designed by overlapping PCR to ligate the anti-CD3 scFv and the high-affinity heterodimeric TCRβ chain gene, the intermediate linker was GGGGS, and the gene fragment of the fusion protein of anti-CD3 scFv and the high-affinity heterodimeric TCRβ chain had the restriction endonuclease sites NcoI (CCATGG, SEQ ID NO: 147) and NotI (GCGGCCGC, SEQ ID NO: 148). The PCR amplification product was digested with NcoI and NotI and ligated with pET28a vector digested with NcoI and NotI. The ligation product was transformed into E. coli DH5α competent cells, plated on a kanamycin-containing LB plate, and inverted and cultured overnight at 37° C. Positive clones were picked for PCR screening, and the positive recombinants were sequenced to determine the correct sequence. The recombinant plasmids were extracted and transformed into E. coli Tuner (DE3) competent cells for expression.

Expression, refolding and purification of fusion protein

The expression plasmids were separately transformed into E. coli Tuner (DE3) competent cells, plated on LB plates (kanamycin 50 μg/mL) and cultured overnight at 37° C. On the next day, clones were picked and inoculated into 10 mL LB liquid medium (kanamycin 50 μg/mL) for 2-3 h, and inoculated into 1 L LB medium at a volume ratio of 1:100, the culture was continued until the $OD_{600}$ was 0.5-0.8, and a final concentration of 1 mM IPTG was added to induce expression of the protein of interest. After 4 hours, cells were harvested by centrifugation at 6000 rpm for 10 mins. The cells were washed once in PBS buffer and were dispensed, and cells corresponding to 200 mL of the bacterial culture were taken and lysed with 5 mL of BugBuster Master Mix (Merck), inclusion bodies were collected by centrifugation at 6000 g for 15 min and then washed with detergent for 4 times to remove cell debris and membrane components. The inclusion bodies were then washed with a buffer such as PBS to remove detergent and salt. Finally, the inclusion bodies were dissolved in 6M guanidine hydrochloride, 10 mM dithiothreitol (DTT), 10 mM ethylenediaminetetraacetic acid (EDTA), 20 mM Tris, pH 8.1 buffer solution, and the concentration of inclusion bodies was determined. The inclusion bodies were dispensed and cryopreserved at −80° C.

The dissolved TCRα chain and anti-CD3 (scFv)-β chain were rapidly mixed in a mass ratio of 2:5 in 5 M urea (urea), 0.4 M L-arginine (L-arginine), 20 mM Tris pH 8.1, 3.7 mM cystamine, and 6.6 mM β-mercapoethylamine (4° C.), and the final concentrations of α chain and anti-CD3 (scFv)-β chain were 0.1 mg/mL, 0.25 mg/mL, respectively.

After mixing, the solution was dialyzed against 10 volumes of deionized water (4° C.), and after 12 hours, deionized water was exchanged with buffer (10 mM Tris, pH 8.0) for another 12 hours at 4° C. After completion of dialysis, the solution was filtered through a 0.45 pM filter and purified by an anion exchange column (HiTrap Q HP 5 ml, GE healthcare). The eluted peaks containing the reconstituted TCR α chain and anti-CD3 (scFv)-β chain dimer TCR were confirmed by SDS-PAGE gel. The TCR fusion molecule was then purified by size exclusion chromatography (S-100 16/60, GE healthcare) and further purified by an anion exchange column (HiTrap Q HP 5 ml, GE healthcare). The purity of the purified TCR fusion molecule was determined by SDS-PAGE to be greater than 90%, and the concentration was determined by BCA method.

Example 10. Activation Function Assay of Effector Cells Transfected with High Affinity TCR of the Present Invention This example demonstrates that effector cells transfected with the high affinity TCR of the present invention have a good specific activation effect on target cells.

The function and specificity of the high affinity TCR of the present invention in cells were examined by ELISPOT assay. Methods for detecting cellular function using ELISPOT assays are well known to a skilled person in the art. In the IFN-γ ELISPOT assay of this example, CD8$^+$ T cells isolated from the blood of healthy volunteers and transfected with TCR using lentivirus were used as effector cells, and labeled as TCR1 (α chain variable domain SEQ ID NO: 67, β chain variable domain SEQ ID NO: 2) and TCR2 (α chain variable domain SEQ ID NO: 68, β chain variable domain SEQ ID NO: 2) respectively. In the control group, effector cells were labeled as WT-TCR (transfected with wild-type TCR) and GFP (transfected with GFP). The target cell lines were A375, Mel624, Mel526 and NCI-H1650 cells, in which the target cell lines A375 and Mel624 expressed related antigens, and Mel526 and NCI-H1650, as controls, did not express related antigens.

Figure 13:
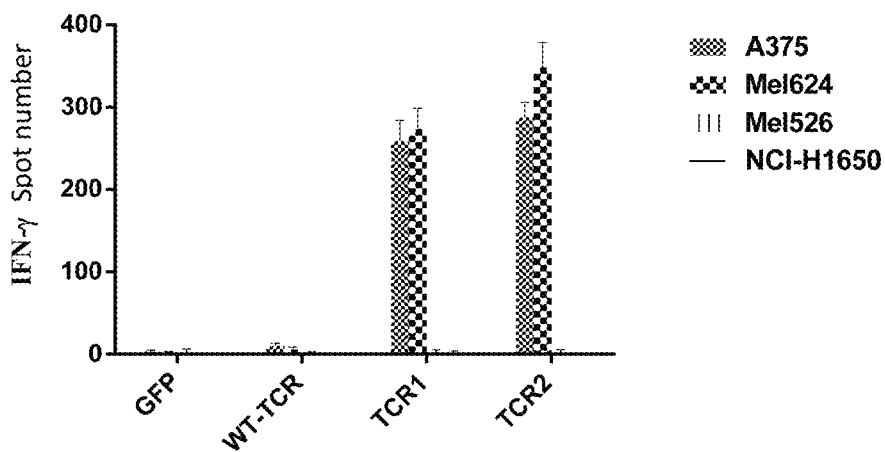
FIG. 13 shows results of INF-γ activation experiment of effector cells transfected with the high affinity TCR of the present invention.

Firstly, a ELISPOT plate was prepared. The ELISPOT plate was activated and coated with ethanol overnight at 4° C. On the first day of the experiment, the coating solution was removed, and the plate was washed, blocked and incubated at room temperature for 2 hrs, and the blocking solution was removed. Components of the assay were added to the ELISPOT plate in the following order: the medium for adjusting effector cells to 1×10$^5$ cells/ml, and the medium for adjusting each target cell line to 2×10$^5$ cells/ml. After homogeneously mixing, 100 μL of target cell line 2×10$^5$ cells/ml (i.e., 20,000 cells/well) and 100 μL of effector cells 1×10$^5$ cells/ml (i.e., 10,000 cells/well) were added to the corresponding wells in duplicate, and incubate overnight (37° C., 5% $CO_2$). On the second day of the experiment, the plate was washed, subjected to a secondary detection and development, and dried, and the spots formed on the film were counted using an immunospot plate reader (ELISPOT READER system; AID20 company). Experimental results are shown in FIG. 13, in which the effector cells transfected with the high affinity TCR of the present invention exhibit excellent specific activation effects on target cells.

Example 11. Killing Function Assay of Effector Cells Transfected with High Affinity TCR of the Present Invention In this example, the release of LDH was determined by non-radioactive cytotoxicity assay to verify the killing function of cells transducing the TCR of the present invention. The assay is a colorimetric substitution assay for 51Cr release cytotoxicity assay to quantify lactate dehydrogenase (LDH) released after cell lysis. LDH released in the medium was detected using a 30 minute-coupled enzyme reaction, in which LDH converts tetrazolium salt (INT) into red formazan. The amount of produced red product is directly proportional to the number of lysed cells. Absorbance data of visible light at 490 nm can be collected using a standard 96-well plate reader.

Methods for detecting cellular function using LDH release assay are well known to a skilled person in the art. In the LDH experiment of this example, PBL cells isolated from the blood of healthy volunteers transfected with TCR by lentivirus were used as effector cells. The target cell lines were A375 (3525), MEL624 (1605), NCI-H1650 (2) and MEL526 (4) cells, in which, A375 (3525) and MEL624 (1605) expressed NY-ESO-1 antigen, and NCI-H1650(2) and MEL526(4), as controls, did not substantially express NY-ESO-1 antigen.

Figure 14:
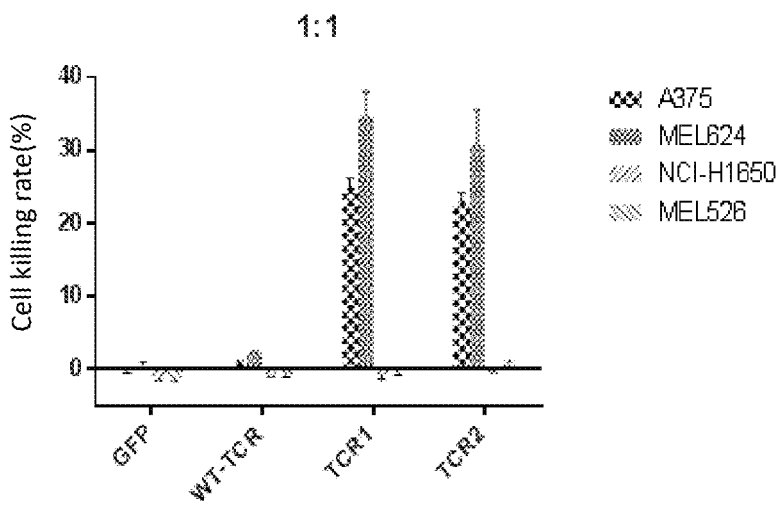
FIG. 14 shows results of killing experiment of effector cells transfected with the high affinity TCR of the present invention on target cells.

Firstly, a LDH plate was prepared. On the first day of the experiment, components of the assay were added to the plate in the following order: the medium for adjusting effect cells to $2 \times 10^6$ cells/ml, and the medium for adjusting each target cell line to $5 \times 10^5$ cells/ml. After homogeneously mixing, 100 μL of target cell line $5 \times 10^5$ cells/ml (i.e., 50,000 cells/well) and 100 μL of effector cells $2 \times 10^6$ cells/ml (i.e., 200,000 cells/well) were added to the corresponding wells in thriplicate. Wells for spontaneous effector cells, for spontaneous target cells, for maximium target cells, for volume-corrected control and for medium background control were simultaneously set. The plate was incubated overnight (37° C., 5% $CO_2$). On the second day of the experiment, color development was detected, and after the reaction was terminated, the absorbance at 490 nm was recorded using a microplate reader (Bioteck). Experiment results are shown in FIG. 14, in which cells transduced with the TCR of the present invention exhibit strong killing effects on target cells expressing the relevant antigen, but have no killing effects on target cells not expressing the relevant antigen.

Example 12. Functional Assay of Fusion Protein of High Affinity TCR of the Present Invention and Anti-CD3 Antibody This example demonstrates that the fusion protein of the high affinity TCR of the present invention and anti-CD3 antibody is capable of redirecting effector cells and exhibits good activation effects.

Methods for detecting cellular function using ELISPOT assays are well known to a skilled person in the art. The effector cells used in IFN-γ ELISPOT assay of this example were CD8+ T cells isolated from the blood of healthy volunteers. The target cell lines were IM9 and 293T, wherein IM9 expressed the relevant antigen and 293T did not express the relevant antigen. The high affinity TCR of the present invention was randomly selected and the fusion protein was prepared as described in Example 8. Specifically, α and β chains of the selected high affinity TCR were as follows: α chain SEQ ID NO: 14, β chain SEQ ID NO: 38; α chain SEQ ID NO: 17, β chain SEQ ID NO: 40; α chain SEQ ID NO: 13, β chain SEQ ID NO: 41; α chain SEQ ID NO: 11, β chain SEQ ID NO: 40; α chain SEQ ID NO: 15, β chain SEQ ID NO: 42; α chain SEQ ID NO: 16, β chain SEQ ID NO: 41; α chain SEQ ID NO: 11, β chain SEQ ID NO: 38; SEQ ID NO: 11, β chain SEQ ID NO: 39; α chain SEQ ID NO: 10, β chain SEQ ID NO: 38; and α chain SEQ ID NO: 12, β chain SEQ ID NO: 41.

Figure 15A:
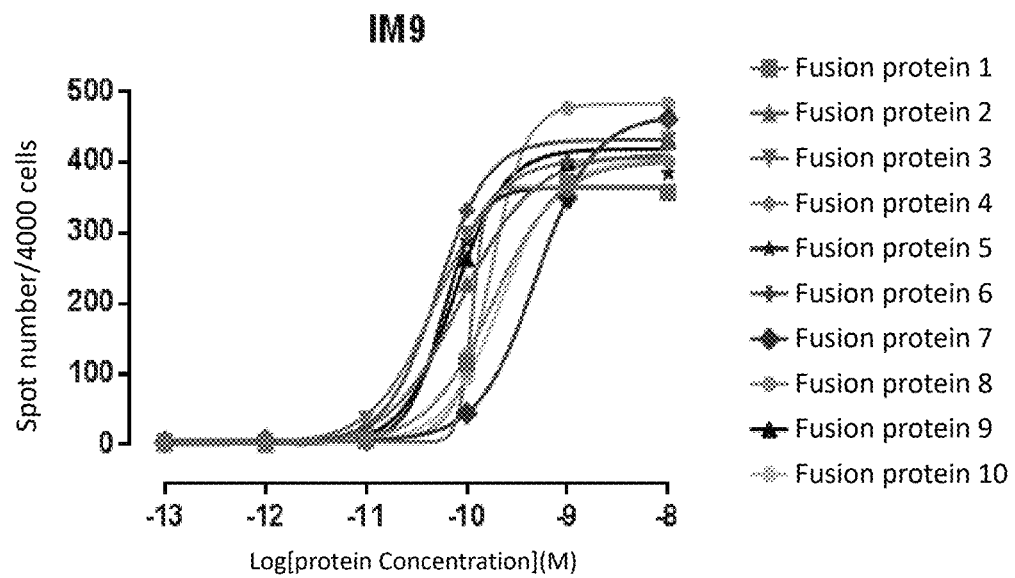
FIGS. 15a and 15b show results of redirection experiments of fusion proteins on effector cells.
Figure 15B:
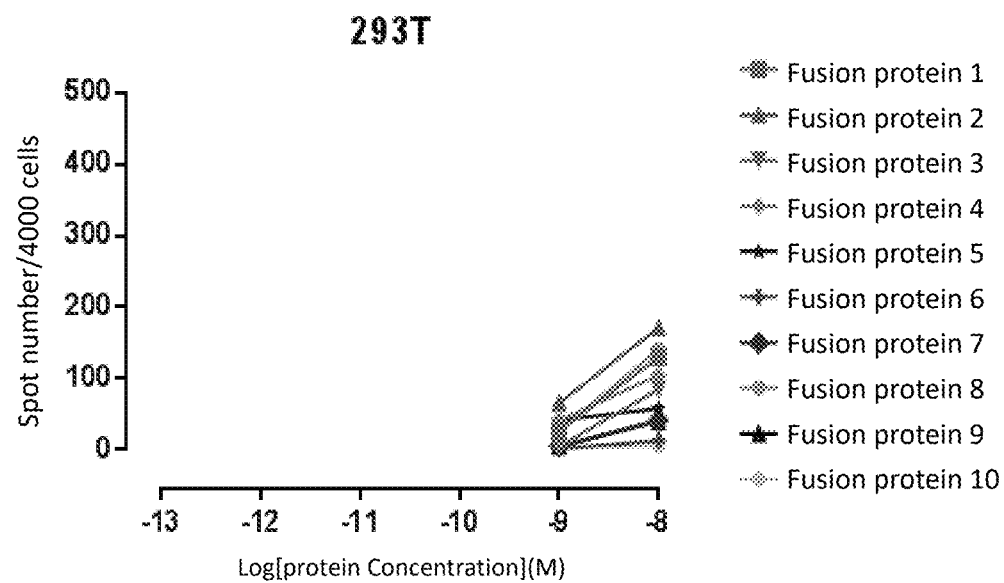

Firstly, a ELISPOT plate was prepared. ELISPOT plate was activated and coated with ethanol, and incubated overnight at 4° C. On the first day of the experiment, the coating solution was removed, and the plate was washed, blocked and incubated at room temperature for two hours, and the blocking solution was removed. Components of the assay were added to the ELISPOT plate in the following order: medium for adjusting CD8+ T cells to $2 \times 10^4$ cells/ml, medium for adjusting each target cell line to $2 \times 10^5$ cells/ml, and medium for diluting the fusion protein to a concentration of 0.04 μM (serially diluted by 10 times, for a total of 6 concentration gradients). After homogeneously mixing, 50 μL of fusion protein dilution, 50 μL of target cell line $2 \times 10^5$ cells/ml (i.e., 10,000 cells/well) and 100 μL of effector cells $2 \times 10^4$ cells/ml (i.e., 2,000 effect cells/well) were taken and added to the corresponding wells in duplicate. The plate was incubated overnight (37° C., 5% $CO_2$). On the second day of the experiment, the plate was washed and subjected to secondary detection and color development. The plate was dried, and the spots formed on the film were counted using an immunospot plate reader (ELISPOT READER system; AID20 company). Experiment results are shown in FIGS. 15*a* and 15*b*, and the fusion protein of the high affinity TCR of the present invention and anti-CD3 antibody is capable of redirecting effector cells and exhibits good activation effects.

Example 13. In Vivo Efficacy of High Affinity TCR Molecule of the Invention

T cells transfected with the high affinity TCR of the present invention were injected into mice of human melanoma xenograft model to test the inhibitory effects thereof on tumors in vivo.

In the experiment, NSG mice (Nanjing University-Nanjing Institute of Biomedical Research) (female, 6-8 weeks old) were used as the experimental subjects. 10 days before the start of the experiment, A375 tumor cells (ATCC) which was cultured, collected and suspended were subcutaneously injected into one side of abdomen of the mice at $3*10^6$ cells/mouse (injection volume 200 ul) to establish human melanoma xenograft mouse model.

On the day of the experiment, the long diameter (a) and the short diameter (b) of the formed tumor of each mouse were measured with a vernier caliper, and the tumor volume was calculated according to the following formula: $V=a*b^2/2$. Then the mice were divided into: 5 in the PBS group, 7 in the control group (T cells transfected with irrelevant TCR), 10 in the group of T cells transfected with TCR1 (α chain variable domain SEQ ID NO: 67, β chain variable domain SEQ ID NO: 2) and 10 in the group of T cells transfected with TCR2 (α chain variable domain SEQ ID NO: 68, β chain variable domain SEQ ID NO: 2), and were randomly grouped according to tumor volume. After grouping, the prepared T cells were injected into the mice of the above groups via tail vein at $1*10^7$/mouse, respectively, and the mice in the PBS group were intravenously injected with 100 ul of PBS via tail vein.

After the injection of TCR-T cells, 100 ul of prepared IL-2 solution (50000 IU/100 UL) was taken and intraperitoneally injected into each mouse, followed by continuous injection of the same amount of IL-2 solution every day for 4 days. From the beginning of the experiment, the tumor diameter of the mouse was measured every 3 days and the volume of the tumor was calculated according to the above method until the action of the mouse were affected due to excessive tumor or the tumor regressed. The above data were compiled and the tumor volumes of mice in each group were statistically analyzed.

Figure 16:
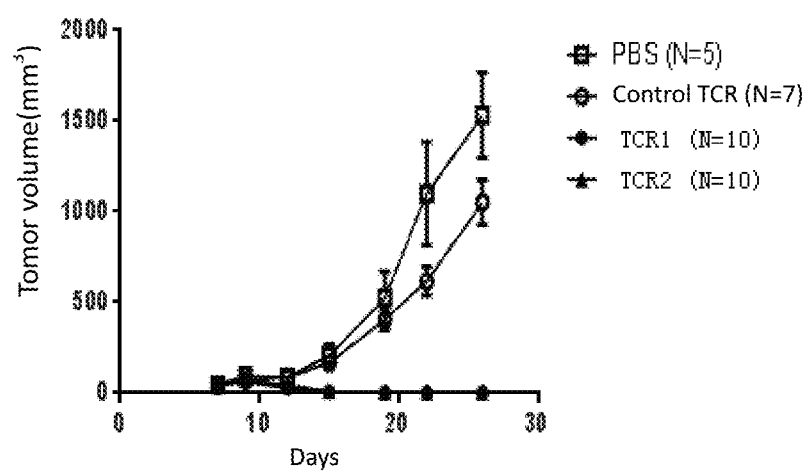
FIG. 16 shows results of in vivo efficacy of effector cells transfected with the high affinity TCR of the present invention.

The obtained experiment results are shown in FIG. 16. In the group of mice injected with the T cells transfected with the high affinity TCR of the present invention, the growth of the tumor was significantly inhibited and showed a tendency to shrink, while in the group of mice injected with the T cells transfected with irrelevant TCR and the group of mice injected with PBS, the tumor volume increased quickly.

All documents mentioned in the present application are hereby incorporated by reference in their entireties, as if each is incorporated by reference. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A T cell receptor (TCR), which has an activity of binding to SLLMWITQC (SEQ ID NO: 105)-HLA A2 complex and comprises a TCR α chain variable domain and a TCR β chain variable domain, the TCRα chain variable domain comprising three CDR regions, and the TCR β chain variable domain comprising three CDR regions, wherein the TCR is selected from the group consisting of TCR No. 1 to TCR No. 44, having six CDRs as shown below:

| TCR No. | CDR1α | CDR2α | CDR3α | CDR1β | CDR2β | CDR3β |
|---|---|---|---|---|---|---|
| 1 | TSINN (SEQ ID NO: 106) | IRSNERE (SEQ ID NO: 107) | ATDAFAWWI (SEQ ID NO: 115) | SGHDY (SEQ ID NO: 109) | FNNNVP (SEQ ID NO: 110) | ASSLGSNEQY (SEQ ID NO: 111) |
| 2 | GWAQN (SEQ ID NO: 118) | IRTGEQE (SEQ ID NO: 120) | ATDANARWN (SEQ ID NO: 112) | SGHDY (SEQ ID NO: 109) | FNHGAV (SEQ ID NO: 122) | ASSLGSNEQY (SEQ ID NO: 111) |
| 3 | GSIQN (SEQ ID NO: 117) | IRTGEQE (SEQ ID NO: 120) | ATDANARWE (SEQ ID NO: 113) | SGHDY (SEQ ID NO: 109) | FNHGAV (SEQ ID NO: 122) | ASSLGSNEQY (SEQ ID NO: 111) |
| 4 | GSIQN (SEQID NO: 117) | IRTGEQE (SEQ ID NO: 120) | ATDANARWE (SEQ ID NO: 113) | SGHDY (SEQ ID NO: 109) | FNHGAV (SEQ ID NO: 122) | ASQRGSNEQY (SEQ ID NO: 123) |
| 5 | GSIQN (SEQ ID NO: 117) | IRTGEQE (SEQ ID NO: 120) | ATDANARWE (SEQ ID NO: 113) | SGHDY (SEQ ID NO: 109) | FNHGAV (SEQ ID NO: 122) | ASQKGANEQY (SEQ ID NO: 124) |
| 6 | GSIQN (SEQ ID NO: 117) | IRTGEQE (SEQ ID NO: 120) | ATDANARWD (SEQ ID NO: 114) | SGHDY (SEQ ID NO: 109) | FNHGAV (SEQ ID NO: 122) | ASQLGSNEQY (SEQ ID NO: 125) |
| 7 | GWAQN (SEQ ID NO: 118) | IRSNERE (SEQ ID NO: 107) | ATDANARWN (SEQ ID NO: 112) | SGHDY (SEQ ID NO: 109) | FNHGAV (SEQ ID NO: 122) | ASQLGSNEQY (SEQ ID NO: 125) |
| 8 | GWVQN (SEQ ID NO: 119) | IRTGEQE (SEQ ID NO: 120) | ATDANARWD (SEQ ID NO: 114) | SGHDY (SEQ ID NO: 109) | FNHGAV (SEQ ID NO: 122) | ASSLGSNEQY (SEQ ID NO: 111) |
| 9 | GSIQN (SEQ ID NO: 117) | IRSNERE (SEQ ID NO: 107) | ATDANARWD (SEQ ID NO: 114) | SGHDY (SEQ ID NO: 109) | FNHGAV (SEQ ID NO: 122) | ASQLGANEQY (SEQ ID NO: 126) |
| 10 | GWAQN (SEQ ID NO: 118) | IRSNERE (SEQ ID NO: 107) | ATDANARWD (SEQ ID NO: 114) | SGHDY (SEQ ID NO: 109) | FNHGAV (SEQ ID NO: 122) | ASQLGSNEQY (SEQ ID NO: 125) |
| 11 | GSIQN (SEQ ID NO: 117) | IRSNERE (SEQ ID NO: 107) | ATDANARWE (SEQ ID NO: 113) | SGHDY (SEQ ID NO: 109) | FNHGAV (SEQ ID NO: 122) | ASQKGANEQY (SEQ ID NO: 124) |
| 12 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQLGGNEQY (SEQ ID NO: 127) |
| 13 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQKGANEQY (SEQ ID NO: 124) |
| 14 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQLGPNEQY (SEQ ID NO: 128) |
| 15 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQRGANEQY (SEQ ID NO: 129) |
| 16 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQMGSNEQY (SEQ ID NO: 130) |
| 17 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQLGSNEQY (SEQ ID NO: 125) |
| 18 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQLGANEQY (SEQ ID NO: 126) |

-continued

| TCR No. | CDR1α | CDR2α | CDR3α | CDR1β | CDR2β | CDR3β |
|---|---|---|---|---|---|---|
| 19 | TSINN (SEQ ID NO: 106) | IRSNERE (SEQ ID NO: 107) | MYDENGKII (SEQ ID NO: 133) | SGHDY (SEQ ID NO: 109) | FNNNVP (SEQ ID NO: 110) | ASSLGSNEQY (SEQ ID NO: 111) |
| 20 | TSINN (SEQ ID NO: 106) | IRSNERE (SEQ ID NO: 107) | MYDQNGKII (SEQ ID NO: 134) | SGHDY (SEQ ID NO: 109) | FNNNVP (SEQ ID NO: 110) | ASSLGSNEQY (SEQ ID NO: 111) |
| 21 | TSINN (SEQ ID NO: 106) | IRSNERE (SEQ ID NO: 107) | ATDAYGTVQ (SEQ ID NO: 135) | SGHDY (SEQ ID NO: 109) | FNNNVP (SEQ ID NO: 110) | ASSLGSNEQY (SEQ ID NO: 111) |
| 22 | TSINN (SEQ ID NO: 106) | IRSNERE (SEQ ID NO: 107) | ATDANGTVQ (SEQ ID NO: 136) | SGHDY (SEQ ID NO: 109) | FNNNVP (SEQ ID NO: 110) | ASSLGSNEQY (SEQ ID NO: 111) |
| 23 | TSINN (SEQ ID NO: 106) | IRSNERE (SEQ ID NO: 107) | ATDANGSVQ (SEQ ID NO: 137) | SGHDY (SEQ ID NO: 109) | FNNNVP (SEQ ID NO: 110) | ASSLGSNEQY (SEQ ID NO: 111) |
| 24 | TSINN (SEQ ID NO: 106) | IRSNERE (SEQ ID NO: 107) | ATDAYGRYI (SEQ ID NO: 138) | SGHDY (SEQ ID NO: 109) | FNNNVP (SEQ ID NO: 110) | ASSLGSNEQY (SEQ ID NO: 111) |
| 25 | TSINN (SEQ ID NO: 106) | IRSNERE (SEQ ID NO: 107) | ATDANQMWK (SEQ ID NO: 139) | SGHDY (SEQ ID NO: 109) | FNNNVP (SEQ ID NO: 110) | ASSLGSNEQY (SEQ ID NO: 111) |
| 26 | TSINN (SEQ ID NO: 106) | IRSNERE (SEQ ID NO: 107) | ATDAYGLPI (SEQ ID NO: 140) | SGHDY (SEQ ID NO: 109) | FNNNVP (SEQ ID NO: 110) | ASSLGSNEQY (SEQ ID NO: 111) |
| 27 | TSINN (SEQ ID NO: 106) | IRSNERE (SEQ ID NO: 107) | ATDANGLPV (SEQ ID NO: 141) | SGHDY (SEQ ID NO: 109) | FNNNVP (SEQ ID NO: 110) | ASSLGSNEQY (SEQ ID NO: 111) |
| 28 | TSINN (SEQ ID NO: 106) | IRSNERE (SEQ ID NO: 107) | ATDANGRWE (SEQ ID NO: 142) | SGHDY (SEQ ID NO: 109) | FNNNVP (SEQ ID NO: 110) | ASSLGSNEQY (SEQ ID NO: 111) |
| 29 | TSINN (SEQ ID NO: 106) | IRSNERE (SEQ ID NO: 107) | ATDANGTVG (SEQ ID NO: 143) | SGHDY (SEQ ID NO: 109) | FNNNVP (SEQ ID NO: 110) | ASSLGSNEQY (SEQ ID NO: 111) |
| 30 | TSINN (SEQ ID NO: 106) | IRSNERE (SEQ ID NO: 107) | ATDANGRWM (SEQ ID NO: 144) | SGHDY (SEQ ID NO: 109) | FNNNVP (SEQ ID NO: 110) | ASSLGSNEQY (SEQ ID NO: 111) |
| 31 | TSINN (SEQ ID NO: 106) | IRSNERE (SEQ ID NO: 107) | ATDANGLWS (SEQ ID NO: 145) | SGHDY (SEQ ID NO: 109) | FNNNVP (SEQ ID NO: 110) | ASSLGSNEQY (SEQ ID NO: 111) |
| 32 | GWAQN (SEQ ID NO: 118) | IRTGEQE (SEQ ID NO: 120) | ATDANARWD (SEQ ID NO: 114) | SGHDY (SEQ ID NO: 109) | FNNNVP (SEQ ID NO: 110) | ASSLGSNEQY (SEQ ID NO: 111) |
| 33 | GWAQN (SEQ ID NO: 118) | IRTGQAE (SEQ ID NO: 121) | ATDANARWE (SEQ ID NO: 113) | SGHDY (SEQ ID NO: 109) | FNNNVP (SEQ ID NO: 110) | ASSLGSNEQY (SEQ ID NO: 111) |
| 34 | GSIQN (SEQ ID NO: 117) | IRSNERE (SEQ ID NO: 107) | ATDAFAWWI (SEQ ID NO: 115) | SGHDY (SEQ ID NO: 109) | FNNNVP (SEQ ID NO: 110) | ASSLGSNEQY (SEQ ID NO: 111) |
| 35 | GWVQN (SEQ ID NO: 119) | IRTGEQE (SEQ ID NO: 120) | ATDANARWN (SEQ ID NO: 112) | SGHDY (SEQ ID NO: 109) | FNNNVP (SEQ ID NO: 110) | ASSLGSNEQY (SEQ ID NO: 111) |
| 36 | GWAQN (SEQ ID NO: 118) | IRTGEQE (SEQ ID NO: 120) | ATDANARWN (SEQ ID NO: 112) | SGHDY (SEQ ID NO: 109) | FNNNVP (SEQ ID NO: 110) | ASSLGSNEQY (SEQ ID NO: 111) |
| 37 | GWVQN (SEQ ID NO: 119) | IRTGEQE (SEQ ID NO: 120) | ATDANARWD (SEQ ID NO: 114) | SGHDY (SEQ ID NO: 109) | FNNNVP (SEQ ID NO: 110) | ASSLGSNEQY (SEQ ID NO: 111) |

-continued

| TCR No. | CDR1α | CDR2α | CDR3α | CDR1β | CDR2β | CDR3β |
|---|---|---|---|---|---|---|
| 38 | GSIQN (SEQ ID NO: 117) | IRTGEQE (SEQ ID NO: 120) | ATDAWARWI (SEQ ID NO: 146) | SGHDY (SEQ ID NO: 109) | FNNNVP (SEQ ID NO: 110) | ASSLGSNEQY (SEQ ID NO: 111) |
| 39 | GWVQN (SEQ ID NO: 119) | IRTGQAE (SEQ ID NO: 121) | ATDANARWE (SEQ ID NO: 113) | SGHDY (SEQ ID NO: 109) | FNNNVP (SEQ ID NO: 110) | ASSLGSNEQY (SEQ ID NO: 111) |
| 40 | GSIQN (SEQ ID NO: 117) | IRTGEQE (SEQ ID NO: 120) | ATDANARWN (SEQ ID NO: 112) | SGHDY (SEQ ID NO: 109) | FNNNVP (SEQ ID NO: 110) | ASSLGSNEQY (SEQ ID NO: 111) |
| 41 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQMGSNEQY (SEQ ID NO: 130) |
| 42 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQRGSNEQY (SEQ ID NO: 123) |
| 43 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASQMGANEQY (SEQ ID NO: 131) |
| 44 | TSINN (SEQ ID NO: 106) | IRSNERE (SEQ ID NO: 107) | ATDANGKII (SEQ ID NO: 108) | SGHDY (SEQ ID NO: 109) | FNNNVP (SEQ ID NO: 110) | ASMLGSNEQY (SEQ ID NO: 132). |

2. The TCR of claim 1, wherein the TCR is soluble.

3. The TCR of claim 1, wherein the TCR is an αβ heterodimeric TCR.

4. The TCR of claim 3, wherein the TCR comprises (i) all or part of the TCR α chain other than its transmembrane domain, and (ii) all or part of the TCR β chain other than its transmembrane domain, wherein both of (i) and (ii) comprise the variable domain and at least a portion of the constant domain of the TCR chain.

5. The TCR of claim 1, wherein the amino acid sequence of the α chain variable domain of the TCR is selected from the group consisting of: SEQ ID NOs: 58-86; and/or the amino acid sequence of the β chain variable domain of the TCR is selected from the group consisting of: SEQ ID NOs: 87-102.

6. The TCR of claim 1, wherein the α chain variable domain and β chain variable domain of the TCR has sequences as shown below:

| TCR number | Sequence of α chain variable domain SEQ ID NO: | Sequence of β chain variable domain SEQ ID NO: |
|---|---|---|
| 1 | 58 | 2 |
| 2 | 59 | 87 |
| 3 | 60 | 87 |
| 4 | 60 | 88 |
| 5 | 60 | 89 |
| 6 | 61 | 90 |
| 7 | 62 | 90 |
| 8 | 63 | 87 |
| 9 | 64 | 91 |
| 10 | 65 | 90 |
| 11 | 66 | 89 |
| 12 | 1 | 92 |
| 13 | 1 | 93 |
| 14 | 1 | 94 |
| 15 | 1 | 95 |
| 16 | 1 | 96 |
| 17 | 1 | 97 |
| 18 | 1 | 98 |
| 19 | 67 | 2 |
| 20 | 68 | 2 |
| 21 | 69 | 2 |
| 22 | 70 | 2 |
| 23 | 71 | 2 |
| 24 | 72 | 2 |
| 25 | 73 | 2 |
| 26 | 74 | 2 |
| 27 | 75 | 2 |
| 28 | 76 | 2 |
| 29 | 77 | 2 |
| 30 | 78 | 2 |
| 31 | 79 | 2 |
| 32 | 80 | 2 |
| 33 | 81 | 2 |
| 34 | 82 | 2 |
| 35 | 83 | 2 |
| 36 | 59 | 2 |
| 37 | 63 | 2 |
| 38 | 84 | 2 |
| 39 | 85 | 2 |
| 40 | 86 | 2 |
| 41 | 1 | 99 |
| 42 | 1 | 100 |
| 43 | 1 | 101 |
| 44 | 1 | 102. |

7. The TCR of claim 1, wherein the TCR is a single chain TCR, wherein the TCR has α chain variable domain and β chain variable domain and is selected from the group consisting of TCR No. s-1 to TCR No. s-44 as shown below:

| TCR Number | Sequence of α chain variable domain SEQ ID NO: | Sequence of β chain variable domain SEQ ID NO: |
|---|---|---|
| s-1 | 9 | 4 |
| s-2 | 10 | 38 |
| s-3 | 11 | 38 |
| s-4 | 11 | 39 |
| s-5 | 11 | 40 |
| s-6 | 12 | 41 |
| s-7 | 13 | 41 |
| s-8 | 14 | 38 |
| s-9 | 15 | 42 |
| s-10 | 16 | 41 |
| s-11 | 17 | 40 |
| s-12 | 3 | 43 |
| s-13 | 3 | 44 |
| s-14 | 3 | 45 |
| s-15 | 3 | 46 |
| s-16 | 3 | 47 |
| s-17 | 3 | 48 |
| s-18 | 3 | 49 |
| s-19 | 18 | 4 |
| s-20 | 19 | 4 |
| s-21 | 20 | 4 |
| s-22 | 21 | 4 |
| s-23 | 22 | 4 |
| s-24 | 23 | 4 |
| s-25 | 24 | 4 |
| s-26 | 25 | 4 |
| s-27 | 26 | 4 |
| s-28 | 27 | 4 |
| s-29 | 28 | 4 |
| s-30 | 29 | 4 |
| s-31 | 30 | 4 |
| s-32 | 31 | 4 |
| s-33 | 32 | 4 |
| s-34 | 33 | 4 |
| s-35 | 34 | 4 |
| s-36 | 10 | 4 |
| s-37 | 14 | 4 |
| s-38 | 35 | 4 |
| s-39 | 36 | 4 |
| s-40 | 37 | 4 |
| s-41 | 3 | 50 |
| s-42 | 3 | 51 |
| s-43 | 3 | 52 |
| s-44 | 3 | 53 |

8. The TCR of claim 1, wherein a conjugate binds to the α chain and/or β chain of the TCR at C- or N-terminus.

9. A multivalent TCR complex comprising at least two TCR molecules, and at least one TCR molecule is the TCR of claim 1.

10. An isolated cell expressing the TCR of claim 1.

11. A pharmaceutical composition comprising a pharmaceutically acceptable carrier and a TCR of claim 1.

12. The TCR according to claim 4, wherein an artificial interchain disulfide bond is contained between the α chain constant region and the β chain constant region of the TCR.

13. The TCR according to claim 12, wherein cysteine residues forming an artificial interchain disulfide bond between the TCR α chain constant region and β chain constant region are introduced by substituting one or more groups of amino acids selected from the following:
  Thr48 of TRAC*01 exon 1 and Ser57 of TRBC1*01 or TRBC2*01 exon 1;
  Thr45 of TRAC*01 exon 1 and Ser77 of TRBC1*01 or TRBC2*01 exon 1;
  Tyr10 of TRAC*01 exon 1 and Ser17 of TRBC1*01 or TRBC2*01 exon 1;
  Thr45 of TRAC*01 exon 1 and Asp59 of TRBC1*01 or TRBC2*01 exon 1;
  Ser15 of TRAC*01 exon 1 and Glu15 of TRBC1*01 or TRBC2*01 exon 1;
  Arg53 of TRAC*01 exon 1 and Ser54 of TRBC1*01 or TRBC2*01 exon 1;
  Pro89 of TRAC*01 exon 1 and Ala19 of TRBC1*01 or TRBC2*01 exon 1; and
  Tyr10 of TRAC*01 exon 1 and Glu20 of TRBC1*01 or TRBC2*01 exon 1.

14. The TCR according to claim 8, wherein the conjugate that binds to the TCR is a detectable label, a therapeutic agent, a PK modified moiety, or a combination thereof.

15. The TCR according to claim 14, wherein the therapeutic agent that binds to the TCR is an anti-CD3 antibody linked to the α or β chain of the TCR at C- or N-terminus.

* * * * *

```
                         SEQUENCE LISTING

<160> NUMBER OF SEQ ID NOS: 153

<210> SEQ ID NO 1
<211> LENGTH: 109
<212> TYPE: PRT
<213> ORGANISM: Artificial Sequence
<220> FEATURE:
<223> OTHER INFORMATION: Polypeptide

<400> SEQUENCE: 1

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Asn Gly Lys
                85                  90                  95

Ile Ile Phe Gly Lys Gly Thr Arg Leu His Ile Leu Pro
            100                 105

<210> SEQ ID NO 2
<211> LENGTH: 112
<212> TYPE: PRT
<213> ORGANISM: Artificial Sequence
<220> FEATURE:
<223> OTHER INFORMATION: Polypeptide

<400> SEQUENCE: 2

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Ser Leu
                85                  90                  95

Gly Ser Asn Glu Gln Tyr Phe Gly Pro Gly Thr Arg Leu Thr Val Thr
            100                 105                 110

<210> SEQ ID NO 3
<211> LENGTH: 109
<212> TYPE: PRT
<213> ORGANISM: Artificial Sequence
<220> FEATURE:
<223> OTHER INFORMATION: Polypeptide
```

<400> SEQUENCE: 3

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Gly Lys
                85                  90                  95

Ile Ile Phe Gly Lys Gly Thr Arg Leu His Ile Leu Pro
            100                 105

<210> SEQ ID NO 4
<211> LENGTH: 112
<212> TYPE: PRT
<213> ORGANISM: Artificial Sequence
<220> FEATURE:
<223> OTHER INFORMATION: Polypeptide

<400> SEQUENCE: 4

Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Pro Lys Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Ser Leu
                85                  90                  95

Gly Ser Asn Glu Gln Tyr Phe Gly Pro Gly Thr Arg Leu Thr Val Thr
            100                 105                 110

<210> SEQ ID NO 5
<211> LENGTH: 327
<212> TYPE: DNA
<213> ORGANISM: Artificial Sequence
<220> FEATURE:
<223> OTHER INFORMATION: Polynucleotide

<400> SEQUENCE: 5
tctcaacaag gtgaagaaga tccgcaggcc ctgagtattc aagaaggtga aaatgtgacc        60
atcaactgct cttacaaaac gagtatcaac aatctgcagt ggtaccgtca aaattctggc       120
cgcggtctgg ttcatctgat tctgatccgt tccaacgaac gcgaaaaaca ctcaggccgt       180
ctgcgcgtta ccctggatac cagcaaaaaa tcttctagtc tggaaatcac cgcagtccgt       240
ccggcagata cggcaagcta tttttgtgca accgacgcta atggtaaaat tatcttcggc       300
aaaggtaccc gcctgcatat tctgccg                                           327

<210> SEQ ID NO 6

```
<211> LENGTH: 336
<212> TYPE: DNA
<213> ORGANISM: Artificial Sequence
<220> FEATURE:
<223> OTHER INFORMATION: Polynucleotide

<400> SEQUENCE: 6
gatgcgggtg tcacgcagtc tccgcgtcat gaaagtgtgg aaatgggcca agaagttacg      60
ctgcgctgca aaccgatcag cggtcacgac tacctgtttt ggtaccgtca gaccccgaaa     120
cgcggcctgg aactgctgat ctacttcaac aataacgttc cgattgatga ctcgggtatg     180
ccggaagatc gttttagcgc gaaaatgccg aatgcctcgt tcagcacgct gaaaattcag     240
ccggtcgaac gcgtgactc gcagtgtat ttttgtgctt cctcactggg cagtaacgaa       300
cagtacttcg gcccgggtac cgtctgacc gtgacg                                336

<210> SEQ ID NO 7
<211> LENGTH: 24
<212> TYPE: PRT
<213> ORGANISM: Artificial Sequence
<220> FEATURE:
<223> OTHER INFORMATION: Polypeptide

<400> SEQUENCE: 7

Gly Gly Gly Ser Glu Gly Gly Gly Ser Glu Gly Gly Gly Ser Glu Gly
1               5                   10                  15

Gly Gly Ser Glu Gly Gly Thr Gly
            20

<210> SEQ ID NO 8
<211> LENGTH: 72
<212> TYPE: DNA
<213> ORGANISM: Artificial Sequence
<220> FEATURE:
<223> OTHER INFORMATION: Polynucleotide

<400> SEQUENCE: 8
ggcggtggct ccgaaggtgg cggttcagaa ggcggtggct cggaaggtgg cggtagcgaa      60
ggcggtaccg gt                                                          72

<210> SEQ ID NO 9
<211> LENGTH: 109
<212> TYPE: PRT
<213> ORGANISM: Artificial Sequence
<220> FEATURE:
<223> OTHER INFORMATION: Polypeptide

<400> SEQUENCE: 9

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80
```

Pro Ala Asp Thr Ala Ser Tyr Phe Cys Ala Thr Asp Ala Phe Ala Trp
            85                  90                  95

Trp Ile Phe Gly Lys Gly Thr Arg Leu His Ile Leu Pro
            100                 105

<210> SEQ ID NO 10
<211> LENGTH: 109
<212> TYPE: PRT
<213> ORGANISM: Artificial Sequence
<220> FEATURE:
<223> OTHER INFORMATION: Polypeptide

<400> SEQUENCE: 10

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Trp Ala Gln Asn Leu
            20                  25                  30

Gln Trp Tyr Arg Gln Asn Ser Gly Arg Gly Leu Val His Leu Ile Leu
        35                  40                  45

Ile Arg Thr Gly Glu Gln Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Ala Arg
                85                  90                  95

Trp Asn Phe Gly Lys Gly Thr Arg Leu His Ile Leu Pro
            100                 105

<210> SEQ ID NO 11
<211> LENGTH: 109
<212> TYPE: PRT
<213> ORGANISM: Artificial Sequence
<220> FEATURE:
<223> OTHER INFORMATION: Polypeptide

<400> SEQUENCE: 11

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Ser Ile Gln Asn Leu
            20                  25                  30

Gln Trp Tyr Arg Gln Asn Ser Gly Arg Gly Leu Val His Leu Ile Leu
        35                  40                  45

Ile Arg Thr Gly Glu Gln Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Ala Arg
                85                  90                  95

Trp Glu Phe Gly Lys Gly Thr Arg Leu His Ile Leu Pro
            100                 105

<210> SEQ ID NO 12
<211> LENGTH: 109
<212> TYPE: PRT
<213> ORGANISM: Artificial Sequence
<220> FEATURE:
<223> OTHER INFORMATION: Polypeptide

```
<400> SEQUENCE: 12

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Ser Ile Gln Asn Leu
            20                  25                  30

Gln Trp Tyr Arg Gln Asn Ser Gly Arg Gly Leu Val His Leu Ile Leu
        35                  40                  45

Ile Arg Thr Gly Glu Gln Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Ala Arg
                85                  90                  95

Trp Asp Phe Gly Lys Gly Thr Arg Leu His Ile Leu Pro
            100                 105

<210> SEQ ID NO 13
<211> LENGTH: 109
<212> TYPE: PRT
<213> ORGANISM: Artificial Sequence
<220> FEATURE:
<223> OTHER INFORMATION: Polypeptide

<400> SEQUENCE: 13

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Trp Ala Gln Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Ala Arg
                85                  90                  95

Trp Asn Phe Gly Lys Gly Thr Arg Leu His Ile Leu Pro
            100                 105

<210> SEQ ID NO 14
<211> LENGTH: 109
<212> TYPE: PRT
<213> ORGANISM: Artificial Sequence
<220> FEATURE:
<223> OTHER INFORMATION: Polypeptide

<400> SEQUENCE: 14

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Trp Val Gln Asn Leu
            20                  25                  30

Gln Trp Tyr Arg Gln Asn Ser Gly Arg Gly Leu Val His Leu Ile Leu
        35                  40                  45

Ile Arg Thr Gly Glu Gln Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80
```

```
Pro Ala Asp Thr Ala Ser Tyr Phe Cys Ala Thr Asp Ala Asn Ala Arg
                85                  90                  95

Trp Asp Phe Gly Lys Gly Thr Arg Leu His Ile Leu Pro
            100                 105
```

<210> SEQ ID NO 15
<211> LENGTH: 109
<212> TYPE: PRT
<213> ORGANISM: Artificial Sequence
<220> FEATURE:
<223> OTHER INFORMATION: Polypeptide

<400> SEQUENCE: 15

```
Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Ser Ile Gln Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Ala Arg
                85                  90                  95

Trp Asp Phe Gly Lys Gly Thr Arg Leu His Ile Leu Pro
            100                 105
```

<210> SEQ ID NO 16
<211> LENGTH: 105
<212> TYPE: PRT
<213> ORGANISM: Artificial Sequence
<220> FEATURE:
<223> OTHER INFORMATION: Polypeptide

<400> SEQUENCE: 16

```
Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Trp Ala Gln Asn Arg
            20                  25                  30

Gln Asn Ser Gly Arg Gly Leu Val His Leu Ile Leu Ile Arg Ser Asn
        35                  40                  45

Glu Arg Glu Lys His Ser Gly Arg Leu Arg Val Thr Leu Asp Thr Ser
    50                  55                  60

Lys Lys Ser Ser Ser Leu Glu Ile Thr Ala Val Arg Pro Ala Asp Thr
65                  70                  75                  80

Ala Ser Tyr Phe Cys Ala Thr Asp Ala Asn Ala Arg Trp Asp Phe Gly
                85                  90                  95

Lys Gly Thr Arg Leu His Ile Leu Pro
            100                 105
```

<210> SEQ ID NO 17
<211> LENGTH: 109
<212> TYPE: PRT
<213> ORGANISM: Artificial Sequence
<220> FEATURE:
<223> OTHER INFORMATION: Polypeptide

<400> SEQUENCE: 17

```
Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Ser Ile Gln Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Ala Arg
                85                  90                  95

Trp Glu Phe Gly Lys Gly Thr Arg Leu His Ile Leu Pro
            100                 105
```

<210> SEQ ID NO 18
<211> LENGTH: 109
<212> TYPE: PRT
<213> ORGANISM: Artificial Sequence
<220> FEATURE:
<223> OTHER INFORMATION: Polypeptide

<400> SEQUENCE: 18

```
Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Met Tyr Asp Glu Asn Gly Lys
                85                  90                  95

Ile Ile Phe Gly Lys Gly Thr Arg Leu His Ile Leu Pro
            100                 105
```

<210> SEQ ID NO 19
<211> LENGTH: 109
<212> TYPE: PRT
<213> ORGANISM: Artificial Sequence
<220> FEATURE:
<223> OTHER INFORMATION: Polypeptide

<400> SEQUENCE: 19

```
Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80
```

-continued

Pro Ala Asp Thr Ala Ser Tyr Phe Cys Met Tyr Asp Gln Asn Gly Lys
              85                  90                  95

Ile Ile Phe Gly Lys Gly Thr Arg Leu His Ile Leu Pro
        100                 105

<210> SEQ ID NO 20
<211> LENGTH: 109
<212> TYPE: PRT
<213> ORGANISM: Artificial Sequence
<220> FEATURE:
<223> OTHER INFORMATION: Polypeptide

<400> SEQUENCE: 20

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Tyr Gly Thr
                85                  90                  95

Val Gln Phe Gly Lys Gly Thr Arg Leu His Ile Leu Pro
        100                 105

<210> SEQ ID NO 21
<211> LENGTH: 109
<212> TYPE: PRT
<213> ORGANISM: Artificial Sequence
<220> FEATURE:
<223> OTHER INFORMATION: Polypeptide

<400> SEQUENCE: 21

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Gly Thr
                85                  90                  95

Val Gln Phe Gly Lys Gly Thr Arg Leu His Ile Leu Pro
        100                 105

<210> SEQ ID NO 22
<211> LENGTH: 109
<212> TYPE: PRT
<213> ORGANISM: Artificial Sequence
<220> FEATURE:
<223> OTHER INFORMATION: Polypeptide -continued

```
<400> SEQUENCE: 22

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Gly Ser
                85                  90                  95

Val Gln Phe Gly Lys Gly Thr Arg Leu His Ile Leu Pro
            100                 105

<210> SEQ ID NO 23
<211> LENGTH: 109
<212> TYPE: PRT
<213> ORGANISM: Artificial Sequence
<220> FEATURE:
<223> OTHER INFORMATION: Polypeptide

<400> SEQUENCE: 23

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Tyr Gly Arg
                85                  90                  95

Tyr Ile Phe Gly Lys Gly Thr Arg Leu His Ile Leu Pro
            100                 105

<210> SEQ ID NO 24
<211> LENGTH: 109
<212> TYPE: PRT
<213> ORGANISM: Artificial Sequence
<220> FEATURE:
<223> OTHER INFORMATION: Polypeptide

<400> SEQUENCE: 24

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80
```

```
Pro Ala Asp Thr Ala Ser Tyr Phe Cys Ala Thr Asp Ala Asn Gln Met
                85                  90                  95

Trp Lys Phe Gly Lys Gly Thr Arg Leu His Ile Leu Pro
            100                 105

<210> SEQ ID NO 25
<211> LENGTH: 109
<212> TYPE: PRT
<213> ORGANISM: Artificial Sequence
<220> FEATURE:
<223> OTHER INFORMATION: Polypeptide

<400> SEQUENCE: 25

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
                20                  25                  30

Gln Trp Tyr Arg Gln Asn Ser Gly Arg Gly Leu Val His Leu Ile Leu
            35                  40                  45

Ile Arg Ser Asn Glu Arg Glu Lys His Ser Gly Arg Leu Arg Val Thr
50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Tyr Gly Leu
                85                  90                  95

Pro Ile Phe Gly Lys Gly Thr Arg Leu His Ile Leu Pro
            100                 105

<210> SEQ ID NO 26
<211> LENGTH: 109
<212> TYPE: PRT
<213> ORGANISM: Artificial Sequence
<220> FEATURE:
<223> OTHER INFORMATION: Polypeptide

<400> SEQUENCE: 26

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
                20                  25                  30

Gln Trp Tyr Arg Gln Asn Ser Gly Arg Gly Leu Val His Leu Ile Leu
            35                  40                  45

Ile Arg Ser Asn Glu Arg Glu Lys His Ser Gly Arg Leu Arg Val Thr
50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Gly Leu
                85                  90                  95

Pro Val Phe Gly Lys Gly Thr Arg Leu His Ile Leu Pro
            100                 105

<210> SEQ ID NO 27
<211> LENGTH: 109
<212> TYPE: PRT
<213> ORGANISM: Artificial Sequence
<220> FEATURE:
<223> OTHER INFORMATION: Polypeptide
```

-continued

```
<400> SEQUENCE: 27

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Gly Arg
                85                  90                  95

Trp Glu Phe Gly Lys Gly Thr Arg Leu His Ile Leu Pro
            100                 105

<210> SEQ ID NO 28
<211> LENGTH: 109
<212> TYPE: PRT
<213> ORGANISM: Artificial Sequence
<220> FEATURE:
<223> OTHER INFORMATION: Polypeptide

<400> SEQUENCE: 28

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Gly Thr
                85                  90                  95

Val Gly Phe Gly Lys Gly Thr Arg Leu His Ile Leu Pro
            100                 105

<210> SEQ ID NO 29
<211> LENGTH: 109
<212> TYPE: PRT
<213> ORGANISM: Artificial Sequence
<220> FEATURE:
<223> OTHER INFORMATION: Polypeptide

<400> SEQUENCE: 29

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80
```

```
Pro Ala Asp Thr Ala Ser Tyr Phe Cys Ala Thr Asp Ala Asn Gly Arg
                85                  90                  95

Trp Met Phe Gly Lys Gly Thr Arg Leu His Ile Leu Pro
            100                 105
```

<210> SEQ ID NO 30
<211> LENGTH: 109
<212> TYPE: PRT
<213> ORGANISM: Artificial Sequence
<220> FEATURE:
<223> OTHER INFORMATION: Polypeptide

<400> SEQUENCE: 30

```
Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Gly Leu
                85                  90                  95

Trp Ser Phe Gly Lys Gly Thr Arg Leu His Ile Leu Pro
            100                 105
```

<210> SEQ ID NO 31
<211> LENGTH: 109
<212> TYPE: PRT
<213> ORGANISM: Artificial Sequence
<220> FEATURE:
<223> OTHER INFORMATION: Polypeptide

<400> SEQUENCE: 31

```
Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Trp Ala Gln Asn Leu
            20                  25                  30

Gln Trp Tyr Arg Gln Asn Ser Gly Arg Gly Leu Val His Leu Ile Leu
        35                  40                  45

Ile Arg Thr Gly Glu Gln Glu Lys His Ser Gly Arg Leu Arg Val Thr
50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Ala Arg
                85                  90                  95

Trp Asp Phe Gly Lys Gly Thr Arg Leu His Ile Leu Pro
            100                 105
```

<210> SEQ ID NO 32
<211> LENGTH: 109
<212> TYPE: PRT
<213> ORGANISM: Artificial Sequence
<220> FEATURE:
<223> OTHER INFORMATION: Polypeptide

<400> SEQUENCE: 32

```
Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Trp Ala Gln Asn Leu
            20                  25                  30

Gln Trp Tyr Arg Gln Asn Ser Gly Arg Gly Leu Val His Leu Ile Leu
        35                  40                  45

Ile Arg Thr Gly Gln Ala Glu Lys His Ser Gly Arg Leu Arg Val Thr
    50                  55                  60

Leu Asp Thr Ser Lys Lys Ser Ser Leu Glu Ile Thr Ala Val Arg
65                  70                  75                  80

Pro Ala Asp Thr Ala Ser Tyr Phe Cys Ala Thr Asp Ala Asn Ala Arg
                85                  90                  95

Trp Glu Phe Gly Lys Gly Thr Arg Leu His Ile Leu Pro
            100                 105
```

<210> SEQ ID NO 33
<211> LENGTH: 109
<212> TYPE: PRT
<213> ORGANISM: Artificial Sequence
<220> FEATURE:
<223> OTHER INFORMATION: Polypeptide

<400> SEQUENCE: 33

```
Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Ser Ile Gln Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Leu Glu Ile Thr Ala Val Arg
65                  70                  75                  80

Pro Ala Asp Thr Ala Ser Tyr Phe Cys Ala Thr Asp Ala Phe Ala Trp
                85                  90                  95

Trp Ile Phe Gly Lys Gly Thr Arg Leu His Ile Leu Pro
            100                 105
```

<210> SEQ ID NO 34
<211> LENGTH: 109
<212> TYPE: PRT
<213> ORGANISM: Artificial Sequence
<220> FEATURE:
<223> OTHER INFORMATION: Polypeptide

<400> SEQUENCE: 34

```
Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Trp Val Gln Asn Leu
            20                  25                  30

Gln Trp Tyr Arg Gln Asn Ser Gly Arg Gly Leu Val His Leu Ile Leu
        35                  40                  45

Ile Arg Thr Gly Glu Gln Glu Lys His Ser Gly Arg Leu Arg Val Thr
    50                  55                  60

Leu Asp Thr Ser Lys Lys Ser Ser Leu Glu Ile Thr Ala Val Arg
65                  70                  75                  80
```

```
Pro Ala Asp Thr Ala Ser Tyr Phe Cys Ala Thr Asp Ala Asn Ala Arg
                85                  90                  95

Trp Asn Phe Gly Lys Gly Thr Arg Leu His Ile Leu Pro
            100                 105

<210> SEQ ID NO 35
<211> LENGTH: 109
<212> TYPE: PRT
<213> ORGANISM: Artificial Sequence
<220> FEATURE:
<223> OTHER INFORMATION: Polypeptide

<400> SEQUENCE: 35

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Ser Ile Gln Asn Leu
            20                  25                  30

Gln Trp Tyr Arg Gln Asn Ser Gly Arg Gly Leu Val His Leu Ile Leu
        35                  40                  45

Ile Arg Thr Gly Glu Gln Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Trp Ala Arg
                85                  90                  95

Trp Ile Phe Gly Lys Gly Thr Arg Leu His Ile Leu Pro
            100                 105

<210> SEQ ID NO 36
<211> LENGTH: 109
<212> TYPE: PRT
<213> ORGANISM: Artificial Sequence
<220> FEATURE:
<223> OTHER INFORMATION: Polypeptide

<400> SEQUENCE: 36

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Trp Val Gln Asn Leu
            20                  25                  30

Gln Trp Tyr Arg Gln Asn Ser Gly Arg Gly Leu Val His Leu Ile Leu
        35                  40                  45

Ile Arg Thr Gly Gln Ala Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Ala Arg
                85                  90                  95

Trp Glu Phe Gly Lys Gly Thr Arg Leu His Ile Leu Pro
            100                 105

<210> SEQ ID NO 37
<211> LENGTH: 109
<212> TYPE: PRT
<213> ORGANISM: Artificial Sequence
<220> FEATURE:
<223> OTHER INFORMATION: Polypeptide
```

<400> SEQUENCE: 37

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Gly Ser Ile Gln Asn Leu
            20                  25                  30

Gln Trp Tyr Arg Gln Asn Ser Gly Arg Gly Leu Val His Leu Ile Leu
        35                  40                  45

Ile Arg Thr Gly Glu Gln Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80

Pro Ala Asp Thr Ala Ser Tyr Phe Cys Ala Thr Asp Ala Asn Ala Arg
                85                  90                  95

Trp Asn Phe Gly Lys Gly Thr Arg Leu His Ile Leu Pro
                100                 105

<210> SEQ ID NO 38
<211> LENGTH: 112
<212> TYPE: PRT
<213> ORGANISM: Artificial Sequence
<220> FEATURE:
<223> OTHER INFORMATION: Polypeptide

<400> SEQUENCE: 38

Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Pro Lys Arg Gly Leu Glu Leu Leu Ile Tyr
        35                  40                  45

Phe Asn His Gly Ala Val Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Ser Leu
                85                  90                  95

Gly Ser Asn Glu Gln Tyr Phe Gly Pro Gly Thr Arg Leu Thr Val Thr
                100                 105                 110

<210> SEQ ID NO 39
<211> LENGTH: 112
<212> TYPE: PRT
<213> ORGANISM: Artificial Sequence
<220> FEATURE:
<223> OTHER INFORMATION: Polypeptide

<400> SEQUENCE: 39

Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Pro Lys Arg Gly Leu Glu Leu Leu Ile Tyr
        35                  40                  45

Phe Asn His Gly Ala Val Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Gln Arg
                85                  90                  95

Gly Ser Asn Glu Gln Tyr Phe Gly Pro Gly Thr Arg Leu Thr Val Thr
            100                 105                 110

<210> SEQ ID NO 40
<211> LENGTH: 112
<212> TYPE: PRT
<213> ORGANISM: Artificial Sequence
<220> FEATURE:
<223> OTHER INFORMATION: Polypeptide

<400> SEQUENCE: 40

Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Pro Lys Arg Gly Leu Glu Leu Leu Ile Tyr
        35                  40                  45

Phe Asn His Gly Ala Val Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Gln Lys
                85                  90                  95

Gly Ala Asn Glu Gln Tyr Phe Gly Pro Gly Thr Arg Leu Thr Val Thr
            100                 105                 110

<210> SEQ ID NO 41
<211> LENGTH: 112
<212> TYPE: PRT
<213> ORGANISM: Artificial Sequence
<220> FEATURE:
<223> OTHER INFORMATION: Polypeptide

<400> SEQUENCE: 41

Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Pro Lys Arg Gly Leu Glu Leu Leu Ile Tyr
        35                  40                  45

Phe Asn His Gly Ala Val Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Gln Leu
                85                  90                  95

Gly Ser Asn Glu Gln Tyr Phe Gly Pro Gly Thr Arg Leu Thr Val Thr
            100                 105                 110

<210> SEQ ID NO 42
<211> LENGTH: 112
<212> TYPE: PRT
<213> ORGANISM: Artificial Sequence
<220> FEATURE:
<223> OTHER INFORMATION: Polypeptide

<400> SEQUENCE: 42

Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Pro Lys Arg Gly Leu Glu Leu Leu Ile Tyr
        35                  40                  45

Phe Asn His Gly Ala Val Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Gln Leu
                85                  90                  95

Gly Ala Asn Glu Gln Tyr Phe Gly Pro Gly Thr Arg Leu Thr Val Thr
            100                 105                 110

<210> SEQ ID NO 43
<211> LENGTH: 112
<212> TYPE: PRT
<213> ORGANISM: Artificial Sequence
<220> FEATURE:
<223> OTHER INFORMATION: Polypeptide

<400> SEQUENCE: 43

Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Pro Lys Arg Gly Leu Glu Leu Leu Ile Tyr
        35                  40                  45

Phe Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Gln Leu
                85                  90                  95

Gly Gly Asn Glu Gln Tyr Phe Gly Pro Gly Thr Arg Leu Thr Val Thr
            100                 105                 110

<210> SEQ ID NO 44
<211> LENGTH: 112
<212> TYPE: PRT
<213> ORGANISM: Artificial Sequence
<220> FEATURE:
<223> OTHER INFORMATION: Polypeptide

<400> SEQUENCE: 44

Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Pro Lys Arg Gly Leu Glu Leu Leu Ile Tyr
        35                  40                  45

Phe Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

```
Pro Val Glu Pro Arg Asp Ser Ala Val Tyr Phe Cys Ala Ser Gln Lys
                85                  90                  95

Gly Ala Asn Glu Gln Tyr Phe Gly Pro Gly Thr Arg Leu Thr Val Thr
            100                 105                 110
```

<210> SEQ ID NO 45
<211> LENGTH: 112
<212> TYPE: PRT
<213> ORGANISM: Artificial Sequence
<220> FEATURE:
<223> OTHER INFORMATION: Polypeptide

<400> SEQUENCE: 45

```
Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
                20                  25                  30

Phe Trp Tyr Arg Gln Thr Pro Lys Arg Gly Leu Glu Leu Leu Ile Tyr
            35                  40                  45

Phe Asn Asn Asn Val Pro Ile Asp Asp Ser Gly Met Pro Glu Asp Arg
        50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Gln Leu
                85                  90                  95

Gly Pro Asn Glu Gln Tyr Phe Gly Pro Gly Thr Arg Leu Thr Val Thr
            100                 105                 110
```

<210> SEQ ID NO 46
<211> LENGTH: 112
<212> TYPE: PRT
<213> ORGANISM: Artificial Sequence
<220> FEATURE:
<223> OTHER INFORMATION: Polypeptide

<400> SEQUENCE: 46

```
Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
                20                  25                  30

Phe Trp Tyr Arg Gln Thr Pro Lys Arg Gly Leu Glu Leu Leu Ile Tyr
            35                  40                  45

Phe Asn Asn Asn Val Pro Ile Asp Asp Ser Gly Met Pro Glu Asp Arg
        50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Gln Arg
                85                  90                  95

Gly Ala Asn Glu Gln Tyr Phe Gly Pro Gly Thr Arg Leu Thr Val Thr
            100                 105                 110
```

<210> SEQ ID NO 47
<211> LENGTH: 112
<212> TYPE: PRT
<213> ORGANISM: Artificial Sequence
<220> FEATURE:
<223> OTHER INFORMATION: Polypeptide

<400> SEQUENCE: 47

Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Pro Lys Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Gln Met
                85                  90                  95

Gly Ser Asn Glu Gln Tyr Phe Gly Pro Gly Thr Arg Leu Thr Val Thr
            100                 105                 110

<210> SEQ ID NO 48
<211> LENGTH: 112
<212> TYPE: PRT
<213> ORGANISM: Artificial Sequence
<220> FEATURE:
<223> OTHER INFORMATION: Polypeptide

<400> SEQUENCE: 48

Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Pro Lys Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Gln Leu
                85                  90                  95

Gly Ser Asn Glu Gln Tyr Phe Gly Pro Gly Thr Arg Leu Thr Val Thr
            100                 105                 110

<210> SEQ ID NO 49
<211> LENGTH: 112
<212> TYPE: PRT
<213> ORGANISM: Artificial Sequence
<220> FEATURE:
<223> OTHER INFORMATION: Polypeptide

<400> SEQUENCE: 49

Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Pro Lys Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

-continued

```
Pro Val Glu Pro Arg Asp Ser Ala Val Tyr Phe Cys Ala Ser Gln Leu
                85                  90                  95

Gly Ala Asn Glu Gln Tyr Phe Gly Pro Gly Thr Arg Leu Thr Val Thr
            100                 105                 110
```

<210> SEQ ID NO 50
<211> LENGTH: 112
<212> TYPE: PRT
<213> ORGANISM: Artificial Sequence
<220> FEATURE:
<223> OTHER INFORMATION: Polypeptide

<400> SEQUENCE: 50

```
Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
                20                  25                  30

Phe Trp Tyr Arg Gln Thr Pro Lys Arg Gly Leu Glu Leu Leu Ile Tyr
            35                  40                  45

Phe Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Gln Met
                85                  90                  95

Gly Ser Asn Glu Gln Tyr Phe Gly Pro Gly Thr Arg Leu Thr Val Thr
            100                 105                 110
```

<210> SEQ ID NO 51
<211> LENGTH: 112
<212> TYPE: PRT
<213> ORGANISM: Artificial Sequence
<220> FEATURE:
<223> OTHER INFORMATION: Polypeptide

<400> SEQUENCE: 51

```
Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
                20                  25                  30

Phe Trp Tyr Arg Gln Thr Pro Lys Arg Gly Leu Glu Leu Leu Ile Tyr
            35                  40                  45

Phe Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Gln Arg
                85                  90                  95

Gly Ser Asn Glu Gln Tyr Phe Gly Pro Gly Thr Arg Leu Thr Val Thr
            100                 105                 110
```

<210> SEQ ID NO 52
<211> LENGTH: 112
<212> TYPE: PRT
<213> ORGANISM: Artificial Sequence
<220> FEATURE:
<223> OTHER INFORMATION: Polypeptide

```
<400> SEQUENCE: 52

Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Pro Lys Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Gln Met
                85                  90                  95

Gly Ala Asn Glu Gln Tyr Phe Gly Pro Gly Thr Arg Leu Thr Val Thr
            100                 105                 110

<210> SEQ ID NO 53
<211> LENGTH: 112
<212> TYPE: PRT
<213> ORGANISM: Artificial Sequence
<220> FEATURE:
<223> OTHER INFORMATION: Polypeptide

<400> SEQUENCE: 53

Asp Ala Gly Val Thr Gln Ser Pro Arg His Glu Ser Val Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Pro Lys Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Val Glu Pro Arg Asp Ser Ala Val Tyr Phe Cys Ala Ser Met Leu
                85                  90                  95

Gly Ser Asn Glu Gln Tyr Phe Gly Pro Gly Thr Arg Leu Thr Val Thr
            100                 105                 110

<210> SEQ ID NO 54
<211> LENGTH: 245
<212> TYPE: PRT
<213> ORGANISM: Artificial Sequence
<220> FEATURE:
<223> OTHER INFORMATION: Polypeptide

<400> SEQUENCE: 54

Ser Gln Gln Gly Glu Glu Asp Pro Gln Ala Leu Ser Ile Gln Glu Gly
1               5                   10                  15

Glu Asn Val Thr Ile Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Glu Ile Thr Ala Val Arg
65                  70                  75                  80
```

```
Pro Ala Asp Thr Ala Ser Tyr Phe Cys Ala Thr Asp Ala Asn Gly Lys
                85                  90                  95

Ile Ile Phe Gly Lys Gly Thr Arg Leu His Ile Leu Pro Gly Gly Gly
            100                 105                 110

Ser Glu Gly Gly Ser Glu Gly Gly Ser Glu Gly Gly Ser
        115                 120                 125

Glu Gly Gly Thr Gly Asp Ala Gly Val Thr Gln Ser Pro Arg His Glu
        130                 135                 140

Ser Val Glu Met Gly Gln Glu Val Thr Leu Arg Cys Lys Pro Ile Ser
145                 150                 155                 160

Gly His Asp Tyr Leu Phe Trp Tyr Arg Gln Thr Pro Lys Arg Gly Leu
                165                 170                 175

Glu Leu Leu Ile Tyr Phe Asn Asn Val Pro Ile Asp Asp Ser Gly
                180                 185                 190

Met Pro Glu Asp Arg Phe Ser Ala Lys Met Pro Asn Ala Ser Phe Ser
            195                 200                 205

Thr Leu Lys Ile Gln Pro Val Glu Pro Arg Asp Ser Ala Val Tyr Phe
        210                 215                 220

Cys Ala Ser Ser Leu Gly Ser Asn Glu Gln Tyr Phe Gly Pro Gly Thr
225                 230                 235                 240

Arg Leu Thr Val Thr
                245

<210> SEQ ID NO 55
<211> LENGTH: 735
<212> TYPE: DNA
<213> ORGANISM: Artificial Sequence
<220> FEATURE:
<223> OTHER INFORMATION: Polynucleotide

<400> SEQUENCE: 55
tctcaacaag gtgaagaaga tccgcaggcc ctgagtattc aagaaggtga aaatgtgacc      60
atcaactgct cttacaaaac gagtatcaac aatctgcagt ggtaccgtca aaattctggc     120
cgcggtctgg ttcatctgat tctgatccgt tccaacgaac gcgaaaaaca ctcaggccgt     180
ctgcgcgtta ccctggatac cagcaaaaaa tcttctagtc tggaaatcac cgcagtccgt     240
ccggcagata cggcaagcta tttttgtgca accgacgcta atggtaaaat tatcttcggc     300
aaaggtaccc gcctgcatat tctgccgggc ggtggctccg aaggtggcgg ttcagaaggc     360
ggtggctcgg aaggtggcgg tagcgaaggc ggtaccggtg atgcgggtgt cacgcagtct     420
ccgcgtcatg aaagtgtgga aatgggccaa gaagttacgc tgcgctgcaa accgatcagc     480
ggtcacgact acctgttttg gtaccgtcag accccgaaac gcggcctgga actgctgatc     540
tacttcaaca ataacgttcc gattgatgac tcgggtatgc cggaagatcg ttttagcgcg     600
aaaatgccga atgcctcgtt cagcacgctg aaaattcagc cggtcgaacc gcgtgactcc     660
gcagtgtatt tttgtgcttc ctcactgggc agtaacgaac agtacttcgg cccgggtacc     720
cgtctgaccg tgacg                                                      735

<210> SEQ ID NO 56
<211> LENGTH: 203
<212> TYPE: PRT
<213> ORGANISM: Artificial Sequence
<220> FEATURE:
<223> OTHER INFORMATION: Polypeptide
```

<400> SEQUENCE: 56

```
Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Leu Leu Ile Thr Ala Ser Arg
65                  70                  75                  80

Ala Ala Asp Thr Ala Ser Tyr Phe Cys Ala Thr Asp Ala Asn Gly Lys
                85                  90                  95

Ile Ile Phe Gly Lys Gly Thr Arg Leu His Ile Leu Pro Asn Ile Gln
            100                 105                 110

Asn Pro Asp Pro Ala Val Tyr Gln Leu Arg Asp Ser Lys Ser Ser Asp
        115                 120                 125

Lys Ser Val Cys Leu Phe Thr Asp Phe Asp Ser Gln Thr Asn Val Ser
130                 135                 140

Gln Ser Lys Asp Ser Asp Val Tyr Ile Thr Asp Lys Cys Val Leu Asp
145                 150                 155                 160

Met Arg Ser Met Asp Phe Lys Ser Asn Ser Ala Val Ala Trp Ser Asn
                165                 170                 175

Lys Ser Asp Phe Ala Cys Ala Asn Ala Phe Asn Asn Ser Ile Ile Pro
            180                 185                 190

Glu Asp Thr Phe Phe Pro Ser Pro Glu Ser Ser
            195                 200
```

<210> SEQ ID NO 57
<211> LENGTH: 242
<212> TYPE: PRT
<213> ORGANISM: Artificial Sequence
<220> FEATURE:
<223> OTHER INFORMATION: Polypeptide

<400> SEQUENCE: 57

```
Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Ser Leu
                85                  90                  95

Gly Ser Asn Glu Gln Tyr Phe Gly Pro Gly Thr Arg Leu Thr Val Thr
            100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140
```

Ala Thr Gly Phe Tyr Pro Asp His Val Glu Leu Ser Trp Trp Val Asn
145                 150                 155                 160

Gly Lys Glu Val His Ser Gly Val Cys Thr Asp Pro Gln Pro Leu Lys
                165                 170                 175

Glu Gln Pro Ala Leu Asn Asp Ser Arg Tyr Ala Leu Ser Ser Arg Leu
            180                 185                 190

Arg Val Ser Ala Thr Phe Trp Gln Asp Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp

<210> SEQ ID NO 58
<211> LENGTH: 109
<212> TYPE: PRT
<213> ORGANISM: Artificial Sequence
<220> FEATURE:
<223> OTHER INFORMATION: Polypeptide

<400> SEQUENCE: 58

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Phe Ala Trp
                85                  90                  95

Trp Ile Phe Gly Lys Gly Thr Arg Leu His Ile Leu Pro
            100                 105

<210> SEQ ID NO 59
<211> LENGTH: 109
<212> TYPE: PRT
<213> ORGANISM: Artificial Sequence
<220> FEATURE:
<223> OTHER INFORMATION: Polypeptide

<400> SEQUENCE: 59

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Gly Trp Ala Gln Asn Leu
            20                  25                  30

Gln Trp Tyr Arg Gln Asn Ser Gly Arg Gly Leu Val His Leu Ile Leu
        35                  40                  45

Ile Arg Thr Gly Glu Gln Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Asn Ala Arg
                85                  90                  95

Trp Asn Phe Gly Lys Gly Thr Arg Leu His Ile Leu Pro
            100                 105

<210> SEQ ID NO 60
<211> LENGTH: 109
<212> TYPE: PRT
<213> ORGANISM: Artificial Sequence
<220> FEATURE:
<223> OTHER INFORMATION: Polypeptide

<400> SEQUENCE: 60

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Gly Ser Ile Gln Asn Leu
                20                  25                  30

Gln Trp Tyr Arg Gln Asn Ser Gly Arg Gly Leu Val His Leu Ile Leu
            35                  40                  45

Ile Arg Thr Gly Glu Gln Glu Lys His Ser Gly Arg Leu Arg Val Thr
        50                  55                  60

Leu Asp Thr Ser Lys Lys Ser Ser Leu Leu Ile Thr Ala Ser Arg
65                  70                  75                  80

Ala Ala Asp Thr Ala Ser Tyr Phe Cys Ala Thr Asp Ala Asn Ala Arg
                85                  90                  95

Trp Glu Phe Gly Lys Gly Thr Arg Leu His Ile Leu Pro
            100                 105

<210> SEQ ID NO 61
<211> LENGTH: 109
<212> TYPE: PRT
<213> ORGANISM: Artificial Sequence
<220> FEATURE:
<223> OTHER INFORMATION: Polypeptide

<400> SEQUENCE: 61

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Gly Ser Ile Gln Asn Leu
                20                  25                  30

Gln Trp Tyr Arg Gln Asn Ser Gly Arg Gly Leu Val His Leu Ile Leu
            35                  40                  45

Ile Arg Thr Gly Glu Gln Glu Lys His Ser Gly Arg Leu Arg Val Thr
        50                  55                  60

Leu Asp Thr Ser Lys Lys Ser Ser Leu Leu Ile Thr Ala Ser Arg
65                  70                  75                  80

Ala Ala Asp Thr Ala Ser Tyr Phe Cys Ala Thr Asp Ala Asn Ala Arg
                85                  90                  95

Trp Asp Phe Gly Lys Gly Thr Arg Leu His Ile Leu Pro
            100                 105

<210> SEQ ID NO 62
<211> LENGTH: 109
<212> TYPE: PRT
<213> ORGANISM: Artificial Sequence
<220> FEATURE:
<223> OTHER INFORMATION: Polypeptide

<400> SEQUENCE: 62

Ser Gln Gln Gly Glu Glu Asp Pro Gln Ala Leu Ser Ile Gln Glu Gly
1               5                   10                  15

```
Glu Asn Ala Thr Met Asn Cys Ser Tyr Lys Gly Trp Ala Gln Asn Leu
                20                  25                  30

Gln Trp Tyr Arg Gln Asn Ser Gly Arg Gly Leu Val His Leu Ile Leu
            35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Asn Ala Arg
                85                  90                  95

Trp Asn Phe Gly Lys Gly Thr Arg Leu His Ile Leu Pro
                100                 105

<210> SEQ ID NO 63
<211> LENGTH: 109
<212> TYPE: PRT
<213> ORGANISM: Artificial Sequence
<220> FEATURE:
<223> OTHER INFORMATION: Polypeptide

<400> SEQUENCE: 63

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Gly Trp Val Gln Asn Leu
                20                  25                  30

Gln Trp Tyr Arg Gln Asn Ser Gly Arg Gly Leu Val His Leu Ile Leu
            35                  40                  45

Ile Arg Thr Gly Glu Gln Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Asn Ala Arg
                85                  90                  95

Trp Asp Phe Gly Lys Gly Thr Arg Leu His Ile Leu Pro
                100                 105

<210> SEQ ID NO 64
<211> LENGTH: 109
<212> TYPE: PRT
<213> ORGANISM: Artificial Sequence
<220> FEATURE:
<223> OTHER INFORMATION: Polypeptide

<400> SEQUENCE: 64

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Gly Ser Ile Gln Asn Leu
                20                  25                  30

Gln Trp Tyr Arg Gln Asn Ser Gly Arg Gly Leu Val His Leu Ile Leu
            35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Asn Ala Arg
                85                  90                  95
```

```
Trp Asp Phe Gly Lys Gly Thr Arg Leu His Ile Leu Pro
            100                 105
```

<210> SEQ ID NO 65
<211> LENGTH: 105
<212> TYPE: PRT
<213> ORGANISM: Artificial Sequence
<220> FEATURE:
<223> OTHER INFORMATION: Polypeptide

<400> SEQUENCE: 65

```
Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Gly Trp Ala Gln Asn Arg
            20                  25                  30

Gln Asn Ser Gly Arg Gly Leu Val His Leu Ile Leu Ile Arg Ser Asn
        35                  40                  45

Glu Arg Glu Lys His Ser Gly Arg Leu Arg Val Thr Leu Asp Thr Ser
    50                  55                  60

Lys Lys Ser Ser Ser Leu Leu Ile Thr Ala Ser Arg Ala Ala Asp Thr
65                  70                  75                  80

Ala Ser Tyr Phe Cys Ala Thr Asp Ala Asn Ala Arg Trp Asp Phe Gly
                85                  90                  95

Lys Gly Thr Arg Leu His Ile Leu Pro
            100                 105
```

<210> SEQ ID NO 66
<211> LENGTH: 109
<212> TYPE: PRT
<213> ORGANISM: Artificial Sequence
<220> FEATURE:
<223> OTHER INFORMATION: Polypeptide

<400> SEQUENCE: 66

```
Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Gly Ser Ile Gln Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Asn Ala Arg
                85                  90                  95

Trp Glu Phe Gly Lys Gly Thr Arg Leu His Ile Leu Pro
            100                 105
```

<210> SEQ ID NO 67
<211> LENGTH: 109
<212> TYPE: PRT
<213> ORGANISM: Artificial Sequence
<220> FEATURE:
<223> OTHER INFORMATION: Polypeptide

<400> SEQUENCE: 67

```
Ser Gln Gln Gly Glu Glu Asp Pro Gln Ala Leu Ser Ile Gln Glu Gly
1               5                   10                  15
```

```
Glu Asn Ala Thr Met Asn Cys Ser Tyr Lys Thr Ser Ile Asn Asn Leu
                20                  25                  30

Gln Trp Tyr Arg Gln Asn Ser Gly Arg Gly Leu Val His Leu Ile Leu
            35                  40                  45

Ile Arg Ser Asn Glu Arg Glu Lys His Ser Gly Arg Leu Arg Val Thr
        50                  55                  60

Leu Asp Thr Ser Lys Lys Ser Ser Ser Leu Leu Ile Thr Ala Ser Arg
 65                  70                  75                  80

Ala Ala Asp Thr Ala Ser Tyr Phe Cys Met Tyr Asp Glu Asn Gly Lys
                85                  90                  95

Ile Ile Phe Gly Lys Gly Thr Arg Leu His Ile Leu Pro
                100                 105
```

<210> SEQ ID NO 68
<211> LENGTH: 109
<212> TYPE: PRT
<213> ORGANISM: Artificial Sequence
<220> FEATURE:
<223> OTHER INFORMATION: Polypeptide

<400> SEQUENCE: 68

```
Ser Gln Gln Gly Glu Glu Asp Pro Gln Ala Leu Ser Ile Gln Glu Gly
 1               5                  10                  15

Glu Asn Ala Thr Met Asn Cys Ser Tyr Lys Thr Ser Ile Asn Asn Leu
                20                  25                  30

Gln Trp Tyr Arg Gln Asn Ser Gly Arg Gly Leu Val His Leu Ile Leu
            35                  40                  45

Ile Arg Ser Asn Glu Arg Glu Lys His Ser Gly Arg Leu Arg Val Thr
        50                  55                  60

Leu Asp Thr Ser Lys Lys Ser Ser Ser Leu Leu Ile Thr Ala Ser Arg
 65                  70                  75                  80

Ala Ala Asp Thr Ala Ser Tyr Phe Cys Met Tyr Asp Gln Asn Gly Lys
                85                  90                  95

Ile Ile Phe Gly Lys Gly Thr Arg Leu His Ile Leu Pro
                100                 105
```

<210> SEQ ID NO 69
<211> LENGTH: 109
<212> TYPE: PRT
<213> ORGANISM: Artificial Sequence
<220> FEATURE:
<223> OTHER INFORMATION: Polypeptide

<400> SEQUENCE: 69

```
Ser Gln Gln Gly Glu Glu Asp Pro Gln Ala Leu Ser Ile Gln Glu Gly
 1               5                  10                  15

Glu Asn Ala Thr Met Asn Cys Ser Tyr Lys Thr Ser Ile Asn Asn Leu
                20                  25                  30

Gln Trp Tyr Arg Gln Asn Ser Gly Arg Gly Leu Val His Leu Ile Leu
            35                  40                  45

Ile Arg Ser Asn Glu Arg Glu Lys His Ser Gly Arg Leu Arg Val Thr
        50                  55                  60

Leu Asp Thr Ser Lys Lys Ser Ser Ser Leu Leu Ile Thr Ala Ser Arg
 65                  70                  75                  80

Ala Ala Asp Thr Ala Ser Tyr Phe Cys Ala Thr Asp Ala Tyr Gly Thr
                85                  90                  95

Val Gln Phe Gly Lys Gly Thr Arg Leu His Ile Leu Pro
                100                 105
```

<210> SEQ ID NO 70
<211> LENGTH: 109
<212> TYPE: PRT
<213> ORGANISM: Artificial Sequence
<220> FEATURE:
<223> OTHER INFORMATION: Polypeptide

<400> SEQUENCE: 70

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Asn Gly Thr
                85                  90                  95

Val Gln Phe Gly Lys Gly Thr Arg Leu His Ile Leu Pro
            100                 105

<210> SEQ ID NO 71
<211> LENGTH: 109
<212> TYPE: PRT
<213> ORGANISM: Artificial Sequence
<220> FEATURE:
<223> OTHER INFORMATION: Polypeptide

<400> SEQUENCE: 71

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Asn Gly Ser
                85                  90                  95

Val Gln Phe Gly Lys Gly Thr Arg Leu His Ile Leu Pro
            100                 105

<210> SEQ ID NO 72
<211> LENGTH: 109
<212> TYPE: PRT
<213> ORGANISM: Artificial Sequence
<220> FEATURE:
<223> OTHER INFORMATION: Polypeptide

<400> SEQUENCE: 72

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
            20                  25                  30

```
Gln Trp Tyr Arg Gln Asn Ser Gly Arg Gly Leu Val His Leu Ile Leu
             35                  40                  45

Ile Arg Ser Asn Glu Arg Glu Lys His Ser Gly Arg Leu Arg Val Thr
 50                  55                  60

Leu Asp Thr Ser Lys Lys Ser Ser Ser Leu Leu Ile Thr Ala Ser Arg
 65                  70                  75                  80

Ala Ala Asp Thr Ala Ser Tyr Phe Cys Ala Thr Asp Ala Tyr Gly Arg
                 85                  90                  95

Tyr Ile Phe Gly Lys Gly Thr Arg Leu His Ile Leu Pro
                100                 105

<210> SEQ ID NO 73
<211> LENGTH: 109
<212> TYPE: PRT
<213> ORGANISM: Artificial Sequence
<220> FEATURE:
<223> OTHER INFORMATION: Polypeptide

<400> SEQUENCE: 73

Ser Gln Gln Gly Glu Glu Asp Pro Gln Ala Leu Ser Ile Gln Glu Gly
 1               5                  10                  15

Glu Asn Ala Thr Met Asn Cys Ser Tyr Lys Thr Ser Ile Asn Asn Leu
             20                  25                  30

Gln Trp Tyr Arg Gln Asn Ser Gly Arg Gly Leu Val His Leu Ile Leu
             35                  40                  45

Ile Arg Ser Asn Glu Arg Glu Lys His Ser Gly Arg Leu Arg Val Thr
 50                  55                  60

Leu Asp Thr Ser Lys Lys Ser Ser Ser Leu Leu Ile Thr Ala Ser Arg
 65                  70                  75                  80

Ala Ala Asp Thr Ala Ser Tyr Phe Cys Ala Thr Asp Ala Asn Gln Met
                 85                  90                  95

Trp Lys Phe Gly Lys Gly Thr Arg Leu His Ile Leu Pro
                100                 105

<210> SEQ ID NO 74
<211> LENGTH: 109
<212> TYPE: PRT
<213> ORGANISM: Artificial Sequence
<220> FEATURE:
<223> OTHER INFORMATION: Polypeptide

<400> SEQUENCE: 74

Ser Gln Gln Gly Glu Glu Asp Pro Gln Ala Leu Ser Ile Gln Glu Gly
 1               5                  10                  15

Glu Asn Ala Thr Met Asn Cys Ser Tyr Lys Thr Ser Ile Asn Asn Leu
             20                  25                  30

Gln Trp Tyr Arg Gln Asn Ser Gly Arg Gly Leu Val His Leu Ile Leu
             35                  40                  45

Ile Arg Ser Asn Glu Arg Glu Lys His Ser Gly Arg Leu Arg Val Thr
 50                  55                  60

Leu Asp Thr Ser Lys Lys Ser Ser Ser Leu Leu Ile Thr Ala Ser Arg
 65                  70                  75                  80

Ala Ala Asp Thr Ala Ser Tyr Phe Cys Ala Thr Asp Ala Tyr Gly Leu
                 85                  90                  95

Pro Ile Phe Gly Lys Gly Thr Arg Leu His Ile Leu Pro
                100                 105

<210> SEQ ID NO 75
```

```
<211> LENGTH: 109
<212> TYPE: PRT
<213> ORGANISM: Artificial Sequence
<220> FEATURE:
<223> OTHER INFORMATION: Polypeptide

<400> SEQUENCE: 75

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Asn Gly Leu
                85                  90                  95

Pro Val Phe Gly Lys Gly Thr Arg Leu His Ile Leu Pro
            100                 105

<210> SEQ ID NO 76
<211> LENGTH: 109
<212> TYPE: PRT
<213> ORGANISM: Artificial Sequence
<220> FEATURE:
<223> OTHER INFORMATION: Polypeptide

<400> SEQUENCE: 76

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Asn Gly Arg
                85                  90                  95

Trp Glu Phe Gly Lys Gly Thr Arg Leu His Ile Leu Pro
            100                 105

<210> SEQ ID NO 77
<211> LENGTH: 109
<212> TYPE: PRT
<213> ORGANISM: Artificial Sequence
<220> FEATURE:
<223> OTHER INFORMATION: Polypeptide

<400> SEQUENCE: 77

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45
```

```
Ile Arg Ser Asn Glu Arg Glu Lys His Ser Gly Arg Leu Arg Val Thr
 50                  55                  60

Leu Asp Thr Ser Lys Lys Ser Ser Leu Leu Ile Thr Ala Ser Arg
 65                  70                  75                  80

Ala Ala Asp Thr Ala Ser Tyr Phe Cys Ala Thr Asp Ala Asn Gly Thr
                 85                  90                  95

Val Gly Phe Gly Lys Gly Thr Arg Leu His Ile Leu Pro
                100                 105
```

<210> SEQ ID NO 78
<211> LENGTH: 109
<212> TYPE: PRT
<213> ORGANISM: Artificial Sequence
<220> FEATURE:
<223> OTHER INFORMATION: Polypeptide

<400> SEQUENCE: 78

```
Ser Gln Gln Gly Glu Glu Asp Pro Gln Ala Leu Ser Ile Gln Glu Gly
  1               5                  10                  15

Glu Asn Ala Thr Met Asn Cys Ser Tyr Lys Thr Ser Ile Asn Asn Leu
                 20                  25                  30

Gln Trp Tyr Arg Gln Asn Ser Gly Arg Gly Leu Val His Leu Ile Leu
             35                  40                  45

Ile Arg Ser Asn Glu Arg Glu Lys His Ser Gly Arg Leu Arg Val Thr
 50                  55                  60

Leu Asp Thr Ser Lys Lys Ser Ser Leu Leu Ile Thr Ala Ser Arg
 65                  70                  75                  80

Ala Ala Asp Thr Ala Ser Tyr Phe Cys Ala Thr Asp Ala Asn Gly Arg
                 85                  90                  95

Trp Met Phe Gly Lys Gly Thr Arg Leu His Ile Leu Pro
                100                 105
```

<210> SEQ ID NO 79
<211> LENGTH: 109
<212> TYPE: PRT
<213> ORGANISM: Artificial Sequence
<220> FEATURE:
<223> OTHER INFORMATION: Polypeptide

<400> SEQUENCE: 79

```
Ser Gln Gln Gly Glu Glu Asp Pro Gln Ala Leu Ser Ile Gln Glu Gly
  1               5                  10                  15

Glu Asn Ala Thr Met Asn Cys Ser Tyr Lys Thr Ser Ile Asn Asn Leu
                 20                  25                  30

Gln Trp Tyr Arg Gln Asn Ser Gly Arg Gly Leu Val His Leu Ile Leu
             35                  40                  45

Ile Arg Ser Asn Glu Arg Glu Lys His Ser Gly Arg Leu Arg Val Thr
 50                  55                  60

Leu Asp Thr Ser Lys Lys Ser Ser Leu Leu Ile Thr Ala Ser Arg
 65                  70                  75                  80

Ala Ala Asp Thr Ala Ser Tyr Phe Cys Ala Thr Asp Ala Asn Gly Leu
                 85                  90                  95

Trp Ser Phe Gly Lys Gly Thr Arg Leu His Ile Leu Pro
                100                 105
```

<210> SEQ ID NO 80
<211> LENGTH: 109
<212> TYPE: PRT
<213> ORGANISM: Artificial Sequence

```
<220> FEATURE:
<223> OTHER INFORMATION: Polypeptide

<400> SEQUENCE: 80

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Gly Trp Ala Gln Asn Leu
            20                  25                  30

Gln Trp Tyr Arg Gln Asn Ser Gly Arg Gly Leu Val His Leu Ile Leu
        35                  40                  45

Ile Arg Thr Gly Glu Gln Glu Lys His Ser Gly Arg Leu Arg Val Thr
    50                  55                  60

Leu Asp Thr Ser Lys Lys Ser Ser Leu Leu Ile Thr Ala Ser Arg
65                  70                  75                  80

Ala Ala Asp Thr Ala Ser Tyr Phe Cys Ala Thr Asp Ala Asn Ala Arg
                85                  90                  95

Trp Asp Phe Gly Lys Gly Thr Arg Leu His Ile Leu Pro
                100                 105

<210> SEQ ID NO 81
<211> LENGTH: 109
<212> TYPE: PRT
<213> ORGANISM: Artificial Sequence
<220> FEATURE:
<223> OTHER INFORMATION: Polypeptide

<400> SEQUENCE: 81

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Gly Trp Ala Gln Asn Leu
            20                  25                  30

Gln Trp Tyr Arg Gln Asn Ser Gly Arg Gly Leu Val His Leu Ile Leu
        35                  40                  45

Ile Arg Thr Gly Gln Ala Glu Lys His Ser Gly Arg Leu Arg Val Thr
    50                  55                  60

Leu Asp Thr Ser Lys Lys Ser Ser Leu Leu Ile Thr Ala Ser Arg
65                  70                  75                  80

Ala Ala Asp Thr Ala Ser Tyr Phe Cys Ala Thr Asp Ala Asn Ala Arg
                85                  90                  95

Trp Glu Phe Gly Lys Gly Thr Arg Leu His Ile Leu Pro
                100                 105

<210> SEQ ID NO 82
<211> LENGTH: 109
<212> TYPE: PRT
<213> ORGANISM: Artificial Sequence
<220> FEATURE:
<223> OTHER INFORMATION: Polypeptide

<400> SEQUENCE: 82

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Gly Ser Ile Gln Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60
```

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Phe Ala Trp
                85                  90                  95

Trp Ile Phe Gly Lys Gly Thr Arg Leu His Ile Leu Pro
                100                 105

<210> SEQ ID NO 83
<211> LENGTH: 109
<212> TYPE: PRT
<213> ORGANISM: Artificial Sequence
<220> FEATURE:
<223> OTHER INFORMATION: Polypeptide

<400> SEQUENCE: 83

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Gly Trp Val Gln Asn Leu
                20                  25                  30

Gln Trp Tyr Arg Gln Asn Ser Gly Arg Gly Leu Val His Leu Ile Leu
            35                  40                  45

Ile Arg Thr Gly Glu Gln Glu Lys His Ser Gly Arg Leu Arg Val Thr
50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Asn Ala Arg
                85                  90                  95

Trp Asn Phe Gly Lys Gly Thr Arg Leu His Ile Leu Pro
                100                 105

<210> SEQ ID NO 84
<211> LENGTH: 109
<212> TYPE: PRT
<213> ORGANISM: Artificial Sequence
<220> FEATURE:
<223> OTHER INFORMATION: Polypeptide

<400> SEQUENCE: 84

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Gly Ser Ile Gln Asn Leu
                20                  25                  30

Gln Trp Tyr Arg Gln Asn Ser Gly Arg Gly Leu Val His Leu Ile Leu
            35                  40                  45

Ile Arg Thr Gly Glu Gln Glu Lys His Ser Gly Arg Leu Arg Val Thr
50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Trp Ala Arg
                85                  90                  95

Trp Ile Phe Gly Lys Gly Thr Arg Leu His Ile Leu Pro
                100                 105

<210> SEQ ID NO 85
<211> LENGTH: 109
<212> TYPE: PRT
<213> ORGANISM: Artificial Sequence
<220> FEATURE:
<223> OTHER INFORMATION: Polypeptide

<400> SEQUENCE: 85

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Gly Trp Val Gln Asn Leu
            20                  25                  30

Gln Trp Tyr Arg Gln Asn Ser Gly Arg Gly Leu Val His Leu Ile Leu
        35                  40                  45

Ile Arg Thr Gly Gln Ala Glu Lys His Ser Gly Arg Leu Arg Val Thr
    50                  55                  60

Leu Asp Thr Ser Lys Lys Ser Ser Leu Leu Ile Thr Ala Ser Arg
65                  70                  75                  80

Ala Ala Asp Thr Ala Ser Tyr Phe Cys Ala Thr Asp Ala Asn Ala Arg
                85                  90                  95

Trp Glu Phe Gly Lys Gly Thr Arg Leu His Ile Leu Pro
            100                 105

<210> SEQ ID NO 86
<211> LENGTH: 109
<212> TYPE: PRT
<213> ORGANISM: Artificial Sequence
<220> FEATURE:
<223> OTHER INFORMATION: Polypeptide

<400> SEQUENCE: 86

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Gly Ser Ile Gln Asn Leu
            20                  25                  30

Gln Trp Tyr Arg Gln Asn Ser Gly Arg Gly Leu Val His Leu Ile Leu
        35                  40                  45

Ile Arg Thr Gly Glu Gln Glu Lys His Ser Gly Arg Leu Arg Val Thr
    50                  55                  60

Leu Asp Thr Ser Lys Lys Ser Ser Leu Leu Ile Thr Ala Ser Arg
65                  70                  75                  80

Ala Ala Asp Thr Ala Ser Tyr Phe Cys Ala Thr Asp Ala Asn Ala Arg
                85                  90                  95

Trp Asn Phe Gly Lys Gly Thr Arg Leu His Ile Leu Pro
            100                 105

<210> SEQ ID NO 87
<211> LENGTH: 112
<212> TYPE: PRT
<213> ORGANISM: Artificial Sequence
<220> FEATURE:
<223> OTHER INFORMATION: Polypeptide

<400> SEQUENCE: 87

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn His Gly Ala Val Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

```
Pro Ser Glu Pro Arg Asp Ser Ala Val Tyr Phe Cys Ala Ser Ser Leu
                85                  90                  95

Gly Ser Asn Glu Gln Tyr Phe Gly Pro Gly Thr Arg Leu Thr Val Thr
            100                 105                 110

<210> SEQ ID NO 88
<211> LENGTH: 112
<212> TYPE: PRT
<213> ORGANISM: Artificial Sequence
<220> FEATURE:
<223> OTHER INFORMATION: Polypeptide

<400> SEQUENCE: 88

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn His Gly Ala Val Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Gln Arg
                85                  90                  95

Gly Ser Asn Glu Gln Tyr Phe Gly Pro Gly Thr Arg Leu Thr Val Thr
            100                 105                 110

<210> SEQ ID NO 89
<211> LENGTH: 112
<212> TYPE: PRT
<213> ORGANISM: Artificial Sequence
<220> FEATURE:
<223> OTHER INFORMATION: Polypeptide

<400> SEQUENCE: 89

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn His Gly Ala Val Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Gln Lys
                85                  90                  95

Gly Ala Asn Glu Gln Tyr Phe Gly Pro Gly Thr Arg Leu Thr Val Thr
            100                 105                 110

<210> SEQ ID NO 90
<211> LENGTH: 112
<212> TYPE: PRT
<213> ORGANISM: Artificial Sequence
<220> FEATURE:
<223> OTHER INFORMATION: Polypeptide
```

-continued

<400> SEQUENCE: 90

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn His Gly Ala Val Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Gln Leu
                85                  90                  95

Gly Ser Asn Glu Gln Tyr Phe Gly Pro Gly Thr Arg Leu Thr Val Thr
            100                 105                 110

<210> SEQ ID NO 91
<211> LENGTH: 112
<212> TYPE: PRT
<213> ORGANISM: Artificial Sequence
<220> FEATURE:
<223> OTHER INFORMATION: Polypeptide

<400> SEQUENCE: 91

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn His Gly Ala Val Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Gln Leu
                85                  90                  95

Gly Ala Asn Glu Gln Tyr Phe Gly Pro Gly Thr Arg Leu Thr Val Thr
            100                 105                 110

<210> SEQ ID NO 92
<211> LENGTH: 112
<212> TYPE: PRT
<213> ORGANISM: Artificial Sequence
<220> FEATURE:
<223> OTHER INFORMATION: Polypeptide

<400> SEQUENCE: 92

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Gln Leu
            85                  90                  95

Gly Gly Asn Glu Gln Tyr Phe Gly Pro Gly Thr Arg Leu Thr Val Thr
        100                 105                 110

<210> SEQ ID NO 93
<211> LENGTH: 112
<212> TYPE: PRT
<213> ORGANISM: Artificial Sequence
<220> FEATURE:
<223> OTHER INFORMATION: Polypeptide

<400> SEQUENCE: 93

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Gln Lys
            85                  90                  95

Gly Ala Asn Glu Gln Tyr Phe Gly Pro Gly Thr Arg Leu Thr Val Thr
        100                 105                 110

<210> SEQ ID NO 94
<211> LENGTH: 112
<212> TYPE: PRT
<213> ORGANISM: Artificial Sequence
<220> FEATURE:
<223> OTHER INFORMATION: Polypeptide

<400> SEQUENCE: 94

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Gln Leu
            85                  90                  95

Gly Pro Asn Glu Gln Tyr Phe Gly Pro Gly Thr Arg Leu Thr Val Thr
        100                 105                 110

<210> SEQ ID NO 95
<211> LENGTH: 112
<212> TYPE: PRT
<213> ORGANISM: Artificial Sequence
<220> FEATURE:
<223> OTHER INFORMATION: Polypeptide

<400> SEQUENCE: 95

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Gln Arg
                85                  90                  95

Gly Ala Asn Glu Gln Tyr Phe Gly Pro Gly Thr Arg Leu Thr Val Thr
            100                 105                 110

<210> SEQ ID NO 96
<211> LENGTH: 112
<212> TYPE: PRT
<213> ORGANISM: Artificial Sequence
<220> FEATURE:
<223> OTHER INFORMATION: Polypeptide

<400> SEQUENCE: 96

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Gln Met
                85                  90                  95

Gly Ser Asn Glu Gln Tyr Phe Gly Pro Gly Thr Arg Leu Thr Val Thr
            100                 105                 110

<210> SEQ ID NO 97
<211> LENGTH: 112
<212> TYPE: PRT
<213> ORGANISM: Artificial Sequence
<220> FEATURE:
<223> OTHER INFORMATION: Polypeptide

<400> SEQUENCE: 97

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

```
Pro Ser Glu Pro Arg Asp Ser Ala Val Tyr Phe Cys Ala Ser Gln Leu
                85                  90                  95

Gly Ser Asn Glu Gln Tyr Phe Gly Pro Gly Thr Arg Leu Thr Val Thr
            100                 105                 110
```

<210> SEQ ID NO 98
<211> LENGTH: 112
<212> TYPE: PRT
<213> ORGANISM: Artificial Sequence
<220> FEATURE:
<223> OTHER INFORMATION: Polypeptide

<400> SEQUENCE: 98

```
Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
                20                  25                  30

Phe Trp Tyr Arg Gln Thr Met Met Arg Gly Leu Glu Leu Leu Ile Tyr
            35                  40                  45

Phe Asn Asn Asn Val Pro Ile Asp Asp Ser Gly Met Pro Glu Asp Arg
        50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Gln Leu
                85                  90                  95

Gly Ala Asn Glu Gln Tyr Phe Gly Pro Gly Thr Arg Leu Thr Val Thr
            100                 105                 110
```

<210> SEQ ID NO 99
<211> LENGTH: 112
<212> TYPE: PRT
<213> ORGANISM: Artificial Sequence
<220> FEATURE:
<223> OTHER INFORMATION: Polypeptide

<400> SEQUENCE: 99

```
Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
                20                  25                  30

Phe Trp Tyr Arg Gln Thr Met Met Arg Gly Leu Glu Leu Leu Ile Tyr
            35                  40                  45

Phe Asn Asn Asn Val Pro Ile Asp Asp Ser Gly Met Pro Glu Asp Arg
        50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Gln Met
                85                  90                  95

Gly Ser Asn Glu Gln Tyr Phe Gly Pro Gly Thr Arg Leu Thr Val Thr
            100                 105                 110
```

<210> SEQ ID NO 100
<211> LENGTH: 112
<212> TYPE: PRT
<213> ORGANISM: Artificial Sequence
<220> FEATURE:
<223> OTHER INFORMATION: Polypeptide

<400> SEQUENCE: 100

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Gln Arg
                85                  90                  95

Gly Ser Asn Glu Gln Tyr Phe Gly Pro Gly Thr Arg Leu Thr Val Thr
            100                 105                 110

<210> SEQ ID NO 101
<211> LENGTH: 112
<212> TYPE: PRT
<213> ORGANISM: Artificial Sequence
<220> FEATURE:
<223> OTHER INFORMATION: Polypeptide

<400> SEQUENCE: 101

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Gln Met
                85                  90                  95

Gly Ala Asn Glu Gln Tyr Phe Gly Pro Gly Thr Arg Leu Thr Val Thr
            100                 105                 110

<210> SEQ ID NO 102
<211> LENGTH: 112
<212> TYPE: PRT
<213> ORGANISM: Artificial Sequence
<220> FEATURE:
<223> OTHER INFORMATION: Polypeptide

<400> SEQUENCE: 102

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

```
Pro Ser Glu Pro Arg Asp Ser Ala Val Tyr Phe Cys Ala Ser Met Leu
                85                  90                  95

Gly Ser Asn Glu Gln Tyr Phe Gly Pro Gly Thr Arg Leu Thr Val Thr
            100                 105                 110
```

<210> SEQ ID NO 103
<211> LENGTH: 203
<212> TYPE: PRT
<213> ORGANISM: Artificial Sequence
<220> FEATURE:
<223> OTHER INFORMATION: Polypeptide

<400> SEQUENCE: 103

```
Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
50                  55                  60

Leu Asp Thr Ser Lys Lys Ser Ser Leu Leu Ile Thr Ala Ser Arg
65                  70                  75                  80

Ala Ala Asp Thr Ala Ser Tyr Phe Cys Ala Thr Asp Ala Asn Gly Lys
                85                  90                  95

Ile Ile Phe Gly Lys Gly Thr Arg Leu His Ile Leu Pro Asn Ile Gln
            100                 105                 110

Asn Pro Asp Pro Ala Val Tyr Gln Leu Arg Asp Ser Lys Ser Ser Asp
        115                 120                 125

Lys Ser Val Cys Leu Phe Thr Asp Phe Asp Ser Gln Thr Asn Val Ser
130                 135                 140

Gln Ser Lys Asp Ser Asp Val Tyr Ile Thr Asp Lys Thr Val Leu Asp
145                 150                 155                 160

Met Arg Ser Met Asp Phe Lys Ser Asn Ser Ala Val Ala Trp Ser Asn
                165                 170                 175

Lys Ser Asp Phe Ala Cys Ala Asn Ala Phe Asn Asn Ser Ile Ile Pro
            180                 185                 190

Glu Asp Thr Phe Phe Pro Ser Pro Glu Ser Ser
        195                 200
```

<210> SEQ ID NO 104
<211> LENGTH: 242
<212> TYPE: PRT
<213> ORGANISM: Artificial Sequence
<220> FEATURE:
<223> OTHER INFORMATION: Polypeptide

<400> SEQUENCE: 104

```
Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
50                  55                  60
```

```
                    Phe Ser Ala Lys Met Pro Asn Ala Ser Phe Ser Thr Leu Lys Ile Gln
                    65                  70                  75                  80

Pro Ser Glu Pro Arg Asp Ser Ala Val Tyr Phe Cys Ala Ser Ser Leu
                                    85                  90                  95

Gly Ser Asn Glu Gln Tyr Phe Gly Pro Gly Thr Arg Leu Thr Val Thr
                                100                 105                 110

Glu Asp Leu Lys Asn Val Phe Pro Pro Glu Val Ala Val Phe Glu Pro
                                115                 120                 125

Ser Glu Ala Glu Ile Ser His Thr Gln Lys Ala Thr Leu Val Cys Leu
                    130                 135                 140

Ala Thr Gly Phe Tyr Pro Asp His Val Glu Leu Ser Trp Trp Val Asn
                    145                 150                 155                 160

Gly Lys Glu Val His Ser Gly Val Ser Thr Asp Pro Gln Pro Leu Lys
                                    165                 170                 175

Glu Gln Pro Ala Leu Asn Asp Ser Arg Tyr Ala Leu Ser Ser Arg Leu
                                180                 185                 190

Arg Val Ser Ala Thr Phe Trp Gln Asp Pro Arg Asn His Phe Arg Cys
                                    195                 200                 205

Gln Val Gln Phe Tyr Gly Leu Ser Glu Asn Asp Glu Trp Thr Gln Asp
                                210                 215                 220

Arg Ala Lys Pro Val Thr Gln Ile Val Ser Ala Glu Ala Trp Gly Arg
                    225                 230                 235                 240

Ala Asp

<210> SEQ ID NO 105
<211> LENGTH: 9
<212> TYPE: PRT
<213> ORGANISM: Artificial Sequence
<220> FEATURE:
<223> OTHER INFORMATION: Polypeptide

<400> SEQUENCE: 105

Ser Leu Leu Met Trp Ile Thr Gln Cys
1               5

<210> SEQ ID NO 106
<211> LENGTH: 5
<212> TYPE: PRT
<213> ORGANISM: Artificial Sequence
<220> FEATURE:
<223> OTHER INFORMATION: Polypeptide

<400> SEQUENCE: 106

Thr Ser Ile Asn Asn
1               5

<210> SEQ ID NO 107
<211> LENGTH: 7
<212> TYPE: PRT
<213> ORGANISM: Artificial Sequence
<220> FEATURE:
<223> OTHER INFORMATION: Polypeptide

<400> SEQUENCE: 107

Ile Arg Ser Asn Glu Arg Glu
1               5

<210> SEQ ID NO 108
<211> LENGTH: 9
<212> TYPE: PRT
```

```
<213> ORGANISM: Artificial Sequence
<220> FEATURE:
<223> OTHER INFORMATION: Polypeptide

<400> SEQUENCE: 108

Ala Thr Asp Ala Asn Gly Lys Ile Ile
1               5

<210> SEQ ID NO 109
<211> LENGTH: 5
<212> TYPE: PRT
<213> ORGANISM: Artificial Sequence
<220> FEATURE:
<223> OTHER INFORMATION: Polypeptide

<400> SEQUENCE: 109

Ser Gly His Asp Tyr
1               5

<210> SEQ ID NO 110
<211> LENGTH: 6
<212> TYPE: PRT
<213> ORGANISM: Artificial Sequence
<220> FEATURE:
<223> OTHER INFORMATION: Polypeptide

<400> SEQUENCE: 110

Phe Asn Asn Asn Val Pro
1               5

<210> SEQ ID NO 111
<211> LENGTH: 10
<212> TYPE: PRT
<213> ORGANISM: Artificial Sequence
<220> FEATURE:
<223> OTHER INFORMATION: Polypeptide

<400> SEQUENCE: 111

Ala Ser Ser Leu Gly Ser Asn Glu Gln Tyr
1               5                   10

<210> SEQ ID NO 112
<211> LENGTH: 9
<212> TYPE: PRT
<213> ORGANISM: Artificial Sequence
<220> FEATURE:
<223> OTHER INFORMATION: Polypeptide

<400> SEQUENCE: 112

Ala Thr Asp Ala Asn Ala Arg Trp Asn
1               5

<210> SEQ ID NO 113
<211> LENGTH: 9
<212> TYPE: PRT
<213> ORGANISM: Artificial Sequence
<220> FEATURE:
<223> OTHER INFORMATION: Polypeptide

<400> SEQUENCE: 113

Ala Thr Asp Ala Asn Ala Arg Trp Glu
1               5

<210> SEQ ID NO 114
<211> LENGTH: 9
<212> TYPE: PRT
<213> ORGANISM: Artificial Sequence
```

```
<220> FEATURE:
<223> OTHER INFORMATION: Polypeptide

<400> SEQUENCE: 114

Ala Thr Asp Ala Asn Ala Arg Trp Asp
1               5

<210> SEQ ID NO 115
<211> LENGTH: 9
<212> TYPE: PRT
<213> ORGANISM: Artificial Sequence
<220> FEATURE:
<223> OTHER INFORMATION: Polypeptide

<400> SEQUENCE: 115

Ala Thr Asp Ala Phe Ala Trp Trp Ile
1               5

<210> SEQ ID NO 116
<211> LENGTH: 9
<212> TYPE: PRT
<213> ORGANISM: Artificial Sequence
<220> FEATURE:
<223> OTHER INFORMATION: Polypeptide

<400> SEQUENCE: 116

Ala Thr Asp Ala Trp Ala Arg Trp Ile
1               5

<210> SEQ ID NO 117
<211> LENGTH: 5
<212> TYPE: PRT
<213> ORGANISM: Artificial Sequence
<220> FEATURE:
<223> OTHER INFORMATION: Polypeptide

<400> SEQUENCE: 117

Gly Ser Ile Gln Asn
1               5

<210> SEQ ID NO 118
<211> LENGTH: 5
<212> TYPE: PRT
<213> ORGANISM: Artificial Sequence
<220> FEATURE:
<223> OTHER INFORMATION: Polypeptide

<400> SEQUENCE: 118

Gly Trp Ala Gln Asn
1               5

<210> SEQ ID NO 119
<211> LENGTH: 5
<212> TYPE: PRT
<213> ORGANISM: Artificial Sequence
<220> FEATURE:
<223> OTHER INFORMATION: Polypeptide

<400> SEQUENCE: 119

Gly Trp Val Gln Asn
1               5

<210> SEQ ID NO 120
<211> LENGTH: 7
<212> TYPE: PRT
<213> ORGANISM: Artificial Sequence
<220> FEATURE:
```

```
<223> OTHER INFORMATION: Polypeptide

<400> SEQUENCE: 120

Ile Arg Thr Gly Glu Gln Glu
1               5

<210> SEQ ID NO 121
<211> LENGTH: 7
<212> TYPE: PRT
<213> ORGANISM: Artificial Sequence
<220> FEATURE:
<223> OTHER INFORMATION: Polypeptide

<400> SEQUENCE: 121

Ile Arg Thr Gly Gln Ala Glu
1               5

<210> SEQ ID NO 122
<211> LENGTH: 6
<212> TYPE: PRT
<213> ORGANISM: Artificial Sequence
<220> FEATURE:
<223> OTHER INFORMATION: Polypeptide

<400> SEQUENCE: 122

Phe Asn His Gly Ala Val
1               5

<210> SEQ ID NO 123
<211> LENGTH: 10
<212> TYPE: PRT
<213> ORGANISM: Artificial Sequence
<220> FEATURE:
<223> OTHER INFORMATION: Polypeptide

<400> SEQUENCE: 123

Ala Ser Gln Arg Gly Ser Asn Glu Gln Tyr
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Polypeptide

<400> SEQUENCE: 124

Ala Ser Gln Lys Gly Ala Asn Glu Gln Tyr
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Polypeptide

<400> SEQUENCE: 125

Ala Ser Gln Leu Gly Ser Asn Glu Gln Tyr
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Polypeptide
```

<400> SEQUENCE: 126

Ala Ser Gln Leu Gly Ala Asn Glu Gln Tyr
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Polypeptide

<400> SEQUENCE: 127

Ala Ser Gln Leu Gly Gly Asn Glu Gln Tyr
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Polypeptide

<400> SEQUENCE: 128

Ala Ser Gln Leu Gly Pro Asn Glu Gln Tyr
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Polypeptide

<400> SEQUENCE: 129

Ala Ser Gln Arg Gly Ala Asn Glu Gln Tyr
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Polypeptide

<400> SEQUENCE: 130

Ala Ser Gln Met Gly Ser Asn Glu Gln Tyr
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Polypeptide

<400> SEQUENCE: 131

Ala Ser Gln Met Gly Ala Asn Glu Gln Tyr
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Polypeptide

```
<400> SEQUENCE: 132

Ala Ser Met Leu Gly Ser Asn Glu Gln Tyr
1               5                   10

<210> SEQ ID NO 133
<211> LENGTH: 9
<212> TYPE: PRT
<213> ORGANISM: Artificial Sequence
<220> FEATURE:
<223> OTHER INFORMATION: Polypeptide

<400> SEQUENCE: 133

Met Tyr Asp Glu Asn Gly Lys Ile Ile
1               5

<210> SEQ ID NO 134
<211> LENGTH: 9
<212> TYPE: PRT
<213> ORGANISM: Artificial Sequence
<220> FEATURE:
<223> OTHER INFORMATION: Polypeptide

<400> SEQUENCE: 134

Met Tyr Asp Gln Asn Gly Lys Ile Ile
1               5

<210> SEQ ID NO 135
<211> LENGTH: 9
<212> TYPE: PRT
<213> ORGANISM: Artificial Sequence
<220> FEATURE:
<223> OTHER INFORMATION: Polypeptide

<400> SEQUENCE: 135

Ala Thr Asp Ala Tyr Gly Thr Val Gln
1               5

<210> SEQ ID NO 136
<211> LENGTH: 9
<212> TYPE: PRT
<213> ORGANISM: Artificial Sequence
<220> FEATURE:
<223> OTHER INFORMATION: Polypeptide

<400> SEQUENCE: 136

Ala Thr Asp Ala Asn Gly Thr Val Gln
1               5

<210> SEQ ID NO 137
<211> LENGTH: 9
<212> TYPE: PRT
<213> ORGANISM: Artificial Sequence
<220> FEATURE:
<223> OTHER INFORMATION: Polypeptide

<400> SEQUENCE: 137

Ala Thr Asp Ala Asn Gly Ser Val Gln
1               5

<210> SEQ ID NO 138
<211> LENGTH: 9
<212> TYPE: PRT
<213> ORGANISM: Artificial Sequence
<220> FEATURE:
<223> OTHER INFORMATION: Polypeptide
```

<400> SEQUENCE: 138

Ala Thr Asp Ala Tyr Gly Arg Tyr Ile
1               5

<210> SEQ ID NO 139
<211> LENGTH: 9
<212> TYPE: PRT
<213> ORGANISM: Artificial Sequence
<220> FEATURE:
<223> OTHER INFORMATION: Polypeptide

<400> SEQUENCE: 139

Ala Thr Asp Ala Asn Gln Met Trp Lys
1               5

<210> SEQ ID NO 140
<211> LENGTH: 9
<212> TYPE: PRT
<213> ORGANISM: Artificial Sequence
<220> FEATURE:
<223> OTHER INFORMATION: Polypeptide

<400> SEQUENCE: 140

Ala Thr Asp Ala Tyr Gly Leu Pro Ile
1               5

<210> SEQ ID NO 141
<211> LENGTH: 9
<212> TYPE: PRT
<213> ORGANISM: Artificial Sequence
<220> FEATURE:
<223> OTHER INFORMATION: Polypeptide

<400> SEQUENCE: 141

Ala Thr Asp Ala Asn Gly Leu Pro Val
1               5

<210> SEQ ID NO 142
<211> LENGTH: 9
<212> TYPE: PRT
<213> ORGANISM: Artificial Sequence
<220> FEATURE:
<223> OTHER INFORMATION: Polypeptide

<400> SEQUENCE: 142

Ala Thr Asp Ala Asn Gly Arg Trp Glu
1               5

<210> SEQ ID NO 143
<211> LENGTH: 9
<212> TYPE: PRT
<213> ORGANISM: Artificial Sequence
<220> FEATURE:
<223> OTHER INFORMATION: Polypeptide

<400> SEQUENCE: 143

Ala Thr Asp Ala Asn Gly Thr Val Gly
1               5

<210> SEQ ID NO 144
<211> LENGTH: 9
<212> TYPE: PRT
<213> ORGANISM: Artificial Sequence
<220> FEATURE:
<223> OTHER INFORMATION: Polypeptide

```
<400> SEQUENCE: 144

Ala Thr Asp Ala Asn Gly Arg Trp Met
1               5

<210> SEQ ID NO 145
<211> LENGTH: 9
<212> TYPE: PRT
<213> ORGANISM: Artificial Sequence
<220> FEATURE:
<223> OTHER INFORMATION: Polypeptide

<400> SEQUENCE: 145

Ala Thr Asp Ala Asn Gly Leu Trp Ser
1               5

<210> SEQ ID NO 146
<211> LENGTH: 9
<212> TYPE: PRT
<213> ORGANISM: Artificial Sequence
<220> FEATURE:
<223> OTHER INFORMATION: Polypeptide

<400> SEQUENCE: 146

Ala Thr Asp Ala Trp Ala Arg Trp Ile
1               5

<210> SEQ ID NO 147
<211> LENGTH: 6
<212> TYPE: DNA
<213> ORGANISM: Artificial Sequence
<220> FEATURE:
<223> OTHER INFORMATION: Polynucleotide

<400> SEQUENCE: 147 ccatgg                                                                       6

<210> SEQ ID NO 148
<211> LENGTH: 8
<212> TYPE: DNA
<213> ORGANISM: Artificial Sequence
<220> FEATURE:
<223> OTHER INFORMATION: Polynucleotide

<400> SEQUENCE: 148 gcggccgc                                                                     8

<210> SEQ ID NO 149
<211> LENGTH: 9
<212> TYPE: PRT
<213> ORGANISM: Artificial Sequence
<220> FEATURE:
<221> NAME/KEY: DOMAIN
<222> LOCATION: (1)..(2)
<223> OTHER INFORMATION: Xaa is any amino acid
<220> FEATURE:
<221> NAME/KEY: DOMAIN
<222> LOCATION: (4)..(9)
<223> OTHER INFORMATION: Xaa is any amino acid
<220> FEATURE:
<223> OTHER INFORMATION: Polypeptide

<400> SEQUENCE: 149

Xaa Xaa Asp Xaa Xaa Xaa Xaa Xaa Xaa
1               5

<210> SEQ ID NO 150
<211> LENGTH: 5
```

<212> TYPE: PRT
<213> ORGANISM: Artificial Sequence
<220> FEATURE:
<223> OTHER INFORMATION: Polypeptide
<220> FEATURE:
<221> NAME/KEY: DOMAIN
<222> LOCATION: (1)..(4)
<223> OTHER INFORMATION: Xaa is any amino acid

<400> SEQUENCE: 150

Xaa Xaa Xaa Xaa Asn
1               5

<210> SEQ ID NO 151
<211> LENGTH: 7
<212> TYPE: PRT
<213> ORGANISM: Artificial Sequence
<220> FEATURE:
<223> OTHER INFORMATION: Polyeptide
<220> FEATURE:
<221> NAME/KEY: DOMAIN
<222> LOCATION: (3)..(6)
<223> OTHER INFORMATION: Xaa is any amino acid

<400> SEQUENCE: 151

Ile Arg Xaa Xaa Xaa Xaa Glu
1               5

<210> SEQ ID NO 152
<211> LENGTH: 6
<212> TYPE: PRT
<213> ORGANISM: Artificial Sequence
<220> FEATURE:
<223> OTHER INFORMATION: Polypeptide
<220> FEATURE:
<221> NAME/KEY: DOMAIN
<222> LOCATION: (3)..(6)
<223> OTHER INFORMATION: Xaa is any amino acid

<400> SEQUENCE: 152

Phe Asn Xaa Xaa Xaa Xaa
1               5

<210> SEQ ID NO 153
<211> LENGTH: 10
<212> TYPE: PRT
<213> ORGANISM: Artificial Sequence
<220> FEATURE:
<223> OTHER INFORMATION: Polypeptide
<220> FEATURE:
<221> NAME/KEY: DOMAIN
<222> LOCATION: (3)..(4)
<223> OTHER INFORMATION: Xaa is any amino acid
<220> FEATURE:
<221> NAME/KEY: DOMAIN
<222> LOCATION: (6)..(6)
<223> OTHER INFORMATION: Xaa is any amino acid

<400> SEQUENCE: 153

Ala Ser Xaa Xaa Gly Xaa Asn Glu Gln Tyr
1               5                   10